United States Patent
Lewis et al.

(10) Patent No.: US 9,890,127 B2
(45) Date of Patent: Feb. 13, 2018

(54) COMPOUNDS AND COMPOSITIONS FOR THE TREATMENT OF CANCER

(71) Applicants: THE BROAD INSTITUTE, INC., Cambridge, MA (US); DANA FARBER CANCER INSTITUTE, INC., Boston, MA (US)

(72) Inventors: Timothy A. Lewis, Marlborough, MA (US); Benito Munoz, Newtonville, MA (US); Lucian De Waal, Watertown, MA (US); Heidi Greulich, Arlington, MA (US); Matthew Meyerson, Concord, MA (US); Lara Nicole Gechijian, Lincoln, MA (US)

(73) Assignees: The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/775,354

(22) PCT Filed: Mar. 11, 2014

(86) PCT No.: PCT/US2014/023263
§ 371 (c)(1),
(2) Date: Sep. 11, 2015

(87) PCT Pub. No.: WO2014/164704
PCT Pub. Date: Oct. 9, 2014

(65) Prior Publication Data
US 2016/0016913 A1 Jan. 21, 2016

Related U.S. Application Data

(60) Provisional application No. 61/776,520, filed on Mar. 11, 2013.

(51) Int. Cl.
*A61K 31/535* (2006.01)
*C07D 237/04* (2006.01)
*C07D 401/10* (2006.01)
*C07D 403/10* (2006.01)
*C07D 413/10* (2006.01)

(52) U.S. Cl.
CPC ......... *C07D 237/04* (2013.01); *C07D 401/10* (2013.01); *C07D 403/10* (2013.01); *C07D 413/10* (2013.01)

(58) Field of Classification Search
None
See application file for complete search history.

(56) References Cited

U.S. PATENT DOCUMENTS 3,824,271 A 7/1974 Allen et al.
4,052,395 A 10/1977 Jojima et al.
4,092,311 A 5/1978 Hanifin, Jr. et al.
4,661,486 A 4/1987 Takeshiba et al.
4,699,908 A * 10/1987 Gainer ................. C07D 237/04
                                                       514/236.5
5,053,338 A 10/1991 Bray et al.

FOREIGN PATENT DOCUMENTS

| EP | 0 172 141 | 2/1986 |
| EP | 0 180 542 A2 | 5/1986 |
| EP | 0 327 800 | 8/1989 |
| EP | 0 791 584 A1 | 8/1997 |
| EP | 2 253 625 A1 | 11/2010 |
| JP | 5-140116 A | 6/1993 |
| WO | 199212135 A1 | 7/1992 |

OTHER PUBLICATIONS

STN Search Report w/ CAS RN 103585-27-9 (Accession No. 1986:478948).*
Williams et al (Foye's Principles of Medicinal Chemistry, 5th Edition, pp. 37-68, 2002).*
Varnerin, Jeffrey P. et al. "Expression, Refolding, and Purification of Recombinant Human Phosphodiesterase 3B: Definition of the N-Terminus of the Catalytic Core", Protein Expression and Purification, pp. 1-10 (Jun. 2004).
Edmondson, Scott D. et al. "Benzyl Vinylogous Amide Substituted Aryldihydropyridazinones and Aryldimethylpyrazolones as Potent and Selective PDE3B Inhibitors", Bioorganic & Medicinal Chemistry Letters, pp. 1-8 (Nov. 17, 2003).
Seik, Toshimi et al. "Studies on Agents With Vasodilator and Beta-Blocking Activites. V. Synthesis and Pharmacological Activity of the Optical Isomers of TZC-5665", Chem. Pharm. Bull 46(1) 84-96 (1998).
Wang, Lisheng et al. "Synthesis and Anti-Congestive Heart Failure Activity of Novel Levosimendan Analogues", Medical Chemistry Research, 20, pp. 287-292, (2011).
Howson, W. et al. "Synthesis and Biological Activity of the Four Stereoisomers of 6-[4-[3-[[2-Hydroxy-3-4[-[2-(Cyclopropyl-methoxy)Ethyl]Phenoxy]Propyl]Amino]-Propionamido]Phenyl]-5-Methyl-4,5-Dihydro-3(2H)-Pyridazinone, a Combined Vasodilator and Beta.-Adrenoceptor Antagonist", J. MEd. Chem. 31, pp. 352-356 (1988).
International Search Report and Written Opinion for corresponding PCT/US2014/023263 dated Nov. 6, 2014.
International Preliminary Report on Patentability for corresponding PCT/US2014/023263, dated Sep. 24, 2015.
Goeschke, R. et al, "6-(4-Morpholino-phenyl)-4,5-dihydro-2H-pyridazine-3-ones:potent platelet aggregation inhibitors and antithrombotics", Eur. J. Med. Chem, 26, pp. 715-721 (1991).
Examination Report from corresponding EP Applicaiton 14 724 186.3 dated Jan. 2, 2017.

* cited by examiner

*Primary Examiner* — Craig Ricci
(74) *Attorney, Agent, or Firm* — Thomas J. Engellenner; Reza Mollaaghababa; Pepper Hamilton LLP

(57) ABSTRACT

Disclosed are compounds, such as pyridazinones, that can be, inter alia, used for treating cancer.

12 Claims, 3 Drawing Sheets

Figure 1. (A) Structure of putative *TP53* mutant synthetic lethal small molecule (B) Dose response curves of Compound 1B in *TP53* mutant (H1734) and wild-type (A549) cell lines showing selective killing of *TP53* mutant cell line.

COMPOUNDS AND COMPOSITIONS FOR THE TREATMENT OF CANCER

CROSS REFERENCE TO RELATED APPLICATIONS

This application claims priority to U.S. Provisional Application No. 61/776,520, filed Mar. 11, 2013, which is hereby incorporated by reference in its entirety.

REFERENCE TO GOVERNMENT GRANTS

The present invention was made by U.S. Government support under Grant No. HG005032 awarded by the National Institutes of Health. The government has certain rights in the invention.

FIELD OF THE INVENTION

The present invention is directed, in part, to compounds (e.g. pyridazinones), or pharmaceutically acceptable salts thereof, for treating cancer.

BACKGROUND OF THE INVENTION

Cancer remains a major cause of cancer death in the United States and world-wide. New treatments are, therefore, required. The presently disclosed subject matter provides new compounds and methods of using the same to treat cancer.

SUMMARY OF THE INVENTION

Embodiments disclosed herein provide compounds of Formula I or a pharmaceutically acceptable salt, ester or prodrug thereof:

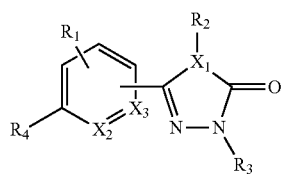

Formula I wherein:
$X_1$ is -$A_1$-$A_2$-$A_3$-$A_4$-
$X_2$ is C or N,
$X_3$ is C or N
$R_1$ is H, halo, optionally substituted alkyl, optionally substituted alkenyl, alkynyl, haloalkyl, optionally substituted aryl, optionally substituted heteroaryl, optionally substituted carbocycle, optionally substituted heterocycle, optionally substituted alkoxy, optionally substituted amine, cyano, or optionally substituted arylalkyl,
$R_2$ is optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amine, cyano, or optionally substituted arylalkyl,
$R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl,
$R_4$ is $OR_5$, $NR_5R_6$, $NR_5C(=O)R_6$, or

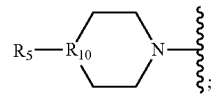

or $R_4$ and $R_1$ together with the atoms to which they are connected form an aryl, heteroaryl, heterocycle or carbocycle ring of 5-8 atoms,
wherein $A_1$, $A_2$, $A_3$, and $A_4$ are independently carbon or null,
wherein when two or more of $A_1$, $A_2$, $A_3$, and $A_4$ are carbons, the bonds between the carbons are optionally double bonds,
wherein each $R_2$ connected to each of $A_1$, $A_2$, $A_3$, and $A_4$ is independent of one another, wherein $R_5$ and $R_6$ are independently null, H, —OH, =O, halo, haloalkyl, alkyl, alkynyl, alkenyl, aryl, arylalkyl, heteroaryl, carbocycle, heterocycle, cyano, alkoxy, amine, wherein $R_5$ and $R_6$ can be further substituted,
wherein $R_{10}$ is C, N, O, or S.

In some embodiments, the compounds, or a pharmaceutically acceptable salt, ester or prodrug thereof have a formula of Formula I-a or Formula I-b

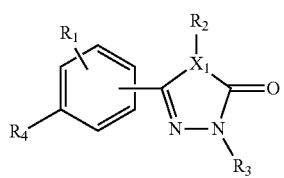

I-a

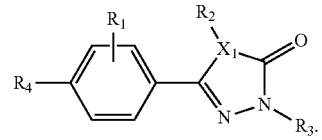

I-b

In some embodiments, the compounds, or a pharmaceutically acceptable salt, ester or prodrug thereof have a formula of Formula II

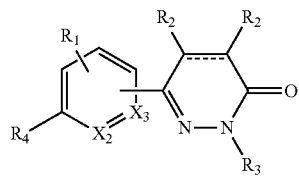

Formula II wherein
----- is an optional double bond,
$X_2$ is C or N,
$X_3$ is C or N
$R_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl, each $R_2$ is independently selected from an optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amino, cyano, or optionally substituted arylalkyl, $R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl, $R_4$ is $OR_5$, $NR_5R_6$, $NR_5C(=O)R_6$, or

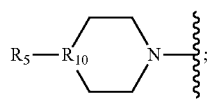

$R_4$ and $R_1$ form a aryl, heteroaryl, heterocycle or carbocycle ring of 5-8 atoms fused to the atoms to which $R_4$ and $R_1$ are attached, wherein $R_5$ and $R_6$ are independently null, H, —OH, =O, halo, haloalkyl, alkyl, alkynyl, alkenyl, aryl, arylalkyl, heteroaryl, carbocycle, heterocycle, cyano, alkoxy, amino or, wherein $R_5$ and $R_6$ can be further substituted;

$R_7$ and $R_8$ are independently null, H, —OH, =O, halo, haloalkyl, alkyl, alkynyl, alkenyl, aryl, arylalkyl, heteroaryl, carbocycle, heterocycle, cyano, alkoxy, amino or $R_7$ and $R_8$ form a ring with the N, such that the ring formed by $R_7$, $R_8$, and N is fused with the ring that the N is attached to, wherein $R_7$ and $R_8$ can be further substituted; and $R_{10}$ is N, O, or S.

In some embodiments, the compounds, or a pharmaceutically acceptable salt, ester or prodrug thereof have a formula of Formula III,

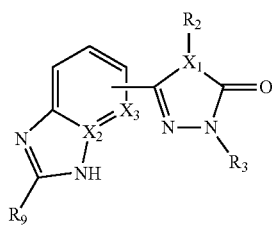

Formula III wherein:
$X_1$ is -$A_1$-$A_2$-$A_3$-$A_4$-
$X_2$ is C or N,
$X_3$ is C or N
$R_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl, $R_2$ is optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amino, cyano, or optionally substituted arylalkyl, $R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl, $R_9$ is optionally substituted $C_1$-$C_6$ alkyl.

wherein $A_1$, $A_2$, $A_3$, and $A_4$ are independently carbon or null, wherein when two or more of $A_1$, $A_2$, $A_3$, and $A_4$ are carbons, the bonds between the carbons are optionally double bonds, wherein each $R_2$ connected to each of $A_1$, $A_2$, $A_3$, and $A_4$ is independent of one another.

In some embodiments, the compounds, or a pharmaceutically acceptable salt, ester or prodrug thereof have a formula of Formula II-a

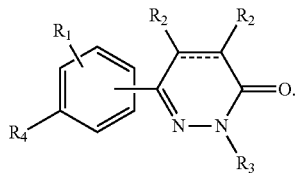

II-a

In some embodiments, the compounds, or a pharmaceutically acceptable salt, ester or prodrug thereof have a formula of Formula II-b

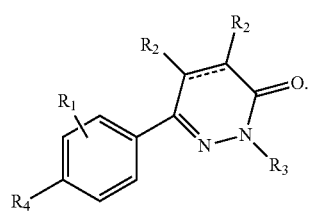

II-b

In some embodiments, the compounds, or a pharmaceutically acceptable salt, ester or prodrug thereof have a formula of Formula II-c

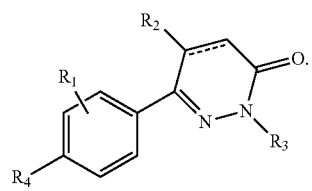

II-c

In some embodiments, the compounds, or a pharmaceutically acceptable salt, ester or prodrug thereof have a formula of Formula II-d

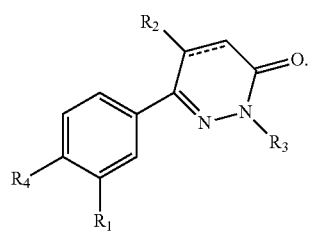

II-d

In some embodiments, the compounds, or a pharmaceutically acceptable salt, ester or prodrug thereof have a formula of Formula II-e or II-f

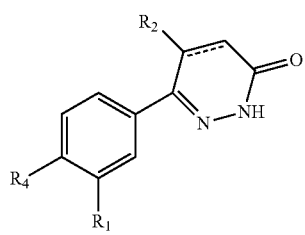

II-e

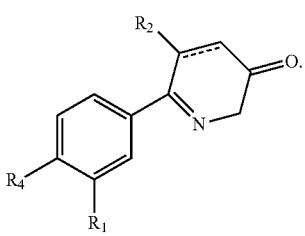

II-f

In some embodiments, a compound, or a pharmaceutically acceptable salt, ester or prodrug thereof having Formula II-i

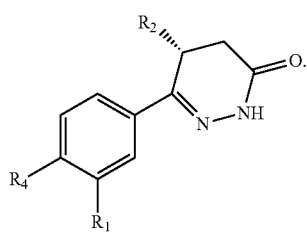

II-i is provided,
wherein
$R_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl;
$R_2$ is selected from an optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amino, cyano, or optionally substituted arylalkyl;
$R_4$ is halo, $OR_5$, $NR_5R_6$, $NR_5C(=O)R_6$, or

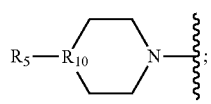

$R_5$ and $R_6$ are independently null, H, —OH, =O, halo, haloalkyl, alkyl, alkynyl, alkenyl, aryl, arylalkyl, heteroaryl, carbocycle, heterocycle, cyano, alkoxy, amino or, wherein $R_5$ and $R_6$ can be further substituted; and
$R_{10}$ is C, N, O, or S.

In some embodiments, the compound, or a pharmaceutically acceptable salt, ester or prodrug thereof, having Formula II-j

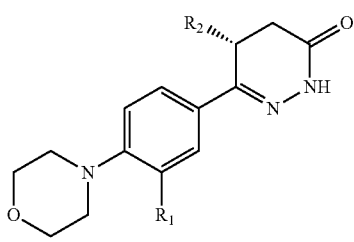

II-j is provided, wherein $R_2$ is $C_1$-$C_6$ alkyl and $R_1$ is halo. In some embodiments, $R_2$ is methyl.

In some embodiments, the compound or a pharmaceutically acceptable salt, ester or prodrug thereof, having a formula of:

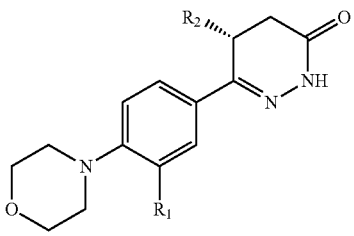

II-k is provided, wherein $R_2$ is methyl and $R_1$ is chloro or fluoro.

In some embodiments, the compound, or a pharmaceutically acceptable salt, ester or prodrug thereof, having Formula II-l

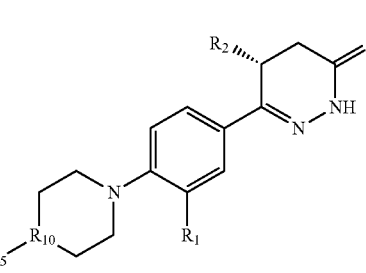

II-l is provided, wherein $R_1$ is H or halo; $R_2$ is $C_1$-$C_6$ alkyl; $R_5$ is H or $C_1$-$C_6$ alkyl; and $R_{10}$ is C or N. In some embodiments, $R_{10}$ is N. In some embodiments, $R_5$ is $C_1$-$C_6$ alkyl. In some embodiments, $R_1$ is H. In some embodiments, $R_2$ is methyl. In some embodiments, $R_{10}$ is C. In some embodiments, $R_5$ is H. In some embodiments, $R_2$ is methyl.

In some embodiments, a compound, or a pharmaceutically acceptable salt, ester or prodrug thereof, having Formula II-m,

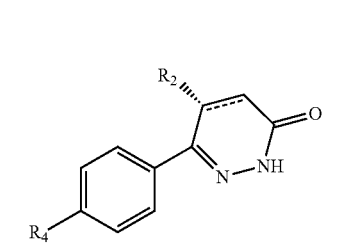

II-m is provided, wherein
$R_4$ is cycloalkyl, cycloalkenyl, heteroaryl, $C_1$-$C_6$ alkyl, or $C_3$-$C_6$ alkenyl and $R_2$ is provided as herein. In some embodiments, $R_2$ is $C_1$-$C_6$ alkyl. In some embodiments, $R_2$ is methyl. In some embodiments, $R_4$ is $C_5$-$C_7$ cycloalkyl. In some embodiments, $R_4$ is cyclohexanyl. In some embodiments, $R_4$ is $C_1$-$C_6$ alkyl. In some embodiments, $R_4$ is $C_3$-$C_6$ alkenyl. In some embodiments, $R_4$ is cyclohexenyl. In some embodiments, $R_4$ is $C_5$-$C_7$ cycloalkenyl. In some embodiments, $R_4$ is pyrimidyl.

In some embodiments, the compound is substantially optically pure. In some embodiments, a composition comprising a compound of II-m is substantially free or completely free of the other enantiomer.

In some embodiments, pharmaceutical compositions comprising a compound or a pharmaceutically acceptable salt, ester or prodrug thereof, described herein are provided.

In some embodiments, methods of treating cancer comprising administering to a subject with cancer a compound or a pharmaceutically acceptable salt, ester or prodrug thereof, described herein or a pharmaceutical composition described herein are provided.

DESCRIPTION OF EMBODIMENTS

Figure 1:
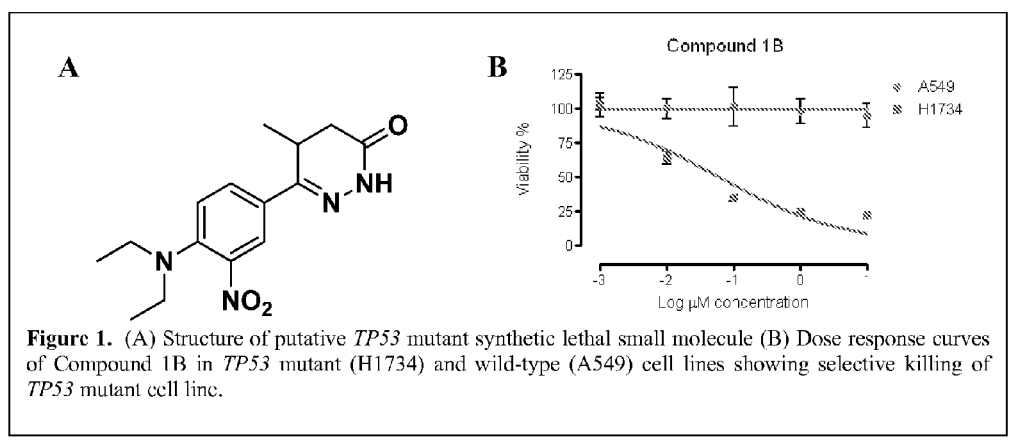
FIG. 1 shows a structure of one embodiments of the compounds described herein (A) that selectively targets cancer cells and shows dose response curves of the compound in TP53 mutant (H1734) and TP53 wild-type (A549) cell lines.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "acylamino" means an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a lower acyl group (e.g., —O—C(=O)—H or —O—C(=O)—C$_{1-6}$alkyl). An example of a lower acylamino is —NHC(=O)H or —NHC(=O)CH$_3$.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group. An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "animal" includes, but is not limited to, humans and non-human vertebrates such as wild, domestic, and farm animals.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:
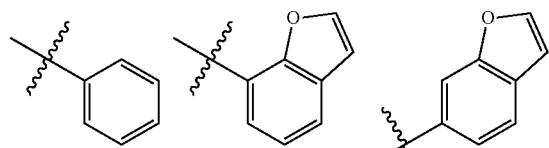
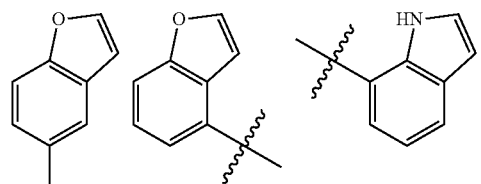
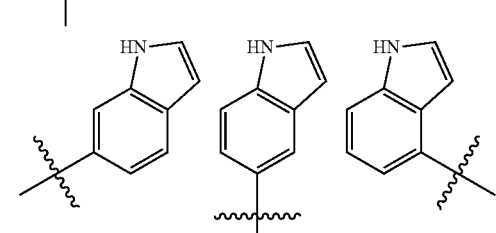
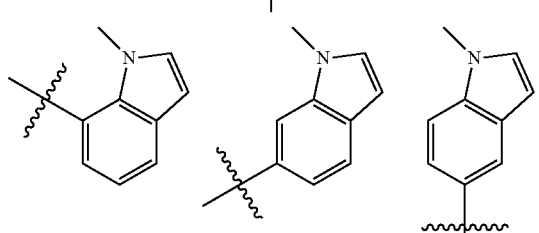
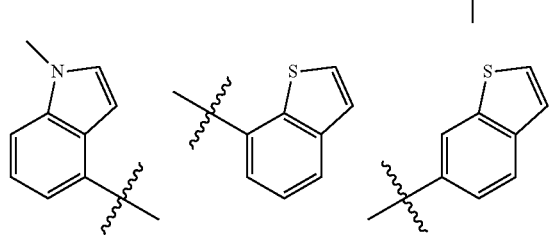
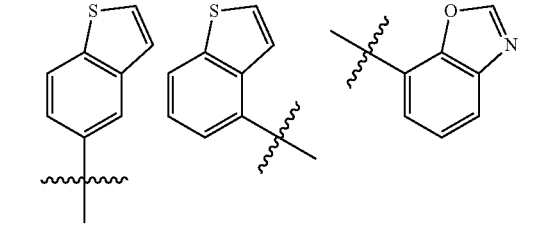
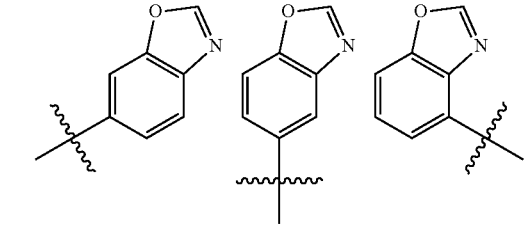
-continued
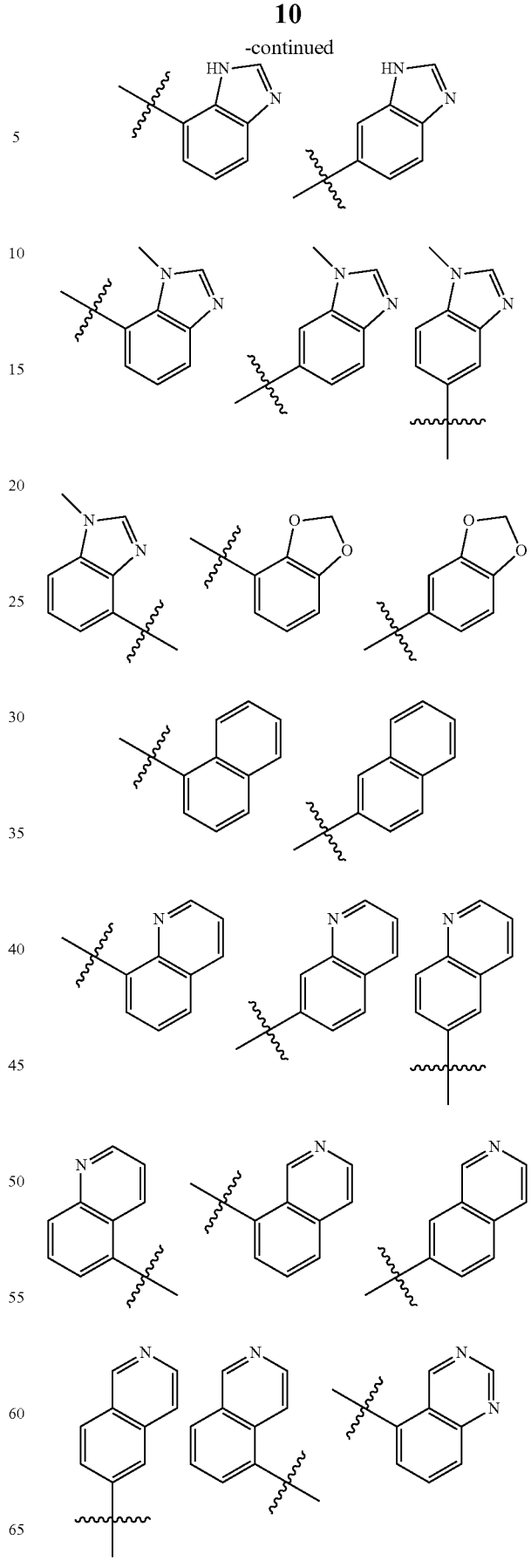

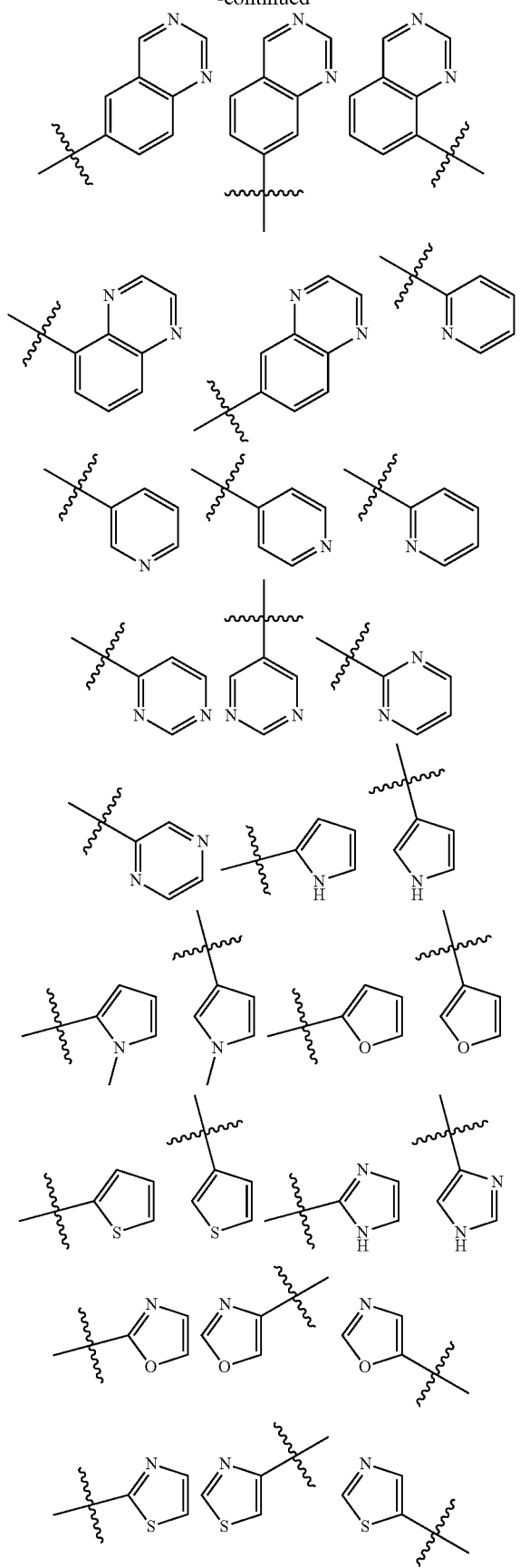
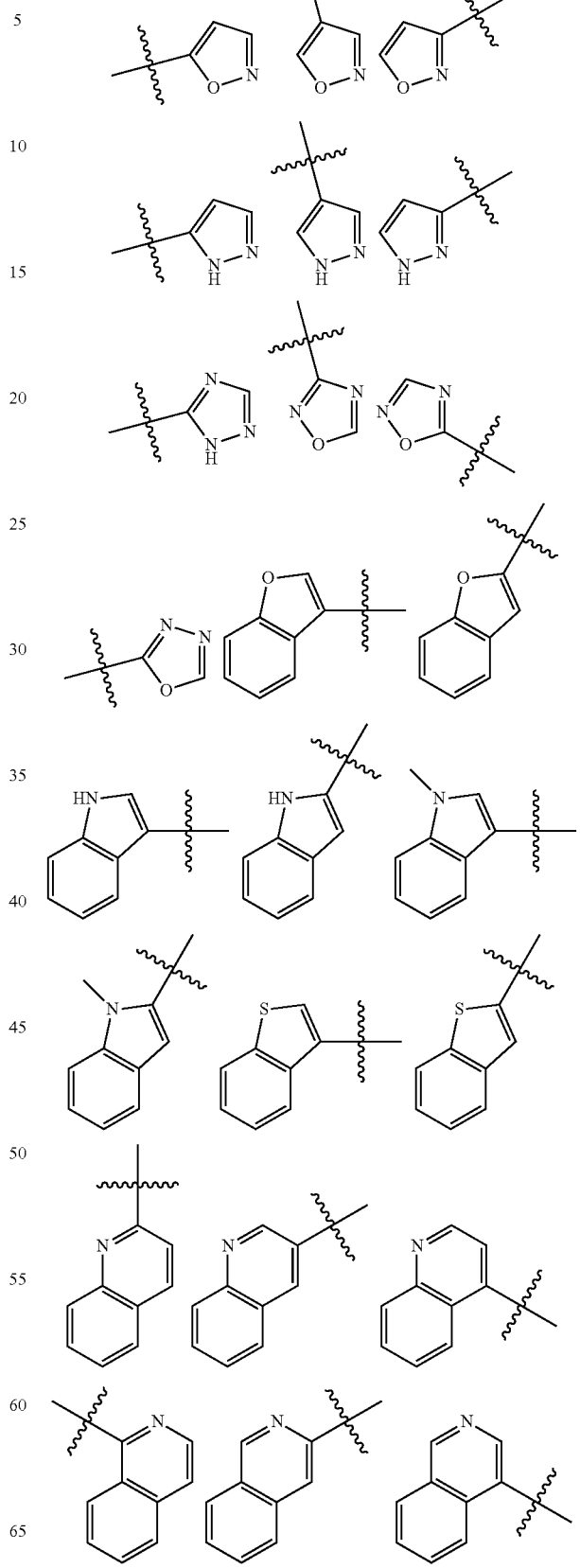

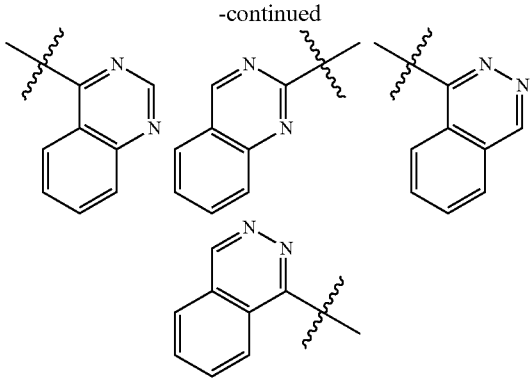

As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "cancer" means a spectrum of pathological symptoms associated with the initiation or progression, as well as metastasis, of malignant tumors.

As used herein, the term "carbamoyl" means —C(=O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CHF$_2$, CCl$_3$, CHCl$_2$, C$_2$Cl$_5$, CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$alkyl substituted by heterocycloalkyl.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophosphate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_8$alkyl), —N($C_1$-$C_8$alkyl)$_2$, —NH($C_6$aryl), —N($C_5$-$C_6$aryl)$_2$, —CHO, —CO($C_1$-$C_6$alkyl), —CO(($C_5$-$C_6$)aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of cancer" or "treating cancer" means an activity that prevents, alleviates or ameliorates any of the primary phenomena (initiation, progression, metastasis) or secondary symptoms associated with the cancer.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

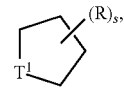

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present invention encompasses the use, where applicable, of stereoisomers, diastereomers and optical stereoisomers of the compounds of the invention, as well as mixtures thereof. Additionally, it is understood that stereoisomers, diastereomers, and optical stereoisomers of the compounds of the invention, and mixtures thereof, are within the scope of the invention. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, a compound of Formula I or a pharmaceutically acceptable salt, ester or prodrug thereof

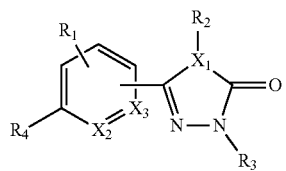

Formula I

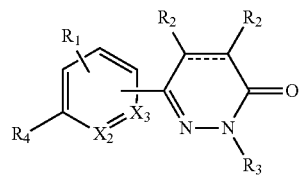

Formula II is provided wherein:

$X_1$ is $-A_1-A_2-A_3-A_4-$; $X_2$ is C or N; $X_3$ is C or N; $R_1$ is H, halo, optionally substituted alkyl, optionally substituted alkenyl, alkynyl, haloalkyl, optionally substituted aryl, optionally substituted heteroaryl, optionally substituted carbocycle, optionally substituted heterocycle, optionally substituted alkoxy, optionally substituted amine, cyano, or optionally substituted arylalkyl, $R_2$ is optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amine, cyano, or optionally substituted arylalkyl; $R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl; $R_4$ is $OR_5$, $NR_5R_6$, $NR_5C(=O)R_6$, or

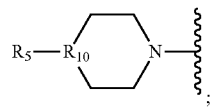

;

or $R_4$ and $R_1$ together with the atoms to which they are connected form an aryl, heteroaryl, heterocycle or carbocycle ring of 5-8 atoms, wherein:

$A_1$, $A_2$, $A_3$, and $A_4$ are independently carbon or null, wherein when two or more of $A_1$, $A_2$, $A_3$, and $A_4$ are carbons, the bonds between the carbons are optionally double bonds, wherein each $R_2$ connected to each of $A_1$, $A_2$, $A_3$, and $A_4$ is independent of one another;

$R_5$ and $R_6$ are independently null, H, —OH, =O, halo, haloalkyl, alkyl, alkynyl, alkenyl, aryl, arylalkyl, heteroaryl, carbocycle, heterocycle, cyano, alkoxy, amine, wherein $R_5$ and $R_6$ can be further substituted; and $R_{10}$ is C, N, O, or S.

In some embodiments, $R_4$ is

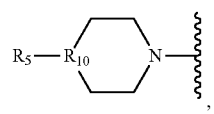

, wherein $R_{10}$ is S or O. In some embodiments, $R_{10}$ is S or O and $R_5$ is null.

In some embodiments, a compound or a pharmaceutically acceptable salt, ester or prodrug thereof having Formula II is provided wherein:

----- is an optional double bond;

$X_2$ is C or N, $X_3$ is C or N;

$R_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl;

each $R_2$ is independently selected from an optionally substituted $C_1$-$C_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amino, cyano, or optionally substituted arylalkyl;

$R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl;

$R_4$ is $OR_5$, $NR_5R_6$, $NR_5C(=O)R_6$, or

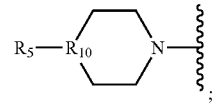

;

or $R_4$ and $R_1$ form a aryl, heteroaryl, heterocycle or carbocycle ring of 5-8 atoms fused to the atoms to which $R_4$ and $R_1$ are attached wherein:

$R_5$ and $R_6$ are independently null, H, —OH, =O, halo, haloalkyl, alkyl, alkynyl, alkenyl, aryl, arylalkyl, heteroaryl, carbocycle, heterocycle, cyano, alkoxy, amino or, wherein $R_5$ and $R_6$ can be further substituted;

$R_7$ and $R_8$ are independently null, H, —OH, =O, halo, haloalkyl, alkyl, alkynyl, alkenyl, aryl, arylalkyl, heteroaryl, carbocycle, heterocycle, cyano, alkoxy, amino or $R_7$ and $R_8$ form a ring with the N, such that the ring formed by $R_7$, $R_8$, and N is fused with the ring that the N is attached to, wherein $R_7$ and $R_8$ can be further substituted; and $R_{10}$ is N, O, or S.

In some embodiments, $R_4$ is

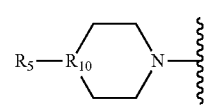

, wherein $R_{10}$ is S or O. In some embodiments, $R_{10}$ is S or O and $R_5$ is null.

In some embodiments, the compound of Formula I has a formula of Formula Ia:

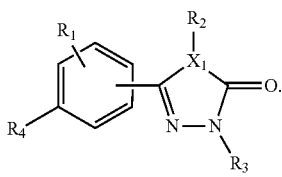

In some embodiments, the compound of Formula II has a Formula II-a:

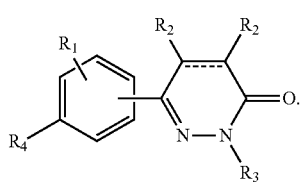

In some embodiments, a compound is provided wherein $R_1$ is H, $NH_2$, halo, $NO_2$, or $SO_2$.

In some embodiments, a compound is provided wherein $R_4$ is $-NH_2$, $-N((CH_2)_qCH_3)_2$, $-NH(CH_2)_qCH_3$, $-NHC(=O)(CH_2)_qCH_3$), or

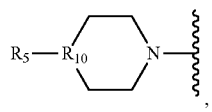

wherein q is 0-6. In some embodiments, $R_4$ is

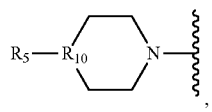

wherein $R_{10}$ is S or O. In some embodiments, $R_{10}$ is S or O and $R_5$ is null.

In some embodiments, a compound, pharmaceutically acceptable salt, ester or prodrug thereof having Formula III,

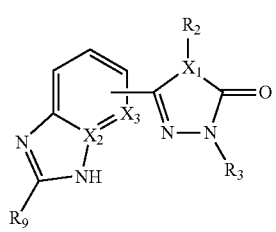

is provided wherein:
$X_1$ is $-A_1-A_2-A_3-A_4-$
$X_2$ is C or N,
$X_3$ is C or N
$R_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl, $R_2$ is optionally substituted $C_1$-$C_8$ alkyl, haloalkyl, optionally substituted aryl, optionally substituted heteroaryl, optionally substituted carbocycle, optionally substituted heterocycle, halo, H, $-OH$, optionally substituted alkoxy, optionally substituted amino, cyano, or optionally substituted arylalkyl, $R_3$ is an optionally substituted, saturated or unsaturated alkyl, optionally substituted aryl, optionally substituted heteroaryl, optionally substituted carbocycle, or optionally substituted heterocycle, H, halo, alkoxy, haloalkyl, optionally substituted alkoxy, cyano, optionally substituted arylalkyl, $R_9$ is optionally substituted $C_1$-$C_6$ alkyl wherein $A_1$, $A_2$, $A_3$, and $A_4$ are independently carbon or null, wherein when two or more of $A_1$, $A_2$, $A_3$, and $A_4$ are carbons, the bonds between the carbons are optionally double bonds, wherein each $R_2$ connected to each of $A_1$, $A_2$, $A_3$, and $A_4$ is independent of one another.

In some embodiments, a compound, pharmaceutically acceptable salt, ester or prodrug thereof are not of Formula III.

In some embodiments, the compound is substantially optically pure. In some embodiments, the compounds is at least 90, 91, 92, 93, 94, 95, 96, 97, 98, 99, or 99.5% optically pure.

In some embodiments, a compound, pharmaceutically acceptable salt, ester or prodrug of Formula I has Formula I-b

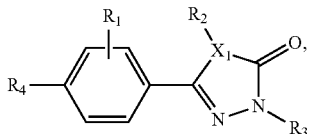

In some embodiments, a compound, pharmaceutically acceptable salt, ester or prodrug of Formula II has a structure of Formula II-b

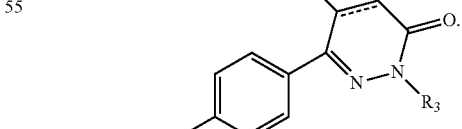

In some embodiments, $R_1$ is H and each $R_2$ is independently H or $C_1$-$C_6$ alkyl and $R_3$ and $R_4$ are as above. In some embodiments, a compound, pharmaceutically acceptable salt, ester or prodrug of Formula II has a structure of Formula II-c

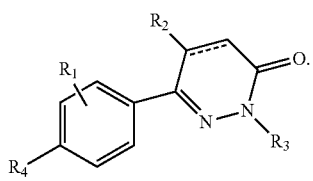
II-c

In some embodiments, $R_1$ is H, $NO_2$, $NH_2$, or halo and $R_2$ is $C_1$-$C_6$ alkyl and $R_3$ and $R_4$ are as above.

In some embodiments, a compound, pharmaceutically acceptable salt, ester or prodrug of Formula II has a structure of Formula II-d

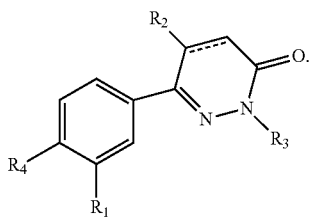
II-d

In some embodiments, $R_1$ is H, $NO_2$, $NH_2$, or halo and $R_2$ is $C_1$-$C_6$ alkyl and $R_3$ and $R_4$ are as above.

In some embodiments, a compound, pharmaceutically acceptable salt, ester or prodrug of Formula II has a structure of Formula II-e or II-f

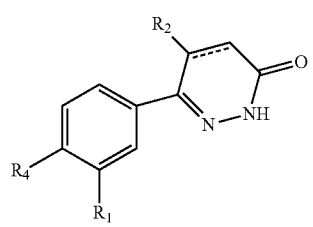
II-e

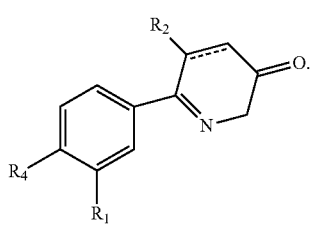
II-f

In some embodiments, $R_1$ is H, alkylamino, $NO_2$, $NH_2$, or halo and $R_2$ is $C_1$-$C_6$ alkyl and $R_4$ is as above.

In some embodiments, the compound, comprising a compound, prodrug, or pharmaceutically salt thereof, is a compound selected from the group consisting of:

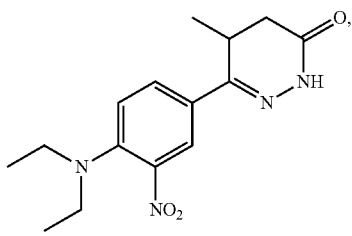

-continued

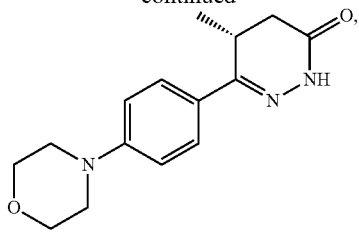

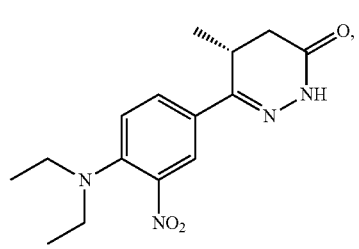

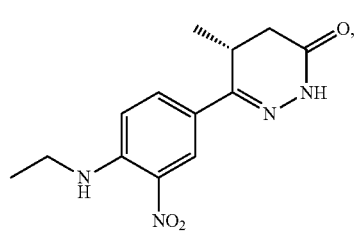

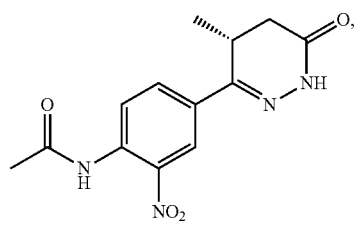

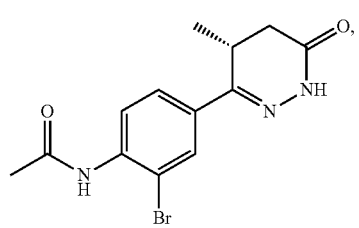

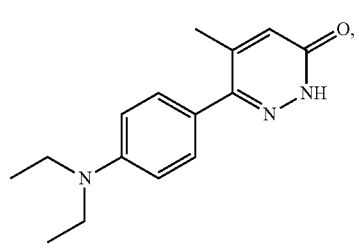

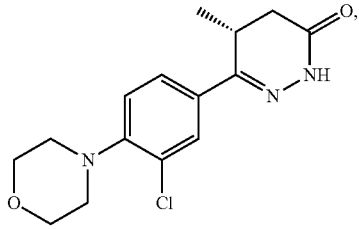

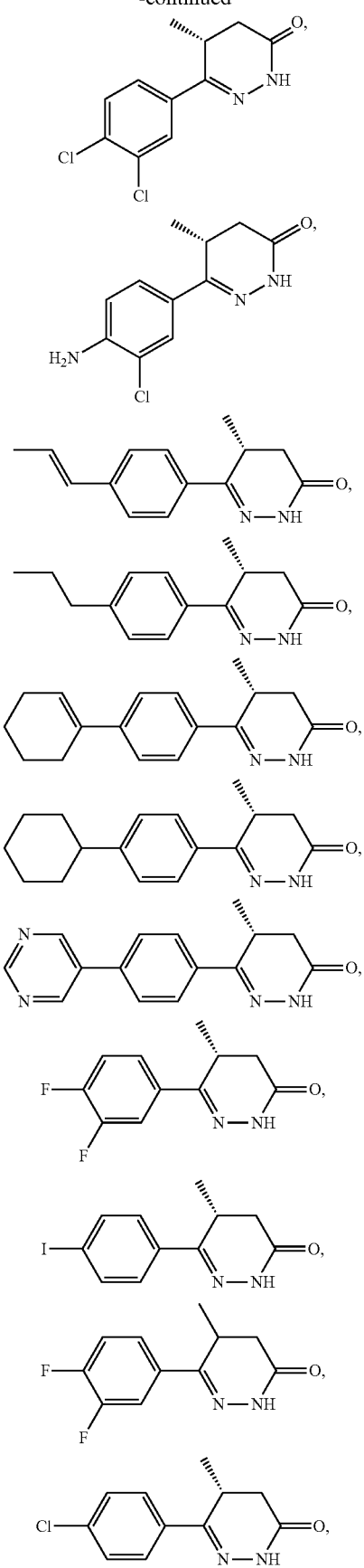
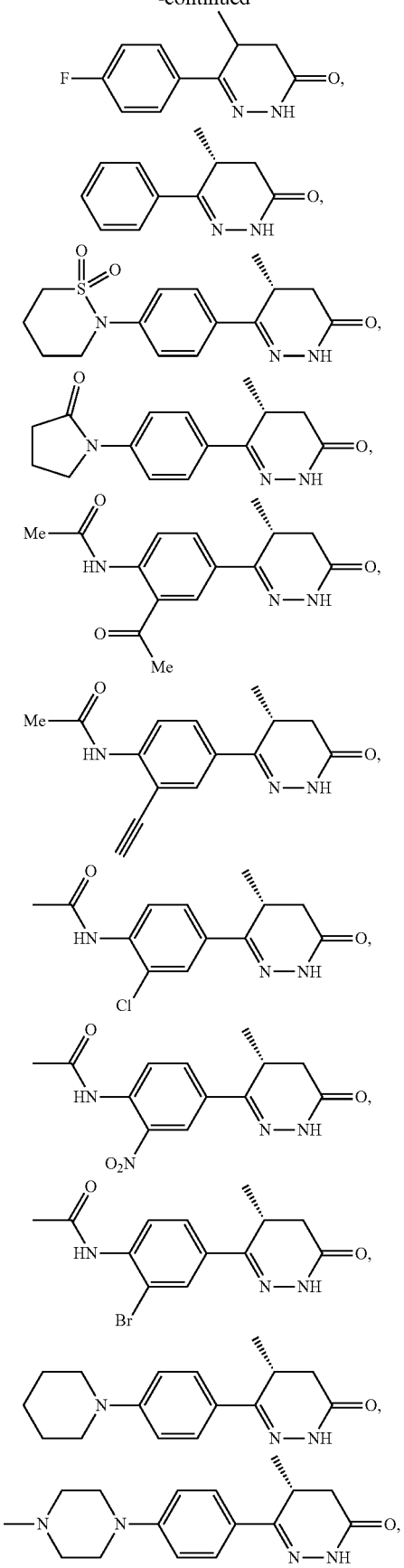

-continued

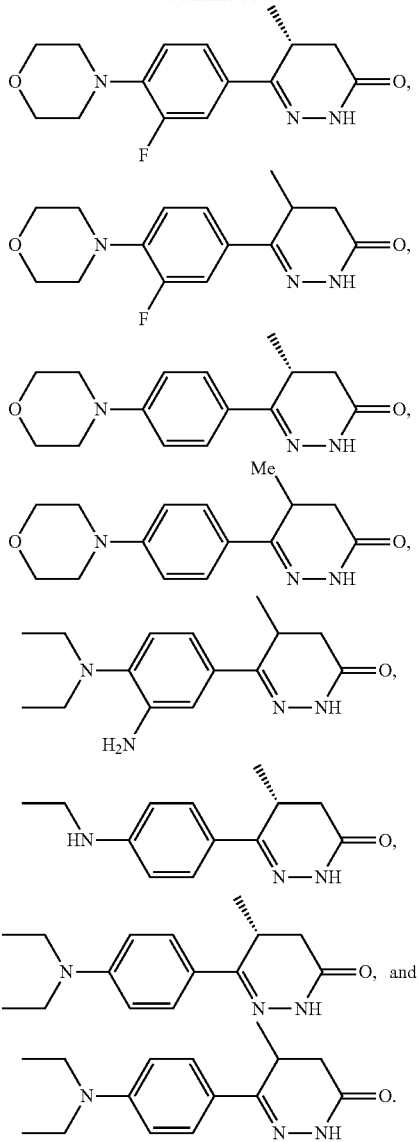

In some embodiments, the compound is

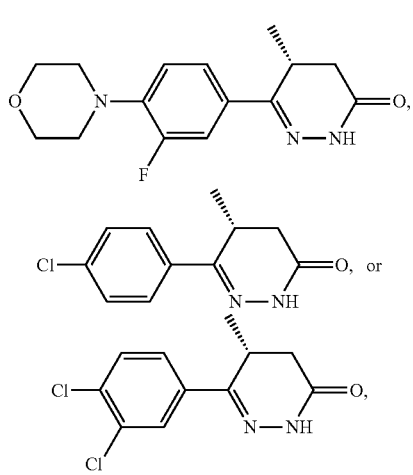

or a prodrug, or pharmaceutically salt thereof.

In some embodiments, a compound, or a pharmaceutically acceptable salt, ester or prodrug thereof having Formula II-i II-i

[Structure of Formula II-i]

is provided,
wherein
R$_1$ is optionally substituted alkyl, optionally substituted alkenyl, alkynyl haloalkyl, optionally substituted aryl, optionally substituted heteroaryl, optionally substituted carbocycle, optionally substituted heterocycle, halo, H, optionally substituted alkoxy, optionally substituted amine, cyano, or optionally substituted arylalkyl;
R$_2$ is selected from an optionally substituted C$_1$-C$_8$ alkyl, haloalkyl, optionally substituted aryl, optionally substituted heteroaryl, optionally substituted carbocycle, optionally substituted heterocycle, halo, H, —OH, optionally substituted alkoxy, optionally substituted amino, cyano, or optionally substituted arylalkyl;
R$_4$ is halo, OR$_5$, NR$_5$R$_6$, NR$_5$C(=O)R$_6$, or

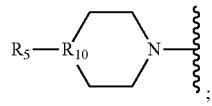

;

R$_5$ and R$_6$ are independently null, H, —OH, =O, halo, haloalkyl, alkyl, alkynyl, alkenyl, aryl, arylalkyl, heteroaryl, carbocycle, heterocycle, cyano, alkoxy, amino or, wherein R$_5$ and R$_6$ can be further substituted; and
R$_{10}$ is C, N, O, or S.

In some embodiments, R$_1$ is H, halo or NR$_5$R$_6$ and R4 is H, halo or N$_R$5R$_6$. In some embodiments, R$_1$ is halo and R$_4$ is H or NR$_5$R$_6$. In some embodiments, R$_1$ is halo and R$_4$ is NH$_2$. In some embodiments, R$_4$ is halo and R$_1$ is H. In some embodiments, R$_4$ is chloro, flouro, or iodo. In some embodiments, R$_1$ is chloro or flouro.

In some embodiments, R$_1$ and R$_4$ are halo. In some embodiments, R$_1$ and R$_4$ are iodo, flouro or chloro.

In some embodiments, R$_2$ is C$_1$-C$_8$ alkyl. In some embodiments, R$_2$ is methyl.

In some embodiments, the compound, or a pharmaceutically acceptable salt, ester or prodrug thereof, having Formula II-j II-j

[Structure of Formula II-j]

is provided, wherein R$_2$ is C$_1$-C$_6$ alkyl and R$_1$ is halo.

In some embodiments, the compound or a pharmaceutically acceptable salt, ester or prodrug thereof, having a formula of:

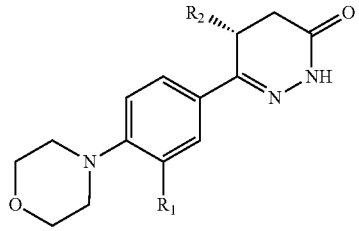

II-k is provided, wherein $R_2$ is methyl and $R_1$ is chloro or fluoro.

In some embodiments, the compound, or a pharmaceutically acceptable salt, ester or prodrug thereof, having Formula II-l

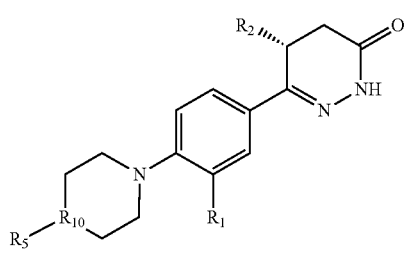

II-l is provided, wherein
wherein
$R_1$ is H or halo;
$R_2$ is $C_1$-$C_6$ alkyl;
$R_5$ is H or $C_1$-$C_6$ alkyl; and
$R_{10}$ is C or N.

In some embodiments, $R_{10}$ is N. In some embodiments, $R_5$ is $C_1$-$C_6$ alkyl. In some embodiments, $R_1$ is H. In some embodiments, $R_2$ is methyl.

In some embodiments, $R_{10}$ is C. In some embodiments, $R_5$ is H. In some embodiments, $R_2$ is methyl.

In some embodiments, a compound, or a pharmaceutically acceptable salt, ester or prodrug thereof, having Formula II-m,

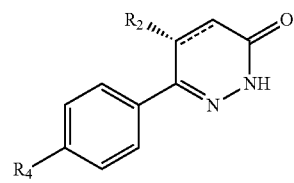

II-m is provided, wherein
$R_4$ is cycloalkyl, cycloalkenyl, heteroaryl, $C_1$-$C_6$ alkyl, or $C_3$-$C_6$ alkenyl and $R_2$ is provided as herein. In some embodiments, $R_2$ is $C_1$-$C_6$ alkyl. In some embodiments, $R_2$ is methyl. In some embodiments, $R_4$ is $C_5$-$C_7$ cycloalkyl. In some embodiments, $R_4$ is cyclohexanyl. In some embodiments, $R_4$ is $C_1$-$C_6$ alkyl. In some embodiments, $R_4$ is $C_3$-$C_6$ alkenyl. In some embodiments, $R_4$ is cyclohexenyl. In some embodiments, $R_4$ is $C_5$-$C_7$ cycloalkenyl. In some embodiments, $R_4$ is pyrimidyl.

In some embodiments, the compound of a formula above is

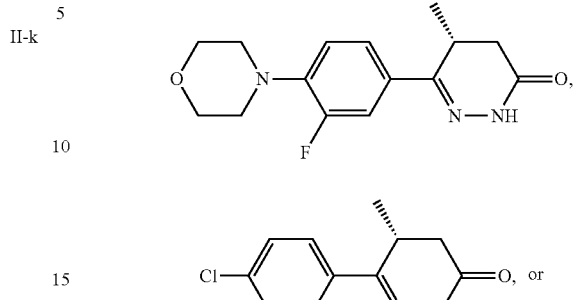

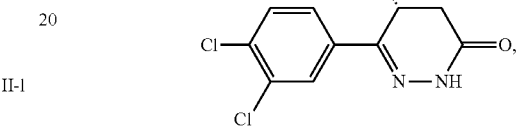

or a prodrug, or pharmaceutically salt thereof.

In some embodiments, the present invention provides pharmaceutical compositions comprising a compound, prodrug, or pharmaceutically salt thereof of any compound described herein.

The compounds described herein can be made by can be made according to the methods described herein and in the examples. The methods described herein can be adapted based upon the compounds desired and described herein. In some embodiments, the method is made according to the following schemes. In some embodiments, this method can be used to make one or more compounds as described herein and will be apparent to one of skill in the art which compounds can be made according to the methods described herein.

The following representative schemes illustrate how compounds described herein can be prepared. The specific solvents and reaction conditions referred to are also illustrative and are not intended to be limited. Compounds not described are either commercially available or are readily prepared by one skilled in the art using available starting materials.

The conditions and temperatures can be varied, such as shown in the examples described herein. These schemes are non-limiting synthetic schemes and the synthetic routes can be modified as would be apparent to one of skill in the art reading the present specification.

In some embodiments, the following scheme is used to prepare one or more compounds:

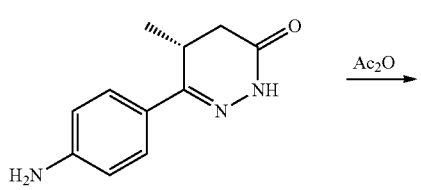

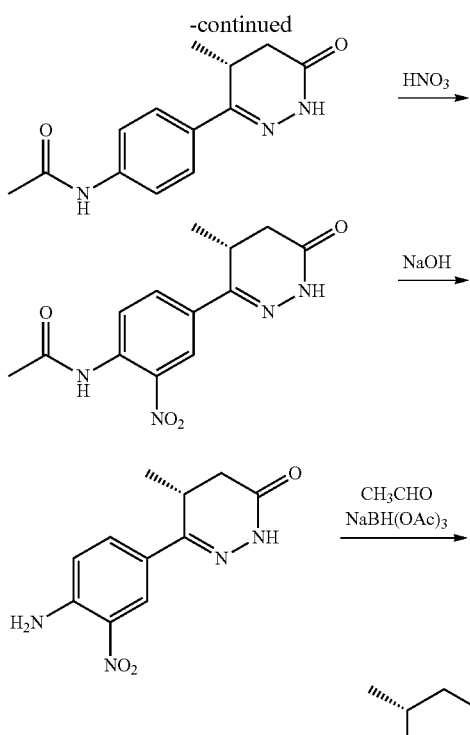

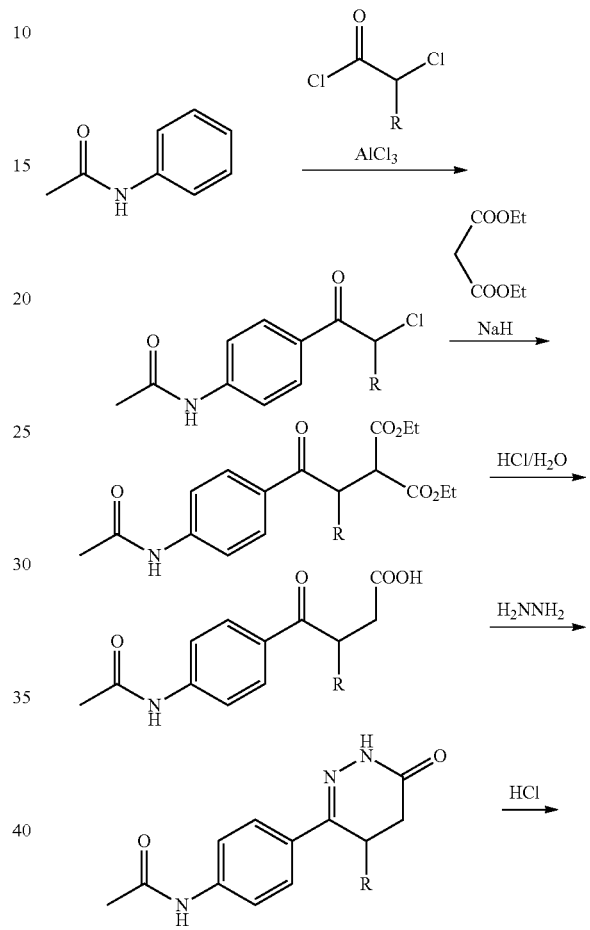

Pyridazone synthesis can start with phenyl acetamides which undergo Friedel Crafts acylations with α-chloro acid chlorides (see, *J. Heterocyclic Chem.* 1988, 25, 1689-95, which is hereby incorporated by reference). The compounds can then be modified by chloride displacement with malonate anion followed by ester hydrolysis, decarboxylation, and hydrazine condensation to yield the substituted 6-(4-acetamidophenyl)tetrahydropyridazones.

In some embodiments, the compounds are synthesized according to the following schemes, wherein R represents the substituents as defined herein. In some embodiments, compound synthesis starts with amino-substituted aryl pyrazolones and pyridazones. Pyrazolone synthesis can begin with a substituted 3-aryl 3-oxopropanoate ester which can be alkylated with one or two groups before addition of hydrazine to give 4-substituted-3-(4-nitrophenyl)-1H-pyrazol-5 (4H). This can be reduced to the amino derivative.

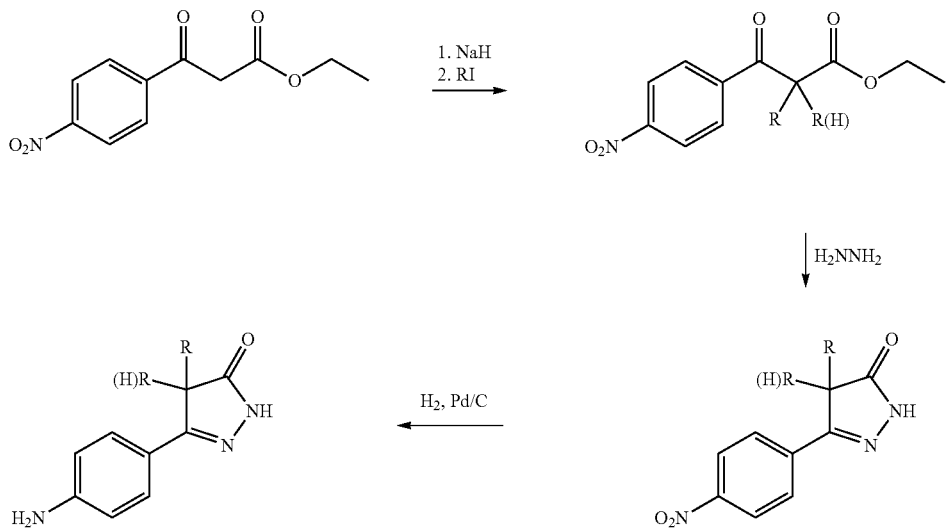

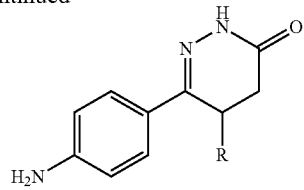

Amino and acetamido-phenyl compounds can be functionalized further using standard chemistry as depicted in the scheme below for the pyridazone compounds. Phenyl acetamides can be functionalized via bromination for further carbon-carbon bond forming reactions. Nitration can be followed by reduction to the amine and diazatization, which allows for further substitutions.

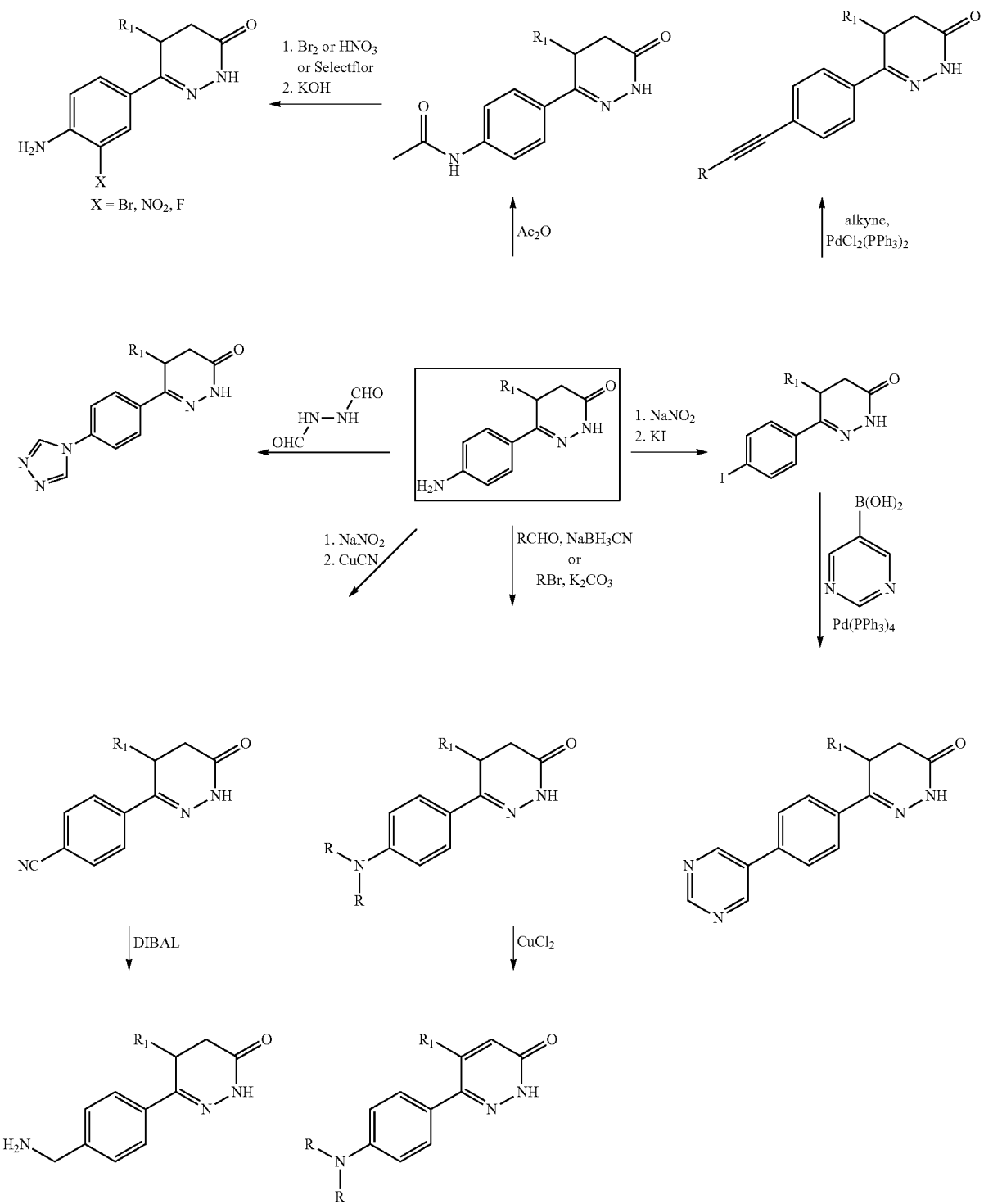

Iodo- and bromo-arenes, formed via diazonium chemistry from the corresponding amines, can be used in palladium catalyzed reactions to form new carbon-carbon bonds, and heterocycles can be introduced using Buchwald chemistry. Heterocycles such as triazoles can be formed by condensation reactions of the amines Reductive alkylation or alkylation can be used to make more substituted amines Homologated amines can be similarly formed via cyanide displacement of the diazonium salt followed by reduction. Unsaturation can be introduced by $CuCl_2$.

In some embodiments, fluoro-amino substituted compounds can be made according to the following scheme:

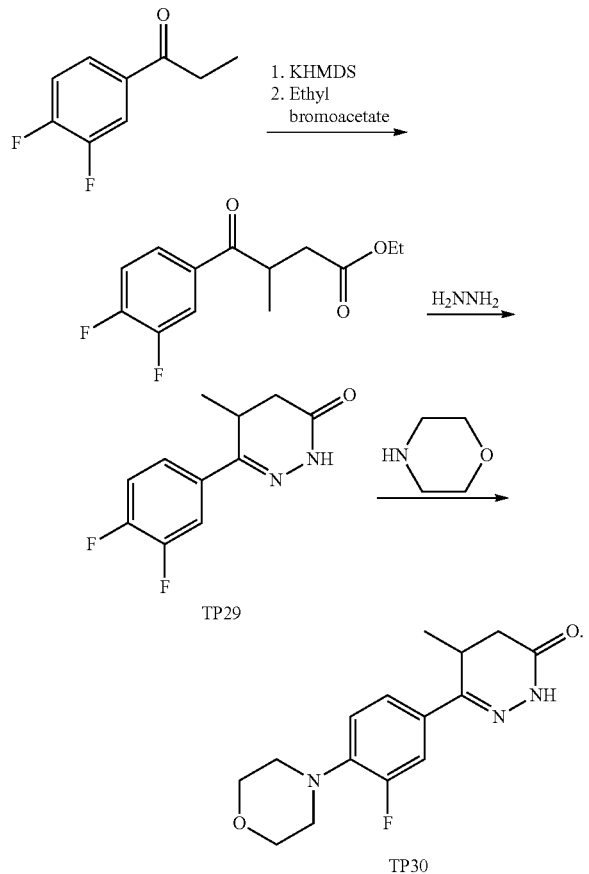

The scheme can be modified to change the substituents according to well-known methods.

Chlorinated amides can be prepared according to the following scheme:

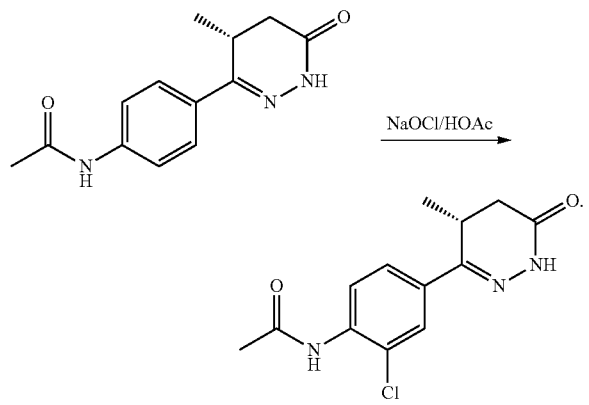

The scheme can be modified to change the substituents according to well-known methods.

In some embodiments, the compounds are made according to the following scheme:

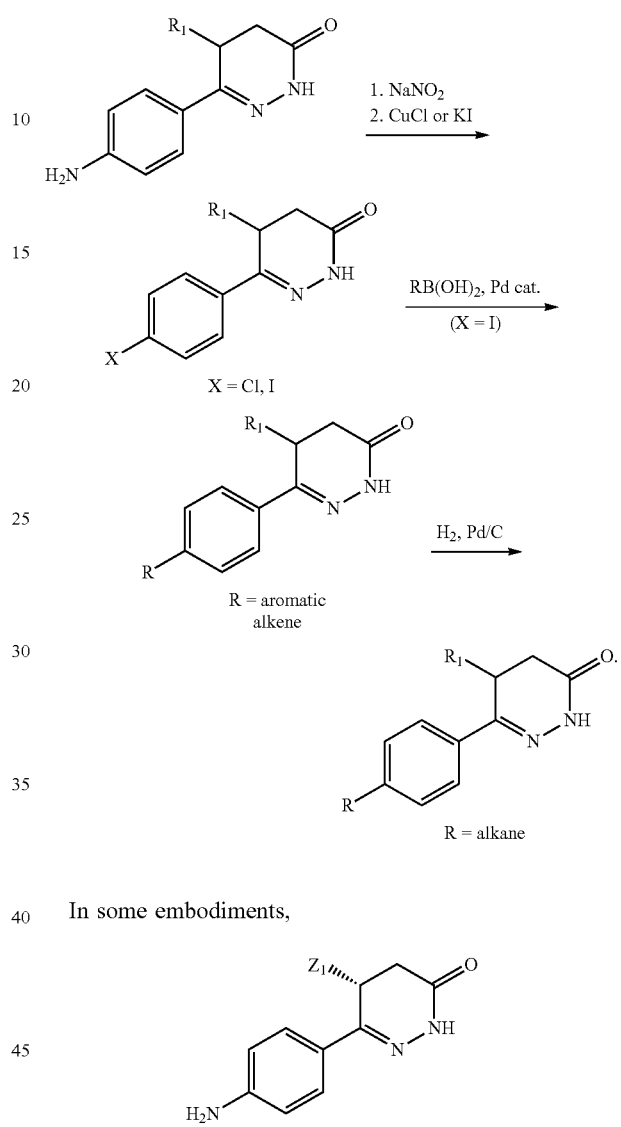

In some embodiments, is reacted under conditions sufficient to produce wherein $Z_1$ is $C_1$-$C_6$ alkyl and X is chloro or iodo. In some embodiments, $Z_1$ is methyl. In some embodiments, the product produced according to the scheme is at least 99 or 100% optically pure.

In some embodiments, the compounds are made according to the following scheme:

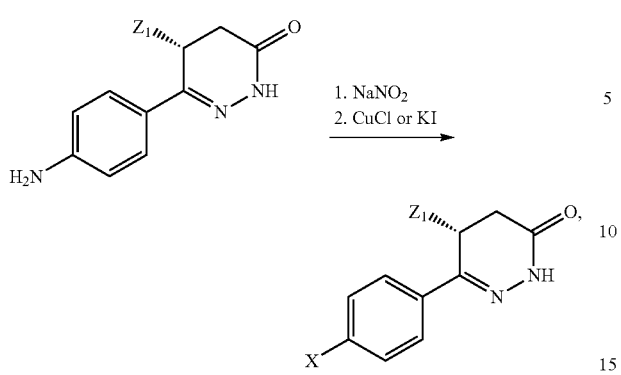

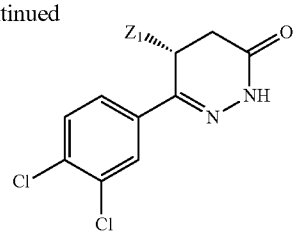

wherein $Z_1$ is $C_1$-$C_6$ alkyl. In some embodiments, $Z_1$ is methyl. In some embodiments, the starting material is at least 95, 96, 97, 98, 99% or 100% optically pure. In some embodiments, the product produced according to the scheme is at least 95, 96, 97, 98, 99% or 100% optically pure.

In some embodiments, the compounds are made according to the following scheme:

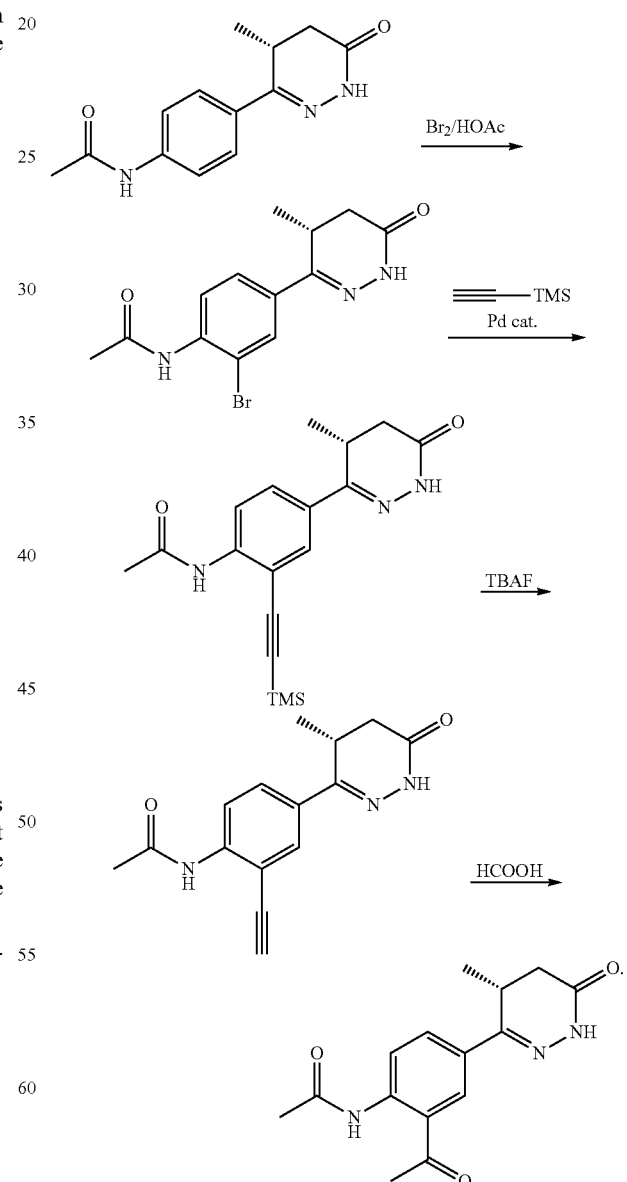

wherein $Z_1$ is $C_1$-$C_6$ alkyl and X is chloro or iodo. In some embodiments, $Z_1$ is methyl. In some embodiments, the starting material is at least 99% or 100% optically pure. In some embodiments, the product produced according to the scheme is at least 99 or 100% optically pure.

In some embodiments,

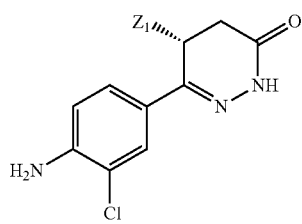

is reacted under condition sufficient to produce

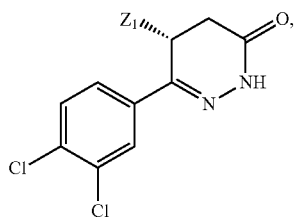

wherein $Z_1$ is $C_1$-$C_6$ alkyl. In some embodiments, $Z_1$ is methyl. In some embodiments, the starting material is at least 95, 96, 97, 98, 99% or 100% optically pure. In some embodiments, the product produced according to the scheme is at least 95, 96, 97, 98, 99% or 100% optically pure.

In some embodiments, the compounds are made according to the following scheme:

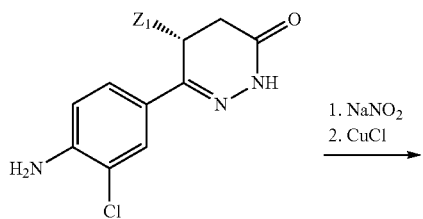

In some embodiments, the compounds are made according to the following scheme:

41 42

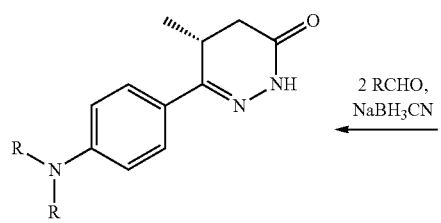
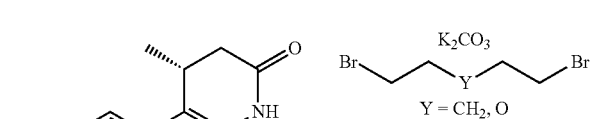

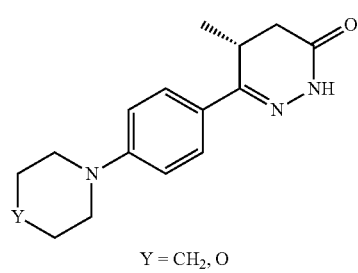

Y = CH₂, O

The compounds can also be prepared according to the embodiments described in the Examples. The examples can also be readily modified to yield other compounds described herein.

In some embodiments, the compounds can be represented according to the following non-limiting exemplary formulae:

Active compounds                           Generic Structures

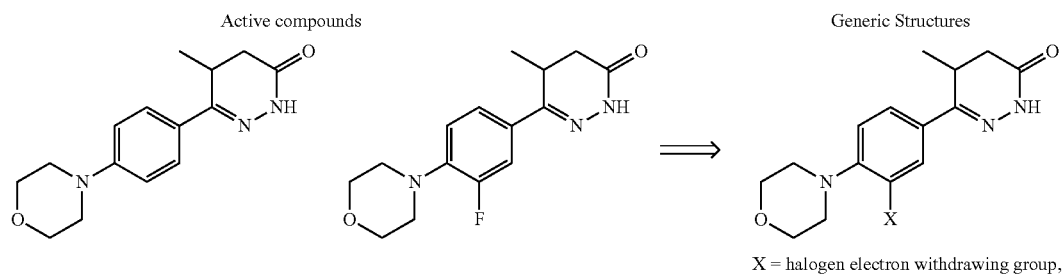

X = halogen electron withdrawing group,

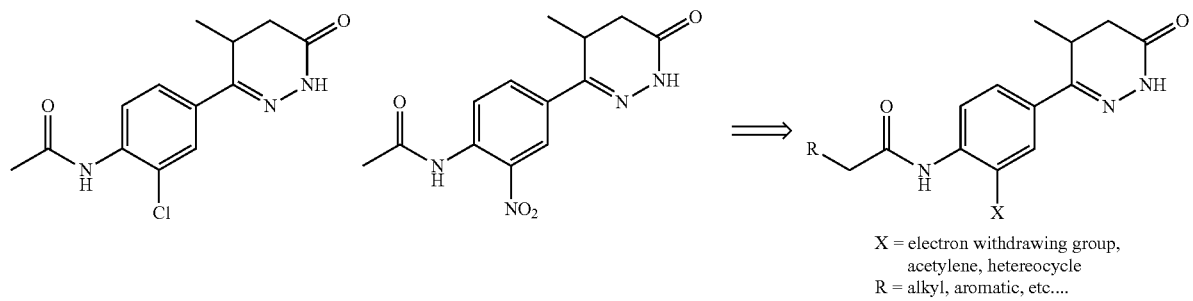

X = electron withdrawing group, acetylene, heterocycle
R = alkyl, aromatic, etc....

-continued

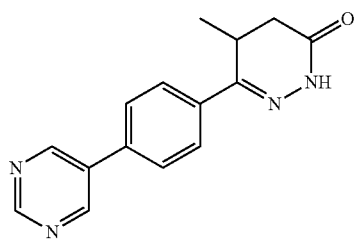

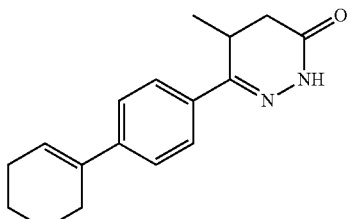

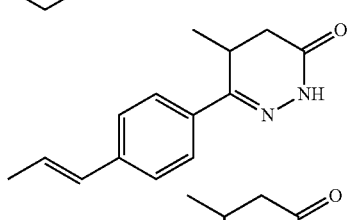

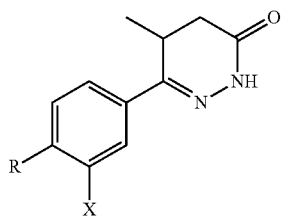

X = electron withdrawing group, acetylene, hetereocycle
R = alkyl, alkenyl, aromatic, heteroaromatic

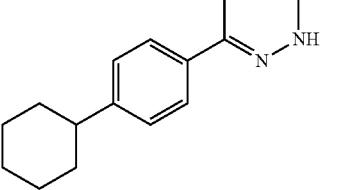

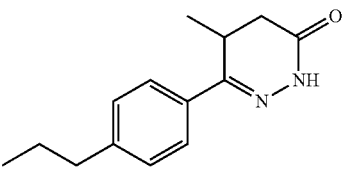

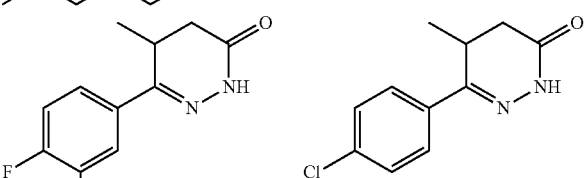

X, Y = F, Cl, electron withdrawing group

In addition to the active compounds listed above, other compounds disclosed herein are also active and can be used to treat cancer. In some embodiments, the stereochemistry around the methyl group (or other type of alkyl group) shown is the R-stereochemistry.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other analgesics, antidepressants, anti-anxiety compounds, anti-overactive bladder compounds, compounds for the treatment of Parkinsons, and the like. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present invention is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. No. 3,863,633; U.S. Pat. No. 3,867,519; U.S. Pat. No. 3,868,445; U.S. Pat. No. 3,960,150; U.S. Pat. No. 3,963,025; U.S. Pat. No. 4,186,184; U.S. Pat. No. 4,303,637; U.S. Pat. No. 5,443,505; and U.S. Pat. No. 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquarternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions of the invention in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present invention also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The present invention also provides methods of treating cancer in a subject comprising administering to the subject one or more compounds described herein or a salt thereof, or a pharmaceutical composition of the same. In some embodiments, the subject is a subject in need of such treatment. In some embodiments, the compound is administered as a prodrug. Examples of cancer include, but are not limited to, melanoma, endometrium, lung, hematopoietic/lymphoid, ovarian, cervical, soft-tissue sarcoma, urinary tract, pancreas, thyroid, kidney, glioblastoma, breast cancer. In some embodiments, the cancer is not a B-cell proliferative type cancer. In some embodiments, the cancer is not multiple myeloma.

Also provided herein are methods of treating cancer comprising administering to a subject, which includes a subject in need thereof, with cancer a compound or a pharmaceutically acceptable salt, ester or prodrug thereof, of a PDE inhibitor. In some embodiments, the PDE inhibitor is a PDE3 inhibitor. In some embodiments, the PDE inhibitor is zardaverine, anagrelide, imazodan, or quazinone, or any combination thereof. In some embodiments, the cancer is melanoma, endometrium, lung, hematopoietic/lymphoid, ovarian, cervical, soft-tissue sarcoma, urinary tract, pancreas, thyroid, kidney, glioblastoma, breast cancer. In some embodiments, the cancer is not a B-cell proliferative type cancer. In some embodiments, the cancer is not multiple myeloma.

The present invention also provides one or more compounds described above, or a pharmaceutically acceptable salt thereof, or a pharmaceutical composition comprising one or more compounds described above, for the treatment of cancer in a subject. In some embodiments, the compounds are for the treatment of cancer in a mammal in need thereof.

The present invention also provides one or more compounds described above, or a pharmaceutically acceptable salt thereof, or a pharmaceutical composition comprising one or more compounds described above, for use in the manufacture of a medicament for the treatment of cancer.

Any other known medicament, compound, or composition use for the treatment of cancer can be used in co-therapy, co-administration or co-formulation with a composition or compound as described herein.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%). Ideally the concentration remains above the $EC_{50}$ for at least 100% of the dosing interval. Where this is not achievable it is desired that the concentration should remain above the $EC_{50}$ for at least about 60% of the dosing interval, or should remain above the $EC_{50}$ for at least about 40% of the dosing interval.

The disclosures of each and every patent, patent application, publication, and accession number cited herein are hereby incorporated herein by reference in their entirety.

In order that the embodiments disclosed herein may be more efficiently understood, examples are provided below. It should be understood that these examples are for illustrative purposes only and are not to be construed as limiting in any manner.

EXAMPLES

Example 1: Identification of a Compound that Selectively Targets Cancer Cells

Compounds were screened against two lung-adeno cancer cell lines: NCI-H1734 cells, which harbor a homozygous TP53 R273L mutation, and A549 cells, expressing wild-type TP53. The screen identified a compound that preferentially killed the TP53 mutant NCI-H1734 cell line with an IC50 of 60 nM (see, FIG. 1).

Example 2: Separation of Enantiomers Show Differences in Activity

The racemate of

Figure 2:
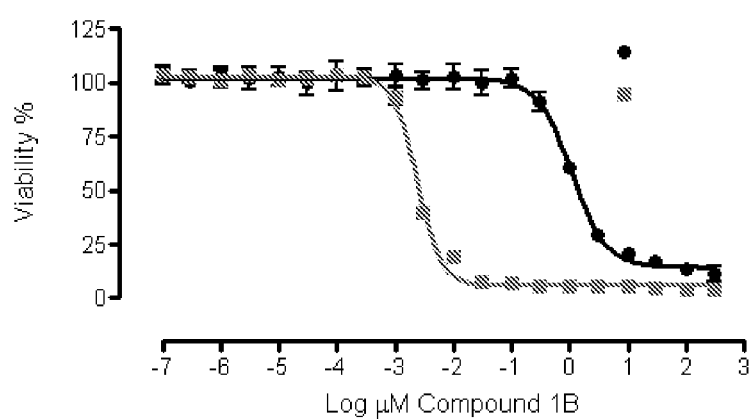
FIG. 2 shows that enantiomer separation resulted in a 500-fold difference in $EC_{50}$ between the two optically pure compounds in HeLa cells.

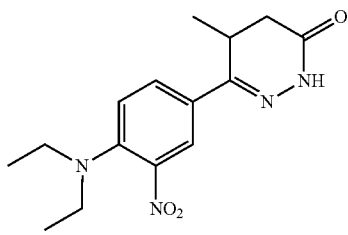

was separated into its enantiomers via chiral SFC chromatography and tested in Hela cells. The data indicates that one of the enantiomer (filled squares), is 500-fold more active than the other (filled circles), which is shown in FIG. 2.

Example 3: Compounds Kill Cells by Inducing Apoptosis

Figure 3:
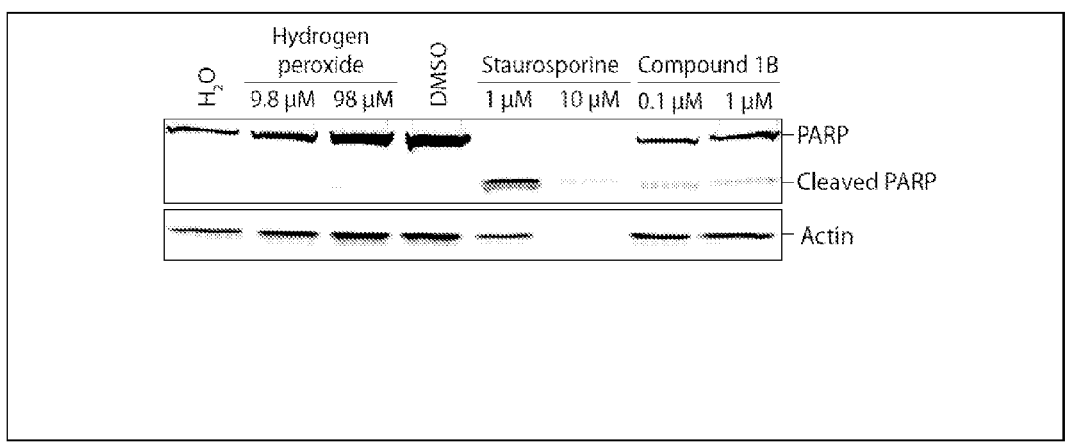
FIG. 3 shows a PARP cleavage assay of cells treated with the compound described in Example 1.

The mechanism of cell death was determined after contacting the cells with the compound in Example 1. The data indicates that an apoptotic mechanism, as measured by PARP cleavage, is activated. (see, FIG. 3). Hela cells (p53 inactivated by papillomavirus E6 expression) treated with the compound in Example 1 caused PARP cleavage similarly to positive control treatment staurosporine. Treatment with 10 µM staurosporine resulted in almost complete cell death. Negative control treatment hydrogen peroxide caused necrosis but not apoptosis. Cells were treated for 24 h with the indicated concentrations of each agent, lysed, and immunoblotted with anti-PARP or anti-actin.

Example 4: Compounds Treat Cancer In Vivo

Subcutaneous xenograft efficacy experiments are prepared in nude mice. Nude mice are implanted with NCI-H2122 cells and the effect of the compounds is examined 5 million cells are injected at 3 sites on 10 mice for each compound and the injection sites monitored until the tumor volume approaches 100 mL³. The tumor size is expected to shrink after being treated with an active compound.

Example 5: Synthesis of

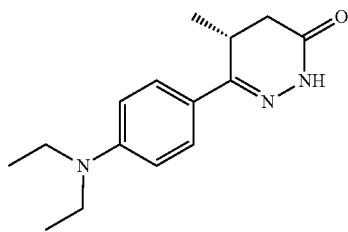 [SMILES: CCN(CC)c1ccc(C2=NNC(=O)C[C@H]2C)cc1]

To 200 mg (0.984 mmol) of (R)-6-(4-aminophenyl)-5-methyl-4,5-dihydropyridazin-3(2H)-one (purchased from Waterstone) dissolved in 5 mL of MeOH was added 87 mg of acetaldehyde (2.0 mmol), 113 uL of HOAc (2.0 mmol) and 124 mg (2.0 mmol) of NaBH$_3$CN and the reaction was stirred overnight at room temperature. The next day more reagents were added and the reaction stirred another 24 h. The mixture was concentrated and partitioned between CH$_2$Cl$_2$ and water, the CH$_2$Cl$_2$ was separated, dried, and concentrated before chromatography with 20-40% EtOAc in hexane to isolate 210 mg of product as a white solid (82%). $^1$H NMR (300 MHz, CDCl$_3$) δ 8.95 (s, 1H), 7.64 (d, J=8.7, 2H), 6.66 (d, J=8.7, 2H), 3.37 (dd, J=9.6, 16.4, 5H), 2.67 (dd, J=6.5, 16.8, 1H), 2.43 (d, J=16.8, 1H), 1.41-1.02 (m, 10H). $^{13}$C NMR (75 MHz, CDCl3) δ 166.82, 154.55, 148.79, 127.32, 120.81, 111.08, 77.42, 77.00, 76.58, 44.32, 33.92, 27.74, 16.37, 12.50. MS: 260 (M+1).

Example 6: Synthesis of

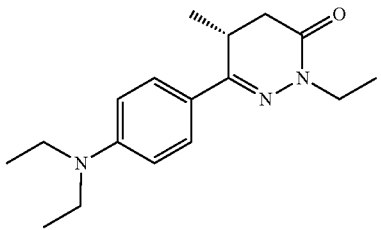

To 40 mg (0.15 mmol) of the compound prepared in Example 5 dissolved in 0.5 mL DMF was added 6.0 mg of an 60% oil dispersion of NaH (0.15 mmol) and a precipitate appeared which dissolved upon the addition of 20 uL of ethyl iodide. After 30 min, EtOAc and water were added, the EtOAc was dried, concentrated and chromatographed with 25% EtOAc in hexane to yield 27 mg of product as an oil which solidified with time (61%). $^1$H NMR (300 MHz, CDCl$_3$) δ 7.66 (d, J=9.1, 2H), 6.67 (d, J=9.1, 2H), 3.98 (dq, J=7.1, 14.2, 1H), 3.81 (dq, J=7.1, 14.1, 1H), 3.40 (q, J=7.0, 4H), 3.33-3.12 (m, 1H), 2.62 (dd, J=6.6, 16.5, 1H), 2.41 (dd, J=1.5, 16.5, 1H), 1.25 (t, J=7.1, 3H), 1.19 (t, J=6.9, 9H). $^{13}$C NMR (75 MHz, CDCl$_3$) δ 164.09, 154.65, 148.71, 127.29, 121.14, 111.11, 44.37, 43.13, 34.69, 27.95, 16.27, 13.14, 12.52. MS: 288 (M+1).

Example 7: Preparation of

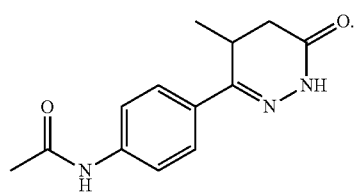 [SMILES: CC(=O)Nc1ccc(C2=NNC(=O)CC2C)cc1]

2.00 g (9.84 mmol) of (R)-6-(4-aminophenyl)-5-methyl-4,5-dihydropyridazin-3(2H)-one (Waterstone) was stirred 1 h in 5 mL of acetic anhydride before addition of 30 mL water, filtration, rinsing the solids with water and drying to yield 2.20 g of product (91%) $^1$H NMR (300 MHz, DMSO-d$_6$) δ 10.92 (s, 1H), 10.13 (s, 1H), 7.74 (d, J=8.9, 2H), 7.65 (d, J=8.8, 2H), 3.41-3.33 (m, 1H), 2.68 (dd, J=6.8, 16.8, 1H), 2.23 (d, J=16.7, 1H), 2.08 (s, 3H), 1.07 (d, J=7.3, 3H). $^{13}$C NMR (75 MHz, DMSO-d$_6$) δ 168.50, 166.27, 152.25, 140.27, 129.24, 126.24, 118.70, 33.47, 26.91, 24.02, 15.87. MS: 246 (M+1).

Example 8: Preparation of

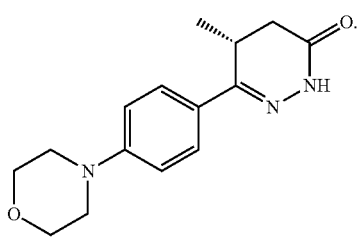 [SMILES: C[C@@H]1CC(=O)NN=C1c1ccc(N2CCOCC2)cc1]

To 200 mg (0.984 mmol) of (R)-6-(4-aminophenyl)-5-methyl-4,5-dihydropyridazin-3(2H)-one dissolved in 1 mL of DMF was added 250 uL (2.00 mmol) of bis(2-bromoethyl) ether and 400 mg of K$_2$CO$_3$ and the mixture was stirred overnight at 60° C. The next day another 250 uL of bis(2-bromoethyl) ether and 170 mg of K$_2$CO$_3$ was added. After 3 h, EtOAc and water were added, the water was rinsed with EtOAc, the combined EtOAc washes were dried and concentrated. Chromatography with 0-4% MeOH in CH$_2$Cl$_2$ yielded 125 mg of product (46%). $^1$H NMR (300 MHz, CDCl$_3$) δ 8.61 (s, 1H), 7.68 (d, J=8.8, 2H), 6.92 (d, J=8.8, 2H), 3.99-3.76 (m, 4H), 3.44-3.31 (m, 1H), 3.29-3.22 (m, 4H), 2.70 (dd, J=6.7, 16.8, 1H), 2.46 (d, J=16.7, 1H), 1.24 (d, J=7.3, 3H). $^{13}$C NMR (75 MHz, CDCl$_3$) δ 166.64, 154.05, 152.18, 127.10, 125.33, 114.73, 66.69, 48.33, 33.93, 27.94, 16.36. MS: 274 (M+1).

Example 9: Preparation of

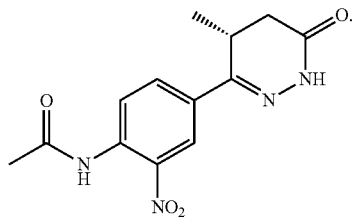 [SMILES: CC(=O)Nc1ccc(C2=NNC(=O)C[C@H]2C)cc1[N+](=O)[O-]]

To 3.09 g of the compound prepared in Example 7 (15.3 mmol) dissolved in 30 mL of sulfuric and cooled in an ice bath was added 0.72 mL of fuming nitric acid (15 mmol) in 8 mL sulfuric acid via an addition funnel over 10 min. After stirring 1 h the mixture was poured onto ice. The yellow solid was filtered off and the water was rinsed several times with EtOAc before drying and combining with the yellow solid. Chromatography with 40-60% EtOAc in hexane yielded 1.12 g (25%) of product as a yellow solid which could be recrystallized from EtOAc. $^1$H NMR (300 MHz, DMSO) δ 11.13 (s, 1H), 10.41 (s, 1H), 8.25 (d, J=1.8, 1H), 8.07 (dd, J=1.8, 8.6, 1H), 7.71 (d, J=8.6, 1H), 3.55-3.40 (m, 1H), 2.74 (dd, J=6.9, 16.8, 1H), 2.27 (d, J=16.8, 1H), 2.09 (s, 3H), 1.08 (d, J=7.2, 3H). $^{13}$C NMR (75 MHz, DMSO-d$_6$) δ 168.57, 166.31, 150.37, 142.19, 131.69, 131.32, 130.60, 125.07, 121.70, 33.30, 26.81, 23.44, 15.64. MS: 291 (M+1).

Example 10: Preparation of

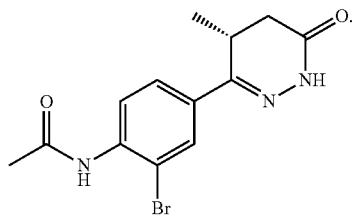 [SMILES: CC(=O)Nc1ccc(C2=NNC(=O)C[C@H]2C)cc1Br]

To 1.0 g of the compound prepared in Example 7 (4.1 mmol) dissolved in 20 mL HOAc was added 0.65 g of bromine (4.1 mmol). After several hours the reaction was concentrated, the crude product was dissolved in DCM and extracted with NaHCO3 (aq) and brine before drying, concentrating and chromatography with 20-40% EtOAc in hexane to yield 198 mg of product (15%). $^1$H NMR (300 MHz, CDCl$_3$) δ 8.81 (s, 1H), 8.45 (d, J=8.7, 1H), 8.03 (d, J=2.0, 1H), 7.73 (s, 1H), 7.64 (dd, J=2.0, 8.8, 1H), 3.42-3.19 (m, 1H), 2.72 (dd, J=6.8, 17.0, 1H), 2.49 (d, J=16.9, 1H), 2.28 (s, 3H), 1.24 (d, J=7.4, 3H). MS: 324 (M+1).

Example 11: Preparation of

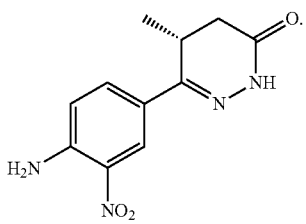 [SMILES: C[C@@H]1CC(=O)NN=C1c1ccc(N)c([N+](=O)[O-])c1]

To 58 mg of the compound prepared in Example 9 (0.20 mmol) dissolved in 10 mL of MeOH was added a solution of 48 mg NaOH (1.2 mmol) in 0.5 mL water. After 1 h the reaction was concentrated, water was added and rinsed with EtOAc, drying, and concentrating gave 48 mg (93%) of TP8. $^1$H NMR (300 MHz, DMSO) δ 10.92 (s, 1H), 8.28 (d, J=2.0, 1H), 7.87 (dd, J=2.1, 9.0, 1H), 7.76 (s, 2H), 7.06 (d, J=9.0, 1H), 3.33 (s, 1H), 2.67 (dd, J=6.8, 16.8, 1H), 2.22 (d, J=16.6, 1H), 1.06 (d, J=7.3, 3H). $^{13}$C NMR (75 MHz, DMSO) δ 166.25, 151.12, 146.69, 132.72, 129.80, 122.57, 122.19, 119.80, 33.43, 26.70, 15.77. MS: 249 (M+1).

Example 12: Preparation of

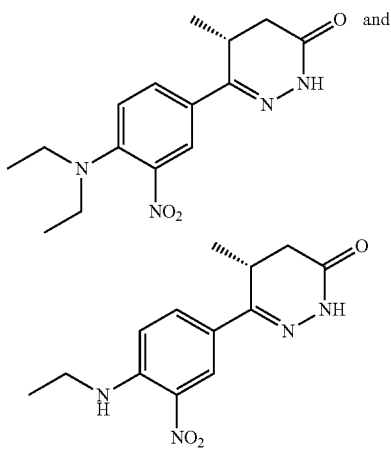

To 35 mg of the compound prepared in Example 11 (0.14 mmol) dissolved in 0.5 mL DMF was added 70 mg of acetaldehyde (1.6 mmol) and 170 mg of NaBH(OAc)3 (0.80 mmol) and 10 uL of HOAc. After stirring 3 h water and EtOAc were added, the EtOAc separated, dried, and chromatographed with 30-50% EtOAc in hexane to isolate 3 mg of diethylamine and 8 mg of monoethylamine Diethyl compound: $^1$H NMR (300 MHz, CDCl$_3$) δ 8.58 (s, 1H), 8.04 (d, J=2.3, 1H), 7.84 (dd, J=2.3, 9.0, 1H), 7.11 (d, J=9.0, 1H), 3.30-33.6 (m, 1H), 3.26 (q, J=7.1, 4H), 2.71 (dd, J=6.8, 16.9, 1H), 2.48 (d, J=17.0, 1H), 1.25 (d, J=7.4, 3H), 1.16 (t, J=7.1, 6H). MS: 305 (M+1). Monoethyl compound: $^1$H NMR (300 MHz, CDCl$_3$) δ 8.75 (s, 1H), 8.44 (s, 1H), 8.26 (s, 1H), 8.03 (d, J=9.0, 1H), 6.93 (d, J=9.2, 1H), 3.58-3.28 (m, 3H), 2.72 (dd, J=6.6, 16.9, 1H), 2.49 (d, J=16.7, 1H), 1.40 (t, J=7.1, 3H), 1.25 (d, J=7.2, 3H). $^{13}$C NMR (75 MHz, CDCl3) δ 166.54, 152.27, 146.16, 133.64, 131.05, 124.31, 121.77, 114.56, 37.88, 33.79, 27.60, 16.31, 14.34. MS: 277 (M+1).

The optical purity of the diethylamine compound was determined using chiral SCF chromatography and comparison to commercially available racemic material: Column: ChiralPak AS-H, 250×4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C. Molecular weight of compound was 304. UV detection was from 200-400 nm. Methanol blanks were inserted between sample injections to guard against carryover between samples. Retention times of separated isomers: 5.36, 6.64 min; retention time of the diethylamine compound, 6.60 min, approx. 19:1 ratio of enantiomers detected.

Example 13: Preparation of

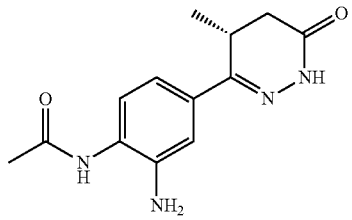

To 22 mg of

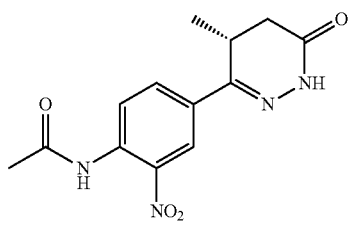

dissolved in 10 mL MeOH was added 22 mg of 10% Pd on carbon and the flask was fitted with a balloon containing H2 gas. After stirring 1 h the catalyst was filtered and rinsed with MeOH, the solvent was concentrated to give 18 mg of product as a white solid (92%). $^1$H NMR (300 MHz, MeOD) δ 7.31 (d, J=1.8, 1H), 7.22 (d, J=8.3, 1H), 7.15 (dd, J=1.9, 8.3, 1H), 3.36-3.40 (m, 1H), 2.72 (dd, J=7.0, 17.0, 1H), 2.42-2.28 (m, 1H), 2.17 (s, 3H), 1.15 (d, J=7.3, 3H). $^{13}$C NMR (75 MHz, MeOD) δ 172.23, 169.55, 156.19, 143.24, 134.64, 126.88, 126.59, 117.31, 115.88, 34.60, 29.13, 23.17, 16.50. MS: 261 (M+1).

Example 14: Preparation of

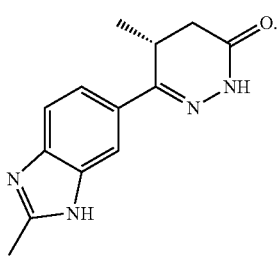 [SMILES: Cc1nc2ccc(C3=NNC(=O)C[C@H]3C)cc2[nH]1]

The nitro reduction was done similarly with 40 mg

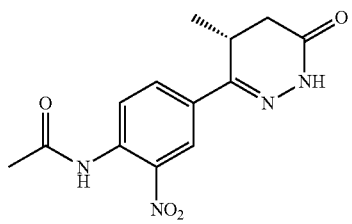

in 20 mL MeOH with 40 mg Pd on carbon. The product was heated in a mixture of 2 mL toluene and 1 mL HOAc for 1 h at 120° C. Cooling, concentration and chromatography with 0-10% NH$_3$ sat'd MeOH in DCM yielded 18 mg of product (54%). $^1$H NMR (300 MHz, CD$_3$OD) δ 8.00-7.84 (m, 1H), 7.74 (d, J=8.4, 1H), 7.50 (d, J=8.1, 1H), 3.52 (p, J=7.1, 1H), 2.78 (dd, J=6.9, 16.9, 1H), 2.58 (s, 3H), 2.39 (d, J=17.0, 1H), 1.21 (d, J=7.3, 3H). MS: 243 (M+1).

Example 15: Synthesis of

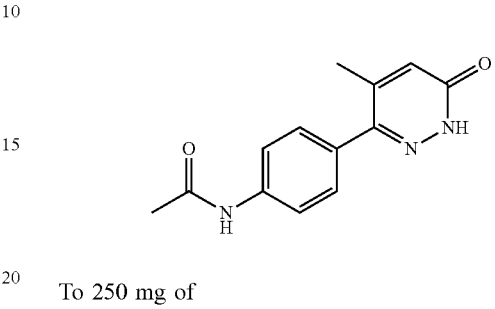

To 250 mg of

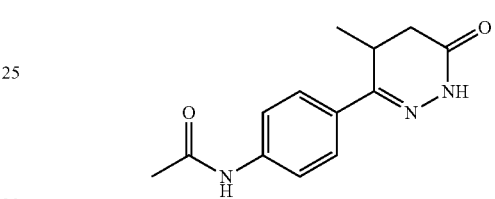

(1.02 mmol) dissolved in 10 mL CH$_3$CN was added 347 mg of CuCl$_2$ hydrate (2.3 mmol) and the solution was heated at 80° C. for 1 h. After cooling the reaction was poured onto ice and the product was filtered and rinsed with water to produce 110 mg (44%). $^1$H NMR (300 MHz, DMSO-d$_6$) δ 13.02 (s, 1H), 10.11 (s, 1H), 7.67 (d, J=8.3, 2H), 7.41 (d, J=8.3, 2H), 6.82 (s, 1H), 3.39 (s, 3H), 2.08 (s, 3H). MS: 244 (M+1).

Example 16

Compounds were tested against various cells lines using the following assays or assays similar to the ones presented herein.

HeLa Cytotoxicity Assay Protocol: Day 0: HeLa cells (ATCC, HeLa CCL-2) are grown to 95% confluence in DMEM, 10% FBS/Pen/Strep/L-Glutamine. Day 1: Plate cells (1000 per well) in 40 μl culturing media using Corning 384-well plates (3570), incubate in standard TC conditions (5% CO2, 95% humidity, 37 degrees C.) for 24 hours. Day 2: Dilute each concentration of a half-log serial dilution of compound (1 mM-100 nM) 1:200 in culturing media and add 10 μl (50 μl total volume) of that dilution to designated wells (8 replicates per concentration). The final dilution will be 1000× (1 μM-100 pM). Day 4: Remove plate from incubator to cool for 20 minutes to room temperature. Add 40 μl of a 25% Promega Cell Titer Glo solution (diluted 1:3 with room temperature PBS) with Thermo combi or multichannel and incubate for 10 minutes. Read on Perkin-Elmer EnVision with US LUM settings for 0.1 second per well.

A549 Cytotoxicity Assay Protocol. Day 0: A549 cells (ATCC, A549 CCL-185) are grown to 95% confluence in RPMI, 10% FBS/Pen/Strep/L-Glutamine. Day 1: Plate cells (1000 per well) in 40 μl culturing media using Corning 384-well plates (3570), incubate in standard TC conditions (5% CO$_2$, 95% humidity, 37° C.) for 24 h. Day 2: Dilute each concentration of a half-log serial dilution of compound (1 mM-100 nM) 1:200 in culturing media and add 10 µl (50 µl total volume) of that dilution to designated wells (8 replicates per concentration). The final dilution will be 1000× (1 µM-100 pM). Day 4: Remove plate from incubator to cool for 20 minutes to room temperature. Add 40 µl of a 25% Promega Cell Titer Glo solution (diluted 1:3 with room temperature PBS) with Thermo combi or multichannel and incubate for 10 min. Read on Perkin-Elmer EnVision with US LUM settings for 0.1 second per well.

Selective toxicity in cell line panel. H2122 Assay Protocol Day 0: H2122 cells (ATCC, H2122 CCL-5985) are grown to 95% confluence in RPMI, 10% FBS/Pen/Strep/L-Glutamine. Day 1: Plate cells (750 per well) in 40 µl culturing media using Corning 384-well plates (3570), incubate in standard TC conditions (5% $CO_2$, 95% humidity, 37 degrees C.) for 24 h. Day 2: Dilute each concentration of a half-log serial dilution of compound (1 mM-100 nM) 1:200 in culturing media and add 10 µl (50 µl total volume) of that dilution to designated wells (8 replicates per concentration). The final dilution will be 1000× (1 µM-100 pM). Day 4: Remove plate from incubator to cool for 20 minutes to room temperature. Add 40 µl of a 25% Promega Cell Titer Glo solution (diluted 1:3 with room temperature PBS) with Thermo combi or multichannel and incubate for 10 minutes. Read on Perkin-Elmer EnVision with US LUM settings for 0.1 second per well.

COLO741 Assay Protocol. Day 0: COLO741 cells (ECACC, COLO741 93052621) are grown to 95% confluence in RPMI, 10% FBS/Pen/Strep/L-Glutamine. Day 1: Plate cells (1500 per well) in 40 µl culturing media using Corning 384-well plates (3570), incubate in standard TC conditions (5% $CO_2$, 95% humidity, 37° C.) for 24 h. Day 2: Dilute each concentration of a half-log serial dilution of compound (1 mM-100 nM) 1:200 in culturing media and add 10 µl (50 µl total volume) of that dilution to designated wells (8 replicates per concentration). The final dilution will be 1000× (1 µM-100 pM). Day 4: Remove plate from incubator to cool for 20 minutes to room temperature. Add 40 µl of a 25% Promega Cell Titer Glo solution (diluted 1:3 with room temperature PBS) with Thermo combi or multichannel and incubate for 10 minutes. Read on Perkin-Elmer EnVision with US LUM settings for 0.1 second per well.

Toxicity in cell line Panel. HCT116 Assay Protocol. Day 0: HCT116 cells (ATCC, HCT116 CCL-247) are grown to 95% confluence in RPMI, 10% FBS/Pen/Strep/L-Glutamine. Day 1: Plate cells (1000 per well) in 40 µl culturing media using Corning 384-well plates (3570), incubate in standard TC conditions (5% $CO_2$, 95% humidity, 37° C.) for 24 h. Day 2: Dilute each concentration of a half-log serial dilution of compound (1 mM-100 nM) 1:200 in culturing media and add 10 µl (50 µl total volume) of that dilution to designated wells (8 replicates per concentration). The final dilution will be 1000× (1 µM-100 pM). Day 4: Remove plate from incubator to cool for 20 minutes to room temperature. Add 40 µl of a 25% Promega Cell Titer Glo solution (diluted 1:3 with room temperature PBS) with Thermo combi or multichannel and incubate for 10 min. Read on Perkin-Elmer EnVision with US LUM settings for 0.1 second per well.

IMR90 Assay Protocol. Day 0: IMR90 cells are grown to 95% confluence in MEM, 10% FBS/Pen/Strep/L-Glutamine Day 1: Plate cells (ATCC, IMR90 CCL-186), 2000 per well, in 40 µl culturing media using Corning 384-well plates (3570), incubate in standard TC conditions (5% $CO_2$, 95% humidity, 37° C.) for 24 h. Day 2: Dilute each concentration of a half-log serial dilution of compound (1 mM-100 nM) 1:200 in culturing media and add 10 µl (50 µl total volume) of that dilution to designated wells (8 replicates per concentration). The final dilution will be 1000× (1 µM-100 pM). Day 4: Remove plate from incubator to cool for 20 minutes to room temperature. Add 40 µl of a 25% Promega Cell Titer Glo solution (diluted 1:3 with room temperature PBS) with Thermo combi or multichannel and incubate for 10 min. Read on Perkin-Elmer EnVision with US LUM settings for 0.1 second per well.

Cytotoxicity (72 h) on cancer cell panel. HEK293 Assay Protocol. Day 0: HEK293 cells (HEK293T, ATCC) grown in Triple flask (NUNC) to ~95% confluence (TrypLE Phenol Red free) and resuspended for dispensing at 50,000 cells/mL of DMEM, 10% FBS/Pen/Strep/L-Glutamine (Compact SelecT). Day 1: Plate cells @2000 per well in 40 µL media (DMEM/10% FBS/Pen/Strep/L-Glutamine) using Corning 8867BC 384 well plates; incubate in standard TC conditions (5% $CO_2$; 95% humidity, 37° C.) for 24 h (Compact SelecT). Day 2: Add 100 nL compound per well at dose into 40 uL assay volume using a pin tool (CyBi Well). Pin 100 nL cytotoxic compounds, Mitoxandrone (CID 4212) to positive control wells to a final concentration of 10 µM (100 nL 4 mM DMSO stock). Incubate for 72 hours at 37° C. in Liconic incubator, 95% humidity 5% $CO_2$. Day 4: Remove plate from incubator to cool for 15 minutes to room temperature; add 20 µL 50% Promega CellTiterGlo (diluted 1:1 with PBS, pH 7.4) with Thermo Combi. Incubate at RT for 5 minutes. Read on Perkin-Elmer EnVision with US LUM settings for 0.1 sec per well.

HepG2 Assay Protocol. Day 0: HepG2 cells (ATCC) were grown in Triple flasks (NUNC) to ~95% confluence (TrypLE Phenol Red free) and resuspended for dispensing at 50,000 cells/mL of DMEM, 10% FBS/Pen/Strep/L-Glutamine (using the TAP Compact SelecT automated cell culture system). Day 1: Plate cells @2000 per well in 40 µL media (DMEM/10% FBS/Pen/Strep/L-Glutamine) using Corning 8867BC 384 well plates; incubate in standard TC conditions (5% $CO_2$; 95% humidity, 37° C.) for 24 hours (Compact SelecT). Day 2: Add 100 nL compound per well at dose into 40 uL assay volume using a pin tool (CyBi Well). Pin 100 nL cytotoxic compounds, mitoxantrone to positive control wells to a final concentration (CID 4212) of 10 µM (100 nL 4 mM DMSO stock). Incubate for 72 h at 37° C. in Liconic incubator, 95% humidity 5% $CO_2$. Day 4: Remove plate from incubator, cool for 15 min to room temperature; add 20 µL 50% Promega CellTiter-Glo (diluted 1:1 with PBS, pH 7.4) with Thermo Combi. Incubate at RT for 5 min. Read plates on a Perkin-Elmer EnVision plate reader with standard luminescence settings for 0.1 sec per well.

A549 Assay Protocol. Day 0: A549 cells (ATCC) are grown in a Triple flask (NUNC) to ~95% confluence (TrypLE Phenol Red free) and resuspended for dispensing at 25,000 cells/mL of DMEM, 10% FBS/Pen/Strep/L-Glutamine (using the TAP Compact SelecT automated cell culture system). Day 1: Plate cells at 1000 per well in 40 uL media (DMEM/10% FBS/Pen/Strep/L-Glutamine) using Corning 8867BC 384 well plates; incubate in standard TC conditions (5% CO2; 95% humidity, 37° C.) for 24 hours (Compact SelecT). Day 2: Add 100 nL compound per well at dose into 40 uL assay volume using a pin tool (CyBi Well). Pin 100 nL cytotoxic compounds, mitoxantrone (CID 4212) to positive control wells to a final concentration of 10 uM (100 nL 4 mM DMSO stock). Incubate for 72 hours at 37° C. in Liconic incubator, 95% humidity 5% $CO_2$. Day 4: Remove plate from incubator, cool for 15 minutes to room temperature; add 20 µL 50% Promega CellTiterGlo (diluted 1:1 with PBS, pH 7.4) with Thermo Combi. Incubate at room temperature for 5 minutes. Read plates on Perkin-Elmer EnVision with standard luminescence settings for 0.1 sec per well.

The assays described here are non-limiting examples of how the activities of certain compounds can be measured. Other assays can also be used.

Example 16

The compounds can be prepared according to the following methods. The methods can also be adapted to make further compounds not specifically exemplified in this section.

All reactions were carried out under nitrogen ($N_2$) atmosphere. All reagents and solvents were purchased from commercial vendors and used as received. NMR spectra were recorded on a Bruker (300 MHz $^1$H, 75 MHz $^{13}$C) or a Varian (500 MHz $^1$H, 126 MHz $^{13}$C) spectrometer. Proton and carbon chemical shifts are reported in ppm (δ) referenced to the NMR solvent. Fluorine spectra (Bruker, 282 MHz) were recorded without internal standard. Data are reported as follows: chemical shifts, multiplicity (br=broad, s=singlet, d=doublet, t=triplet, q=quartet, m=multiplet; coupling constant(s) in Hz). Flash chromatography was performed using 40-60 μm Silica Gel (60 Å mesh) on a Teledyne Isco Combiflash R$_f$. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates. Elemental analysis was performed by Robertson Microlit Laboratories, Ledgewood N.J. SCF Chromatography was run on a ChiralPak AS-H column, 250×4.6 mm, 5 um, mobile phase modifier: 100% MeOH, gradient: 5 to 50% MeOH over 10 min, flow rate: 4 mL/min, back pressure: 100 bar, column temperature: 40° C.

Synthesis of

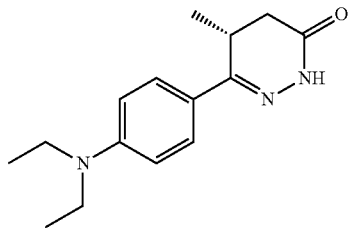

TP2

TP2—

To 200 mg (0.98 mmol) of (R)-6-(4-aminophenyl)-5-methyl-4,5-dihydropyridazin-3(2H)-one (purchased from Toronto Research Chemicals Inc.) dissolved in 5 mL of MeOH was added 87 mg of acetaldehyde (2.0 mmol), 113 uL of HOAc (2.0 mmol) and 124 mg (2.0 mmol) of NaBH$_3$CN and the reaction was stirred overnight at room temperature. The next day the same quantity of reagents were added and the reaction stirred another 24 h. The mixture was concentrated and partitioned between CH$_2$Cl$_2$ and water, the CH$_2$Cl$_2$ was separated, dried, and concentrated before chromatography with 20-40% EtOAc in hexane isolated 210 mg of product as a white solid (82%). $^1$H NMR (300 MHz, CDCl$_3$) δ 8.95 (s, 1H), 7.64 (d, J=8.7, 2H), 6.66 (d, J=8.7, 2H), 3.37 (dd, J=9.6, 16.4, 5H), 2.67 (dd, J=6.5, 16.8, 1H), 2.43 (d, J=16.8, 1H), 1.41-1.02 (m, 10H). $^{13}$C NMR (75 MHz, CDCl$_3$) δ 166.82, 154.55, 148.79, 127.32, 120.81, 111.08, 77.42, 77.00, 76.58, 44.32, 33.92, 27.74, 16.37, 12.50. MS: 260 (M+1). Racemic material was made starting with racemic amine and had identical NMR and LC spectra.

Synthesis of

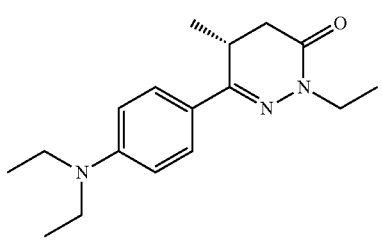

TP7

TP7—

To 40 mg (0.15 mmol) of TP2 dissolved in 0.5 mL DMF was added 6.0 mg of a 60% oil dispersion of NaH (0.15 mmol) and a precipitate appeared which dissolved upon the addition of 20 μL of ethyl iodide. After 30 min, EtOAc and water were added, the EtOAc was dried, concentrated and chromatographed with 25% EtOAc in hexane to yield 27 mg of product as an oil which solidified upon standing (61%). $^1$H NMR (300 MHz, CDCl$_3$) δ 7.66 (d, J=9.1, 2H), 6.67 (d, J=9.1, 2H), 3.98 (dq, J=7.1, 14.2, 1H), 3.81 (dq, J=7.1, 14.1, 1H), 3.40 (q, J=7.0, 4H), 3.33-3.12 (m, 1H), 2.62 (dd, J=6.6, 16.5, 1H), 2.41 (dd, J=1.5, 16.5, 1H), 1.25 (t, J=7.1, 3H), 1.19 (t, J=6.9, 9H). $^{13}$C NMR (75 MHz, CDCl$_3$) δ 164.09, 154.65, 148.71, 127.29, 121.14, 111.11, 44.37, 43.13, 34.69, 27.95, 16.27, 13.14, 12.52. MS: 288 (M+1).

Synthesis of

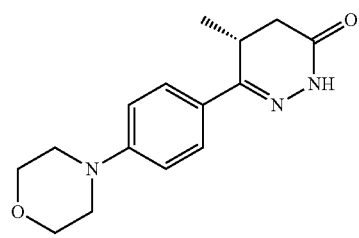

TP5

TP5—

To 200 mg (0.984 mmol) of (R)-6-(4-aminophenyl)-5-methyl-4,5-dihydropyridazin-3(2H)-one dissolved in 1 mL of DMF was added 250 μL (2.00 mmol) of bis(2-bromoethyl)ether and 400 mg of K$_2$CO$_3$ and the mixture was stirred overnight at 60° C. The next day another 250 μL of bis(2-bromoethyl) ether and 170 mg of K$_2$CO$_3$ was added. After 3 h, EtOAc and water were added, the water was rinsed with EtOAc, the combined EtOAc washes were dried and concentrated. Chromatography with 0-4% MeOH in CH$_2$Cl$_2$ yielded 125 mg of product (46%). $^1$H NMR (300 MHz, CDCl$_3$) δ 8.61 (s, 1H), 7.68 (d, J=8.8, 2H), 6.92 (d, J=8.8, 2H), 3.99-3.76 (m, 4H), 3.44-3.31 (m, 1H), 3.29-3.22 (m, 4H), 2.70 (dd, J=6.7, 16.8, 1H), 2.46 (d, J=16.7, 1H), 1.24 (d, J=7.3, 3H). $^{13}$C NMR (75 MHz, CDCl$_3$) δ 166.64, 154.05, 152.18, 127.10, 125.33, 114.73, 66.69, 48.33, 33.93, 27.94, 16.36. MS: 274 (M+1). Anal. Calcd. for C$_{15}$H$_{19}$N$_3$O$_2$: C, 65.91; H, 7.01; N, 15.37. Found: 65.81; H, 6.66; N, 15.26.

Synthesis of

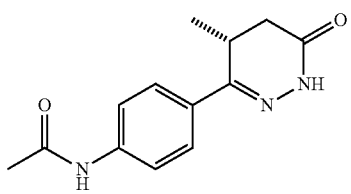

TP6-int

TP6-int.

2.00 g (9.84 mmol) of (R)-6-(4-aminophenyl)-5-methyl-4,5-dihydropyridazin-3(2H)-one was stirred 1 h in 5 mL of acetic anhydride before addition of 30 mL water, filtration, rinsing the solids with water and drying to yield 2.20 g of product (91%). $^1$H NMR (300 MHz, DMSO-d$_6$) δ 10.92 (s, 1H), 10.13 (s, 1H), 7.74 (d, J=8.9, 2H), 7.65 (d, J=8.8, 2H), 3.41-3.33 (m, 1H), 2.68 (dd, J=6.8, 16.8, 1H), 2.23 (d, J=16.7, 1H), 2.08 (s, 3H), 1.07 (d, J=7.3, 3H). $^{13}$C NMR (75 MHz, DMSO-d$_6$) δ 168.50, 166.27, 152.25, 140.27, 129.24, 126.24, 118.70, 33.47, 26.91, 24.02, 15.87. MS: 246 (M+1)

Synthesis of

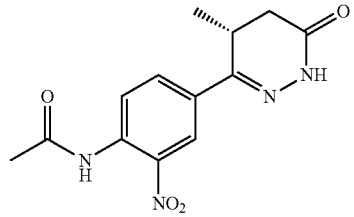

TP6

TP6—

To 3.09 g of TP6 int. (15.3 mmol) dissolved in 30 mL of sulfuric acid and cooled in an ice bath was added 0.72 mL of 90% nitric acid (15 mmol) in 8 mL sulfuric acid via an addition funnel over 10 min. After stirring 1 h the mixture was poured onto ice. The yellow solid was filtered off and the water was rinsed several times with EtOAc before drying and combining with the yellow solid. Chromatography with 40-60% EtOAc in hexane yielded 1.12 g (25%) of product as a yellow solid which was recrystallized from EtOAc. $^1$H NMR (300 MHz, DMSO-d$_6$) δ 11.13 (s, 1H), 10.41 (s, 1H), 8.25 (d, J=1.8, 1H), 8.07 (dd, J=1.8, 8.6, 1H), 7.71 (d, J=8.6, 1H), 3.55-3.40 (m, 1H), 2.74 (dd, J=6.9, 16.8, 1H), 2.27 (d, J=16.8, 1H), 2.09 (s, 3H), 1.08 (d, J=7.2, 3H). $^{13}$C NMR (75 MHz, DMSO-d$_6$) δ 168.57, 166.31, 150.37, 142.19, 131.69, 131.32, 130.60, 125.07, 121.70, 33.30, 26.81, 23.44, 15.64. MS: 291 (M+1).

Synthesis of

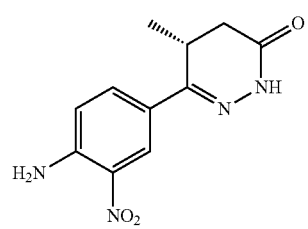

TP8

TP8—

To 58 mg of TP6 (0.20 mmol) dissolved in 10 mL of MeOH was added a solution of 48 mg NaOH (1.2 mmol) in 0.5 mL water. After 1 h the reaction was concentrated, water was added and rinsed with EtOAc, the EtOAc was dried and concentrated to give 48 mg (93%) of TP8. $^1$H NMR (300 MHz, DMSO-d$_6$) δ 10.92 (s, 1H), 8.28 (d, J=2.0, 1H), 7.87 (dd, J=2.1, 9.0, 1H), 7.76 (s, 2H), 7.06 (d, J=9.0, 1H), 3.33 (s, 1H), 2.67 (dd, J=6.8, 16.8, 1H), 2.22 (d, J=16.6, 1H), 1.06 (d, J=7.3, 3H). $^{13}$C NMR (75 MHz, DMSO-d$_6$) δ 166.25, 151.12, 146.69, 132.72, 129.80, 122.57, 122.19, 119.80, 33.43, 26.70, 15.77. MS: 249 (M+1).

Synthesis of

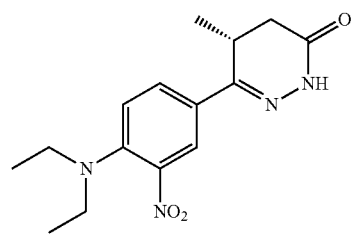

TP8A

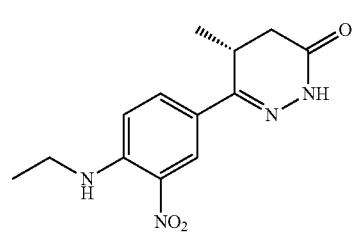

TP8B

To 35 mg of TP8 (0.14 mmol) dissolved in 0.5 mL DMF was added 70 mg of acetaldehyde (1.6 mmol) and 170 mg of NaBH(OAc)$_3$ (0.80 mmol) and 10 μL of HOAc. After stirring 3 h, water and EtOAc were added, the EtOAc separated, dried, and chromatographed with 30-50% EtOAc in hexane to isolate 3 mg of the diethylamine (TP8A) and 8 mg of the monoethylamine (TP8B). TP8A (diethyl)$^1$H NMR (300 MHz, CDCl$_3$) δ 8.58 (s, 1H), 8.04 (d, J=2.3, 1H), 7.84 (dd, J=2.3, 9.0, 1H), 7.11 (d, J=9.0, 1H), 3.30-3.36 (m, 1H), 3.26 (q, J=7.1, 4H), 2.71 (dd, J=6.8, 16.9, 1H), 2.48 (d, J=17.0, 1H), 1.25 (d, J=7.4, 3H), 1.16 (t, J=7.1, 6H). MS: 305 (M+1).

TP8B (monoethyl) ¹H NMR (300 MHz, CDCl₃) δ 8.75 (s, 1H), 8.44 (s, 1H), 8.26 (s, 1H), 8.03 (d, J=9.0, 1H), 6.93 (d, J=9.2, 1H), 3.58-3.28 (m, 3H), 2.72 (dd, J=6.6, 16.9, 1H), 2.49 (d, J=16.7, 1H), 1.40 (t, J=7.1, 3H), 1.25 (d, J=7.2, 3H). ¹³C NMR (75 MHz, CDCl₃) δ 166.54, 152.27, 146.16, 133.64, 131.05, 124.31, 121.77, 114.56, 37.88, 33.79, 27.60, 16.31, 14.34. MS: 277 (M+1).

The optical purity of TP8A was determined using chiral SCF chromatography and comparison to commercially available racemic material: Column: ChiralPak AS-H, 250× 4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C. UV detection was from 200-400 nm. Retention times of separated isomers: 5.36, 6.64 min; retention time of TP8A, 6.60 min, 1:19 ratio of enantiomers detected.

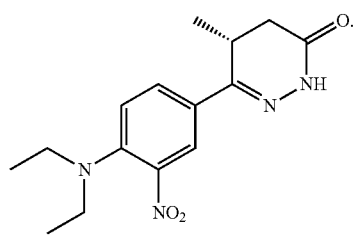 [SMILES: CCN(CC)c1ccc(C2=NNC(=O)C[C@H]2C)cc1[N+](=O)[O-]]

Commercial material: ¹H NMR (300 MHz, CDCl₃) δ 8.58 (s, 1H), 8.03 (d, J=2.2, 1H), 7.84 (dd, J=2.3, 9.0, 1H), 7.11 (d, J=9.0, 1H), 3.34 (t, J=4.1, 1H), 3.25 (t, J=7.1, 4H), 2.70 (dd, J=6.8, 17.0, 1H), 2.48 (d, J=16.8, 1H), 1.25 (d, J=7.4, 3H), 1.16 (t, J=7.1, 7H). ¹³C NMR (75 MHz, CDCl₃) δ 166.28, 152.02, 145.24, 141.21, 129.77, 124.94, 123.94, 121.00, 46.10, 33.80, 27.81, 16.24, 12.56. MS: 305 (M+1).

Synthesis of

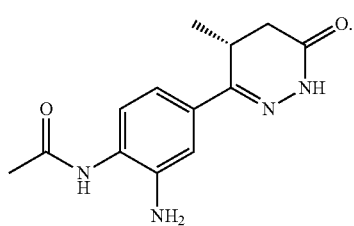

TP9 int.

To 22 mg of TP6 (0.076 mmol) dissolved in 10 mL MeOH was added 22 mg of 10% Pd on carbon and the flask was fitted with a balloon containing H₂ gas. After stirring 1 h the catalyst was filtered and rinsed with MeOH, the solvent was concentrated to give 18 mg of product as a white solid (92%). ¹H NMR (300 MHz, CD₃OD) δ 7.31 (d, J=1.8, 1H), 7.22 (d, J=8.3, 1H), 7.15 (dd, J=1.9, 8.3, 1H), 3.36-3.40 (m, 1H), 2.72 (dd, J=7.0, 17.0, 1H), 2.42-2.28 (m, 1H), 2.17 (s, 3H), 1.15 (d, J=7.3, 3H). ¹³C NMR (75 MHz, CD₃OD) δ 172.23, 169.55, 156.19, 143.24, 134.64, 126.88, 126.59, 117.31, 115.88, 34.60, 29.13, 23.17, 16.50. MS: 261 (M+1).

Synthesis of

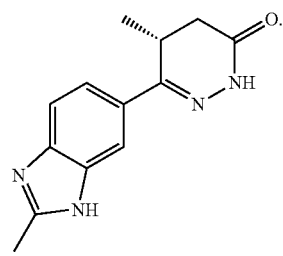

The nitro reduction was done similarly with 40 mg TP6 in 20 mL MeOH with 40 mg Pd on carbon. The product was heated in a mixture of 2 mL toluene and 1 mL HOAc for 1 h at 120° C. Cooling, concentration and chromatography with 0-10% NH₃ sat'd MeOH in CH₂Cl₂ yielded 18 mg of product (54%). ¹H NMR (300 MHz, CD₃OD) δ 8.00-7.84 (m, 1H), 7.74 (d, J=8.4, 1H), 7.50 (d, J=8.1, 1H), 3.52 (p, J=7.1, 1H), 2.78 (dd, J=6.9, 16.9, 1H), 2.58 (s, 3H), 2.39 (d, J=17.0, 1H), 1.21 (d, J=7.3, 3H). MS: 243 (M+1).

Synthesis of

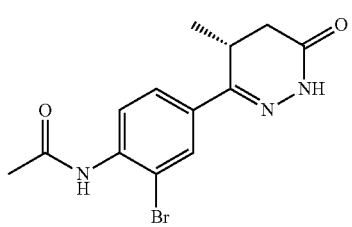

TP10A.

To 1.0 g of TP6 int (4.1 mmol) dissolved in 20 mL HOAc was added 0.65 g of bromine (4.1 mmol). After several hours the reaction was concentrated, the crude product was dissolved in CH₂Cl₂ and rinsed with NaHCO₃ (aq) and brine before drying, concentrating and chromatography with 20-40% EtOAc in hexane to yield 198 mg of product (15%). ¹H NMR (300 MHz, CDCl₃) δ 8.81 (s, 1H), 8.45 (d, J=8.7, 1H), 8.03 (d, J=2.0, 1H), 7.73 (s, 1H), 7.64 (dd, J=2.0, 8.8, 1H), 3.42-3.19 (m, 1H), 2.72 (dd, J=6.8, 17.0, 1H), 2.49 (d, J=16.9, 1H), 2.28 (s, 3H), 1.24 (d, J=7.4, 3H). ¹³C NMR (75 MHz, CDCl3) δ 168.27, 166.48, 152.05, 136.87, 131.29, 129.73, 125.93, 121.21, 113.49, 33.78, 27.90, 24.87, 16.21. MS: 324 (M+1).

Synthesis of

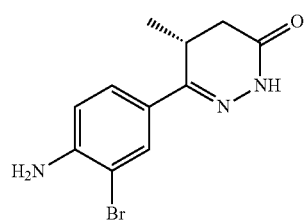

TB10B.

To a solution of 188 mg of TP10A (0.58 mmol) in 10 mL MeOH was added a solution of 50 mg NaOH (1.3 mmol) in 1 mL water. After 1 h, another 50 mg of NaOH (s) was added and the solution was heated at 70 C for 4 h before cooling, concentrating, and rinsing several times with EtOAc. Concentration produced 130 mg of product as an off-white solid (79%). $^1$H NMR (300 MHz, DMSO-$d_6$) δ 10.79 (s, 1H), 7.76 (d, J=2.0 Hz, 1H), 7.50 (dd, J=8.6, 2.1 Hz, 1H), 6.80 (d, J=8.6 Hz, 1H), 5.74 (s, 2H), 3.35-3.22 (m, 1H), 2.62 (dd, J=16.7, 6.8 Hz, 1H), 2.18 (d, J=16.6 Hz, 1H), 1.02 (d, J=7.2 Hz, 3H). $^{13}$C NMR (75 MHz, DMSO-$d_6$) δ 166.12, 151.79, 146.87, 129.57, 126.08, 123.80, 114.80, 107.21, 40.33, 40.06, 39.78, 39.50, 39.22, 38.94, 38.67, 33.50, 26.74, 15.90. MS 283 (M+1).

Synthesis of TP11A, TP11B, and TP11C were made according to the following scheme.

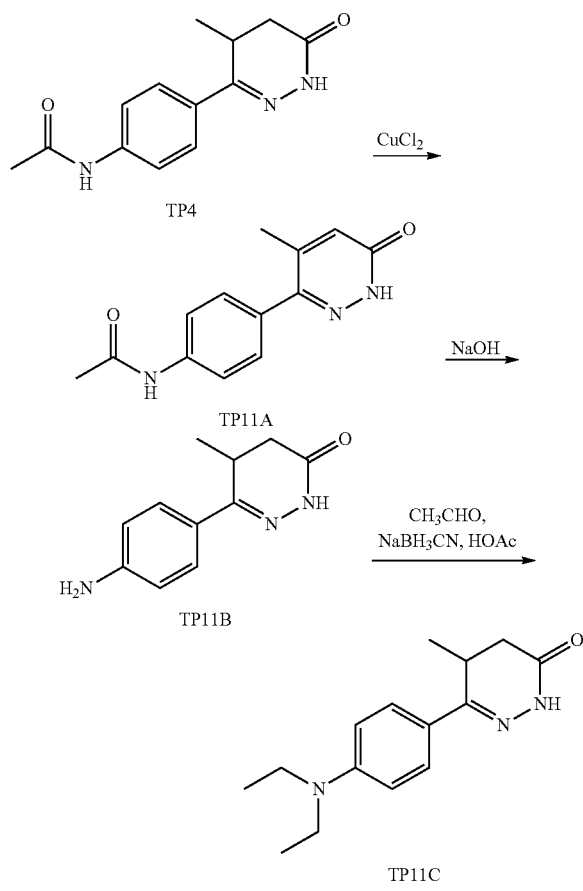

TP11A.
To 250 mg of TP4 (1.02 mmol, synthesized similarly to TP6 Int.) dissolved in 10 mL CH$_3$CN was added 350 mg of CuCl$_2$ hydrate (2.3 mmol) and the solution was heated at 80° C. for 1 h (*Bioorg Med Chem* 2002, 10, 2873-2882). After cooling the reaction was poured onto ice and the product was filtered and rinsed with water to produce 110 mg of product (44%). $^1$H NMR (300 MHz, DMSO-$d_6$) δ 13.02 (s, 1H), 10.11 (s, 1H), 7.67 (d, J=8.3, 2H), 7.41 (d, J=8.3, 2H), 6.82 (s, 1H), 3.39 (s, 3H), 2.08 (s, 3H). MS: 244 (M+1).

TP11B.
A solution of 100 mg TP11A (0.41 mmol) and 160 mg of NaOH (4.0 mmol) in 10 mL of EtOH was heated at reflux temperature overnight. After cooling, the clear liquid was decanted from a dark oil and concentrated. Water was added and rinsed several times with EtOAc, the combined EtOAc was dried and concentrated to give 50 mg of the product as an off-white solid (60%). $^1$H NMR (300 MHz, DMSO-$d_6$) δ 12.84 (s, 1H), 7.13 (d, J=8.4, 2H), 6.75 (s, 1H), 6.59 (d, J=8.4, 2H), 5.36 (s, 2H), 2.13 (s, 3H).

TP11C.
To a suspension of 40 mg of 11B (0.20 mmol) in 4 mL of MeOH was added 100 µL of acetaldehyde (1.8 mmol). To the solution was added 25 µL of HOAc (0.42 mmol) and 25 mg of NaBH$_3$CN (0.40 mmol) and the solution was stirred overnight. The next morning the same amounts of HOAc and NaBH$_3$CN were added, and after 4 h the solution was concentrated, water was added and rinsed several times with EtOAc, the combined EtOAc layers were dried, concentrated, and chromatographed with 50-100% EtOAc in hexane to isolate 39 mg of product as a yellow solid (61%). $^1$H NMR (300 MHz, CDCl$_3$) δ 12.01 (s, 1H), 7.24 (d, J=8.8, 2H), 6.97 (s, 1H), 6.65 (d, J=8.8, 2H), 3.38 (q, J=7.0, 4H), 2.23 (s, 3H), 1.18 (t, J=7.0, 6H). $^{13}$C NMR (75 MHz, CDCl$_3$/DMSO-$d_6$) δ 161.00, 148.44, 147.49, 143.65, 129.30, 127.91, 121.63, 110.52, 43.78, 20.26, 12.05. MS: 258 (M+1).

Synthesis of

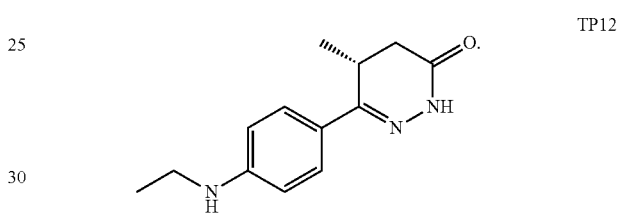

TP12.
To 200 mg of (R)-6-(4-aminophenyl)-5-methyl-4,5-dihydropyridazin-3(2H)-one (0.98 mmol) in 4 mL MeOH was added 43 mg of acetaldehyde (0.98 mmol) and 59 µL of HOAc (0.98 mmol) and the solution was stirred 2 h before concentration, dissolution in 4 mL MeOH, addition of 59 µL HOAc (0.98 mmol), 62 mg of NaBH$_3$CN (1.0 mmol) and stirring overnight. The solvent was removed, water was added and rinsed with EtOAc, the EtOAc was dried, concentrated and chromatographed with 30-50% EtOAc to give 19 mg of product as a white solid (8%). $^1$H NMR (300 MHz, CDCl$_3$) δ 8.77 (s, 1H), 7.60 (d, J=8.7, 2H), 6.60 (d, J=8.7, 2H), 3.92 (s, 1H), 3.38-3.26 (m, 1H), 3.20 (q, J=6.9, 2H), 2.68 (dd, J=6.7, 16.8, 1H), 2.43 (d, J=16.8, 1H), 1.26 (q, J=7.3, 6H). $^{13}$C NMR (75 MHz, CDCl$_3$) δ 166.82, 154.59, 149.79, 127.36, 122.91, 112.28, 38.12, 33.96, 27.89, 16.41, 14.73, 232 (M+1)

Synthesis of

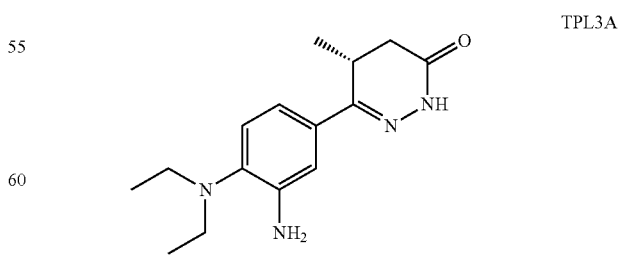

TPL3A.
To 36 mg of racemic 1B-1 (0.12 mmol) dissolved in 10 mL of MeOH was added 36 mg of 10% Pd on carbon wetted with MeOH. The mixture was placed under an H₂ atmosphere (balloon) for 1 h before filtering, concentration, and chromatography with 40-60% EtOAc in hexane to yield 21 mg of product as an off-white solid (65%). ¹H NMR (300 MHz, CDCl₃) δ 8.91 (s, 1H), 7.21 (d, J=1.9, 1H), 7.08 (dd, J=1.9, 8.2, 1H), 7.01 (d, J=8.2, 1H), 4.14 (s, 2H), 3.40-3.25 (m, 1H), 2.99 (q, J=7.1, 4H), 2.68 (dd, J=6.7, 16.9, 1H), 2.45 (d, J=16.8, 1H), 1.25 (d, J=7.3, 3H), 1.00 (t, J=7.1, 6H). ¹³C NMR (75 MHz, CDCl₃) δ 166.85, 154.51, 143.88, 139.22, 130.46, 122.57, 116.04, 112.07, 46.80, 33.95, 28.16, 16.40, 12.50. MS: 275 (M+1).

Synthesis of

TPL3B

TPL3B.

5 mg of TPL3A was dissolved in 2 mL acetic anhydride was stirred for 2 h before concentration to give 5 mg of the acetylated product. ¹H NMR (300 MHz, CDCl₃) δ 8.82 (s, 1H), 8.75 (s, 1H), 8.54 (s, 1H), 7.54 (d, J=8.4, 1H), 7.19 (d, J=8.4, 1H), 3.48-3.31 (m, 1H), 2.96 (q, J=7.1, 4H), 2.71 (dd, J=6.8, 17.0, 1H), 2.46 (d, J=17.1, 1H), 2.22 (s, 3H), 1.27 (d, J=7.4, 3H), 0.97 (t, J=7.1, 6H). MS: 317 (M+1).

Synthesis of

TP16

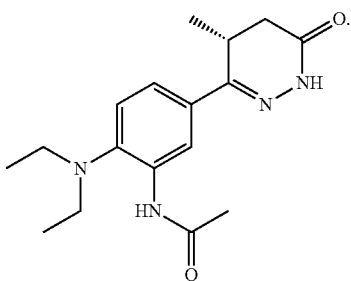

TP16.

To 0.19 mL (1.5 mmol) of boron trifluoride diethyl etherate pre-cooled to −15° C. was slowly added a solution of 200 mg of (R)-6-(4-aminophenyl)-5-methyl-4,5-dihydropyridazin-3(2H)-one (0.98 mmol) dissolved in 7 mL of THF. To this mixture, a solution of tert-butyl nitrite (0.16 mL, 1.2 mmol) in 1 mL of THF was added dropwise over 10 min. The reaction was stirred for 30 min at −15° C. before 40 mL of pentanes was added. The precipitate was collected by vacuum filtration and washed with hexanes and diethyl ether. Further drying under vacuum yielded the diazonium tetrafluoroborate salt as an orange solid. This material was used immediately without further purification.

The crude diazonium salt was placed under a constant stream of nitrogen and heated to 120° C. for 2 h. The material was cooled to room temperature and purified by chromatography with 0-5% MeOH in CH₂Cl₂ to yield 31 mg of the product as a white solid (15%). ¹H NMR (300 MHz, CDCl₃) δ 8.49 (s, 1H), 7.81-7.69 (m, 2H), 7.17-7.06 (m, 2H), 3.39-3.28 (m, 1H), 2.73 (dd, J=17.0, 6.8 Hz, 1H), 2.48 (dd, J=17.0, 0.9 Hz, 1H), 1.26 (d, J=7.4 Hz, 3H). ¹⁹F NMR (282 MHz, CDCl₃) δ −111.25 (tt, J=8.3, 5.3 Hz). MS: 207 (M+1).

Synthesis of

TP17

TP17.

To a suspension of 100 mg (0.49 mmol) of (R)-6-(4-aminophenyl)-5-methyl-4,5-dihydropyridazin-3(2H)-one in 7.6 mL of pyridine was added 130 mg of N,N'-diformylhydrazine (1.48 mmol). Next, 0.94 mL (7.4 mmol) of chlorotrimethylsilane was added dropwise followed by 0.48 mL (3.4 mmol) of Et₃N. The reaction was stirred overnight at 100° C. The reaction was cooled to room temperature then carefully added to 100 mL of a half-saturated solution of NaHCO₃. After exhaustive extraction with EtOAc, the combined extracts were dried, concentrated and chromatographed with 0-5% MeOH in CH₂Cl₂ to isolate 91 mg of product as a light yellow solid (73%). ¹H NMR (300 MHz, CDCl₃) δ 8.63 (s, 1H), 8.53 (s, 2H), 7.95 (d, J=8.7 Hz, 2H), 7.47 (d, J=8.7 Hz, 2H), 3.46-3.30 (m, 1H), 2.77 (dd, J=17.0, 6.9 Hz, 1H), 2.54 (dd, J=16.9, 0.9 Hz, 1H), 1.30 (d, J=7.4 Hz, 3H). MS: 256 (M+1).

Synthesis of

TP13

TP13.

To 100 mg (0.49 mmol) of (R)-6-(4-aminophenyl)-5-methyl-4,5-dihydropyridazin-3(2H)-one dissolved in 1 mL of DMF was added 250 mg K₂CO₃ and 100 uL of 1,5-dibromopentane (0.74 mmol), and the reaction was stirred overnight at 60° C. before cooling and addition of water. The mixture was rinsed several times with EtOAc, the combined EtOAc was dried, concentrated and chromatographed with 20-40% EtOAc in hexane to isolate 70 mg of product as a white solid (52%). ¹H NMR (300 MHz, CDCl₃) δ 8.70 (s, 1H), 7.64 (d, J=8.9, 2H), 6.91 (d, J=8.9, 2H), 3.42-3.15 (m, 5H), 2.69 (dd, J=6.7, 16.8, 1H), 2.44 (d, J=16.8, 1H), 1.79-1.52 (m, 6H), 1.24 (d, J=7.3, 3H). $^{13}$C NMR (75 MHz, CDCl$_3$) δ 166.72, 154.32, 152.74, 127.04, 123.89, 115.02, 49.39, 33.96, 27.90, 25.49, 24.33, 16.39.

Synthesis of

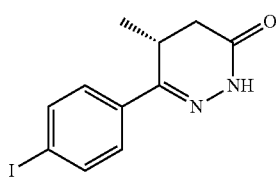

TP14.

A mixture of 2.0 g (9.8 mmol) of (R)-6-(4-aminophenyl)-5-methyl-4,5-dihydropyridazin-3(2H)-one) in 5 mL conc. HCl was cooled with an ice bath. Once cold, 0.75 g (11 mmol) of NaNO$_2$ dissolved in 3 mL of water was added slowly and stirred for 15 min. A solution of 16 g (98 mmol) of KI in 20 mL water was then added slowly. The solution turned dark, and foaming occurred. After 30 min, the mixture was rinsed several times with EtOAc, the combined EtOAc was rinsed with NaHCO$_3$, water, 5% sodium metabisulfite (aq), then dried, filtered, concentrated and chromatographed with 25-75% EtOAc in hexane to yield 1.5 g of orange solid which was clean enough for further use. A small amount was recrystallized from EtOAc to produce off-white crystals. $^1$H NMR (300 MHz, CDCl$_3$) δ 9.09 (s, 1H), 7.75 (d, J=8.5, 2H), 7.49 (d, J=8.5, 2H), 3.41-3.22 (m, 1H), 2.72 (dd, J=6.8, 17.0, 1H), 2.49 (d, J=16.9, 1H), 1.24 (d, J=7.4, 3H). $^{13}$C NMR (75 MHz, CDCl$_3$) δ 166.60, 152.96, 137.85, 134.00, 127.49, 96.14, 33.76, 27.82, 16.20. MS: 315 (M+1).

Synthesis of

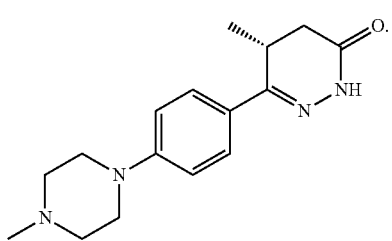

TP15.

A solution of 60 mg of TP14 (0.19 mmol) and 0.10 mL of 1-methylpiperazine (0.90 mmol) in 0.5 mL of NMP was heated at 160° C. for 4 h in a microwave apparatus (Biotage). Brine was added and the mixture was extracted with EtOAc, the EtOAc was dried, concentrated and chromatographed with 0-5% MeOH in CH$_2$Cl$_2$ to isolate 10 mg of product as a white solid (20%). $^1$H NMR (300 MHz, CDCl$_3$) δ 8.72 (s, 1H), 7.66 (d, J=9.0, 2H), 6.92 (d, J=9.0, 2H), 3.45-3.17 (m, 5H), 2.69 (dd, J=6.7, 16.9, 1H), 2.62-2.52 (m, 4H), 2.44 (d, J=16.8, 1H), 2.36 (s, 3H), 1.23 (d, J=7.4, 3H).

Synthesis of

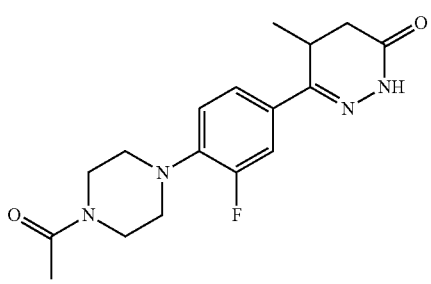

TP39.

A mixture of 26 mg of TP29 (0.12 mmol) in 1.5 mL of N-acetyl piperazine (12 mmol) was heated at 140° C. for 2 h. After cooling, 10 mL of water was added and was rinsed several times with EtOAc, the combined EtOAc layers were rinsed with water and brine, dried, concentrated and chromatographed with 0-5% MeOH in CH$_2$Cl$_2$ to yield 23 mg of product as an off-white solid (58%). $^1$H NMR (300 MHz, CDCl$_3$) δ 8.71 (s, 1H), 7.52 (dd, J=1.8, 14.2, 1H), 7.43 (d, J=8.4, 1H), 6.92 (t, J=8.6, 1H), 3.86-3.75 (m, 2H), 3.71-3.60 (m, 2H), 3.36-3.22 (m, 1H), 3.21-3.04 (m, 4H), 2.71 (dd, J=6.8, 16.9, 1H), 2.47 (d, J=16.8, 1H), 2.15 (s, 3H), 1.24 (d, J=7.4, 3H). $^{19}$F NMR (282 MHz, CDCl$_3$) δ −121.47 (dd, J=8.9, 14.2). MS: 333 (M+1).

Dimethylpyrazolone Syntheses—

Certain compounds were made according to the following scheme.

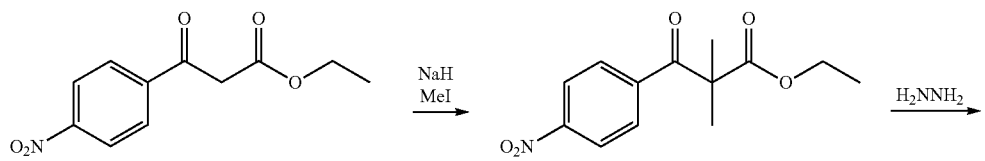

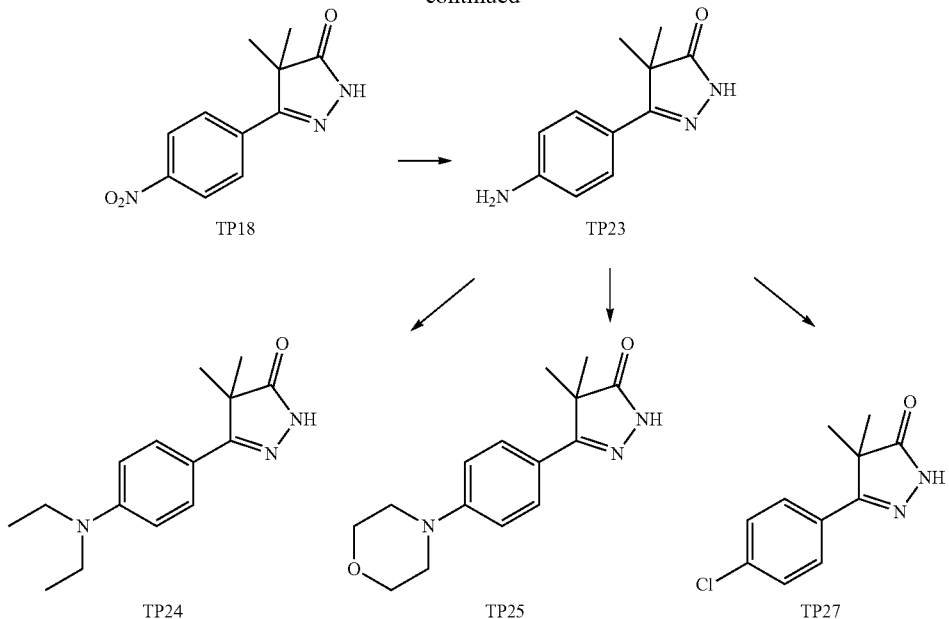

Ethyl 2,2-dimethyl-3-(4-nitrophenyl)-3-oxopropanoate. To 3.71 g of 60% NaH oil dispersion (92.8 mmol) in 15 mL of dry DMF was added a solution of 10.0 g of ethyl 3-(4-nitrophenyl)-3-oxopropanoate (42.2 mmol) and 5.25 mL of methyl iodide dissolved in 50 mL of dry THF and the mixture was stirred overnight (Eur. Pat. Appl. 0223937, Jun. 3, 1987). Saturated NH4Cl solution was added and the mixture rinsed several times with ether, the combined ether layers were rinsed with brine, dried, concentrated and chromatographed with 0-10% EtOAc in hexane to produce 4.50 g of product as an off white solid which was sufficiently pure for the next step (40%). 1H NMR (300 MHz, CDCl3) δ 8.28 (d, J=9.0, 2H), 7.99 (d, J=9.0, 2H), 4.14 (q, J=7.1, 2H), 1.57 (s, 6H), 1.09 (t, J=7.1, 3H). MS: 266 (M+1).

4,4-Dimethyl-3-(4-nitrophenyl)-1H-pyrazol-5(4H)-one (TP18). A solution of 4.50 g of ethyl 2,2-dimethyl-3-(4-nitrophenyl)-3-oxopropanoate (17.0 mmol) and 4.2 mL of hydrazine hydrate (87 mmol) in 50 mL EtOH was heated at reflux for 2 h before cooling and concentration. Water was added and rinsed several times with EtOAc, the combined EtOAc was dried, concentrated, and chromatographed with 30-50% EtOAc in hexane to yield 2.54 g of product as a yellow solid (64%). $^1$H NMR (300 MHz, DMSO-$d_6$) δ 11.92 (s, 1H), 8.26 (d, J=9.0, 2H), 8.07 (d, J=9.0, 2H), 1.40 (s, 6H). $^{13}$C NMR (75 MHz, DMSO-$d_6$) δ 180.74, 159.68, 147.47, 136.63, 126.79, 124.02, 46.25, 21.54. MS: 234 (M+1).

3-(4-Aminophenyl)-4,4-dimethyl-1H-pyrazol-5(4H)-one (TP23). To a solution of 1.05 g (4.50 mmol) of TP18 in 100 mL EtOH was added 250 mg of 10% Pd on carbon and the mixture was stirred under a $H_2$ atmosphere (balloon) for 2 h before filtration and concentration to give 857 mg off the product as an off-white solid (94%). $^1$H NMR (300 MHz, CDCl$_3$) δ 10.44 (s, 1H), 7.59 (d, J=8.7, 2H), 6.68 (d, J=8.7, 2H), 4.35 (s, 2H), 1.46 (d, J=5.1, 6H). $^{13}$C NMR (75 MHz, CDCl$_3$) δ 181.36, 163.01, 148.64, 127.35, 120.66, 114.37, 46.95, 22.53. MS: 204 (M+1).

3-(4-(Diethylamino)phenyl)-4,4-dimethyl-1H-pyrazol-5 (4H)-one (TP24). To a solution of 130 mg of TP23 (0.64 mmol) in 5 mL of MeOH was added 80 mg (1.3 mmol) of NaBH$_3$CN and 52 µL of HOAc (1.3 mmol). After stirring 3 h the same amounts of NaBH$_3$CN and HOAc were added. After stirring an additional 2 h, the mixture was concentrated, EtOAc was added and rinsed with water, the EtOAc was dried, concentrated and chromatographed with 20-40% EtOAc in hexane before recrystallization from EtOAc/hexane to produce 93 mg of white solid (56%). $^1$H NMR (300 MHz, CDCl$_3$) δ 8.62 (s, 1H), 7.67 (d, J=9.1, 2H), 6.67 (d, J=9.1, 2H), 3.40 (q, J=7.1, 4H), 1.51 (s, 6H), 1.20 (t, J=7.1, 6H). $^{13}$C NMR (75 MHz, CDCl$_3$) δ 181.20, 163.90, 148.86, 127.65, 117.70, 111.09, 47.02, 44.37, 22.81, 12.57. MS: 260 (M+1).

4,4-Dimethyl-3-(4-morpholinophenyl)-1H-pyrazol-5 (4H)-one (TP25). A mixture of 100 mg (0.49 mmol) of TP23, 200 mg (1.45 mmol) of $K_2CO_3$ and 250 µL of 1-bromo-2-(2-bromoethoxy)ethane (2.00 mmol) were heated overnight at 60° C. Water and EtOAc were added after cooling, the water was rinsed several times with EtOAc, the combined EtOAc layers were rinsed with brine, dried, concentrated and chromatographed with 0-2% MeOH in CH$_2$Cl$_2$ to isolate 44 mg of product as an off-white solid (33%).

$^1$H NMR (300 MHz, CDCl$_3$) δ 8.85 (s, 1H), 7.72 (d, J=9.0, 2H), 6.92 (d, J=9.0, 2H), 3.99-3.80 (m, 4H), 3.35-3.13 (m, 4H), 1.51 (s, 6H). $^{13}$C NMR (75 MHz, CDCl$_3$) δ 181.51, 163.34, 152.10, 127.39, 122.05, 114.69, 66.67, 48.20, 47.20, 22.61. MS: 274 (M+1).

3-(4-Chlorophenyl)-4,4-dimethyl-1H-pyrazol-5(4H)-one (TP26). To a cooled (ice bath) solution of 100 mg of TP23 (0.49 mmol) in 1 mL conc. HCl was added a solution of 34 mg of NaNO$_2$ dissolved in 0.5 mL water (0.49 mmol). After stirring cold for 30 min, this solution was added dropwise to a cold solution of 49 mg of CuCl dissolved in 1 mL water and 0.5 mL conc. HCl. The ice bath was removed and the reaction stirred 1 h before rinsing twice with EtOAc, and rinsing the combined EtOAc with sat'd NaHCO$_3$ solution. Drying, concentrating and chromatography with 0-40% EtOAc in hexane yielded 79 mg of product as a white solid (72%). $^1$H NMR (300 MHz, CDCl$_3$) δ 9.50 (s, 1H), 7.74 (d, J=8.5, 2H), 7.41 (d, J=8.5, 2H), 1.51 (s, 6H). $^{13}$C NMR (75

MHz, CDCl₃) δ 181.35, 162.34, 136.10, 129.49, 129.11, 127.43, 47.17, 22.35. MS: 223 (M+1).

Synthesis of

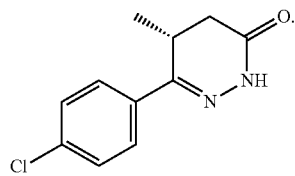

TP26

TP26.

A solution of 167 mg of (R)-6-(4-aminophenyl)-5-methyl-4,5-dihydropyridazin-3(2H)-one (0.822 mmol) in 1 mL of concentrated HCl was cooled on an ice bath before the slow addition of 56.7 mg of NaNO₂ (0.822 mmol) in 0.5 mL water. After stirring 30 min, the solution was added to an ice-cold solution of 81.0 mg of CuCl (0.822 mmol) dissolved in a mixture of 1 mL of water and 0.5 mL of concentrated HCl. After warming to room temperature and stirring 90 min, the mixture was transferred to a separatory funnel and rinsed several times with CH₂Cl₂. The combined CH₂Cl₂ layers were rinsed with brine, dried, concentrated and chromatographed with 20-50% EtOAc in hexane to yield 141 mg of product (77%). ¹H NMR (300 MHz, CDCl₃) δ 8.96 (s, 1H), 7.70 (d, J=7.4, 2H), 7.39 (d, J=7.4, 2H), 3.56-3.08 (m, 1H), 2.73 (dd, J=6.4, 16.7, 1H), 2.49 (d, J=16.8, 1H), 1.25 (d, J=6.4, 3H). ¹³C NMR (75 MHz, CDCl₃) δ 166.73, 152.84, 135.90, 133.00, 128.95, 127.22, 33.80, 28.00, 16.23. Mass 223 (M+1).

Synthesis of TP29 and TP30 were made according to the following scheme.

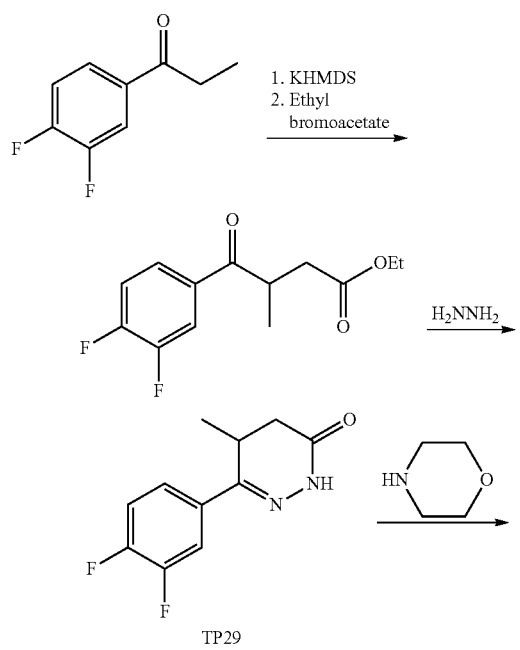

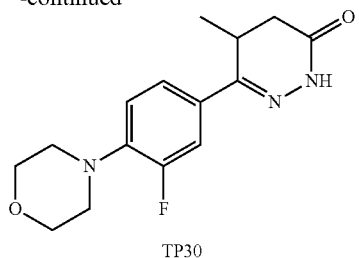

TP30

Following a literature procedure (*J. Org. Chem.* 1987, 52, 304), to 24 mL of a 1.0 M LiHMDS solution (THF), cooled to −78° C., was added 30 mL THF. After 10 min a solution of 4.0 g of 3,4-difluoropropiophenone (24 mmol) in 15 mL THF was added slowly. After stirring 1 h cold, a solution of 5.0 g of ethyl bromoacetate (30 mmol) in 10 mL THF was added slowly before warming to 0° C. After 1 h, the reaction was quenched with 1 N HCl (aq), and rinsed several times with EtOAc. The combined organic layers were rinsed with brine, dried, concentrated and chromatographed with 0-10% EtOAc to isolate 1.8 g of product as a clear liquid (30%). ¹H NMR (300 MHz, CDCl₃) δ 7.77-7.84 (m, 2H), 7.32-7.24 (m, 1H), 4.10 (q, J=7.2, 2H), 3.92-3.77 (m, 1H), 2.97 (dd, J=9.0, 16.9, 1H), 2.46 (dd, J=5.2, 17.0, 1H), 1.23 (t, J=7.2, 3H), 1.20 (d, J=4.1, 2H). ¹⁹F NMR (CDCl₃) δ −129.80 to −129.95 (m, 1F), −136.09 to −135.95 (m, 1F).

6-(3,4-Difluorophenyl)-5-methyl-4,5-dihydropyridazin-3 (2H)-one (TP29). Following a literature procedure (Eur. Pat. Appl. 0223937, Jun. 3, 1987) a solution of 5 mL EtOH, 260 mg of ethyl 4-(3,4-difluorophenyl)-3-methyl-4-oxobutanoate (1.02 mmol) and 320 μL of hydrazine hydrate (6.6 mmol) was heated at reflux temperature for 2 h. The solution was concentrated, water was added and rinsed several times with EtOAc, the combined EtOAc layers were rinsed with water, brine, and dried, concentrated and chromatographed with 10-30% EtOAc in hexane to isolate 66 mg of product as a white solid (29%). The solid was recrystallized from EtOAc to give white crystals. ¹H NMR (300 MHz, CDCl₃) δ 9.36 (s, 1H), 7.65 (ddd, J=1.9, 7.7, 11.6, 1H), 7.55-7.39 (m, 1H), 7.20 (dd, J=8.6, 18.0, 1H), 3.30 (p, J=7.1, 1H), 2.74 (dd, J=6.9, 17.0, 1H), 2.51 (d, J=16.9, 1H), 1.26 (d, J=7.4, 3H). ¹⁹F NMR (282 MHz, CDCl₃) δ −135.14 to −135.48 (m, 1F), −136.39 to −136.66 (m, 1F). ¹³C NMR (75 MHz, CDCl₃) δ 166.62, 152.57 (dd, J=12.7, 58.9), 151.76 (t, J=2.1), 149.25 (dd, J=12.7, 54.9), 131.72 (dd, J=3.85, 1.98), 122.14 (dd, J=3.5, 6.5), 117.41 (d, J=17.6), 115.06 (d, J=18.9), 33.69, 27.97, 16.14. Elem. Calcd. for C₁₁H₁₀F₂N₂O: C, 58.93; H, 4.50; N, 12.49. Found C, 58.67; H, 4.23; N, 12.37.

6-(3-Fluoro-4-morpholinophenyl)-5-methyl-4,5-dihydro-pyridazin-3(2H)-one (TP30). A solution of 100 mg of TP29 (0.45 mmol) dissolved in 15 mL of morpholine was heated at 120° C. for 2 d. After cooling, the reaction was concentrated, water was added and rinsed several times with EtOAc, the combined EtOAc layers were rinsed with brine, dried, concentrated, and chromatographed with 30-70% EtOAc in hexane to yield 69 mg of off white solid (53%). The material was recrystallized with EtOAc/hexane to yield 50 mg of white solid. ¹H NMR (300 MHz, CDCl₃) δ 8.46 (s, 1H), 7.50 (dd, J=2.1, 14.4, 1H), 7.43 (dd, J=1.8, 8.4, 1H), 6.93 (t, J=8.7, 1H), 3.95-3.83 (m, 4H), 3.37-3.23 (m, 1H), 3.21-3.11 (m, 4H), 2.70 (dd, J=6.8, 16.9, 1H), 2.47 (d, J=17.1, 1H), 1.24 (d, J=7.4, 3H). $^{13}$C NMR (75 MHz, CDCl$_3$) δ 166.45, 155.33 (d, $J_{C-F}$=246.3), 152.71, 141.1 (d, $J_{C-F}$=8.6), 128.75 (d, $J_{C-F}$=7.6), 122.20 (d, $J_{C-F}$=3.0), 118.09 (d, $J_{C-F}$=3.6), 113.80 (d, $J_{C-F}$=23.0), 66.83, 50.50 (d, $J_{C-F}$=3.9), 33.84, 27.96, 16.29. $^{19}$F NMR (282 MHz, CDCl$_3$) δ 121.47 (dd, J=8.9, 14.4, 1F). Anal. Calcd. for C$_{15}$H$_{18}$FN$_3$O$_2$: C, 61.84; H, 6.23; N, 14.42. Found: C, 61.76; H, 5.96; N, 14.33.

Stereochemistry of TP29 and TP30 active isomers. Isomers of compounds TP29 and TP30 were separated by supercritical fluid chromatography (SCF). Analytical SCF of the returned samples (Column: ChiralPak AS-H, 250×4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C.) showed that all samples were enantiomerically pure. All individual samples were tested in the HeLa assay and in both cases the isomer with the longer retention time on the SFC was active while the more quickly eluted isomers were inactive. The more quickly eluted isomer (inactive) of TP29 was converted to the more quickly eluted isomer (inactive) of TP30 by overnight refluxing in morpholine with no apparent epimerization, hence inactive TP29 and TP30 have the same stereochemistry as does active TP29 and TP30.

Racemic TP5 was prepared using racemic amine. The enantiomers are separated by analytical chiral SFC, the R-isomer, synthesized from the R-starting material, having the longer retention time. Defluorination of the inactive TP30 under reductive conditions (10% Pd/C, MeOH, H$_2$ gas) produced only the S-isomer of TP5 as determined with SFC chromatography, hence the active isomers of all three compounds have the R-configuration. The compounds were made according to the following scheme.

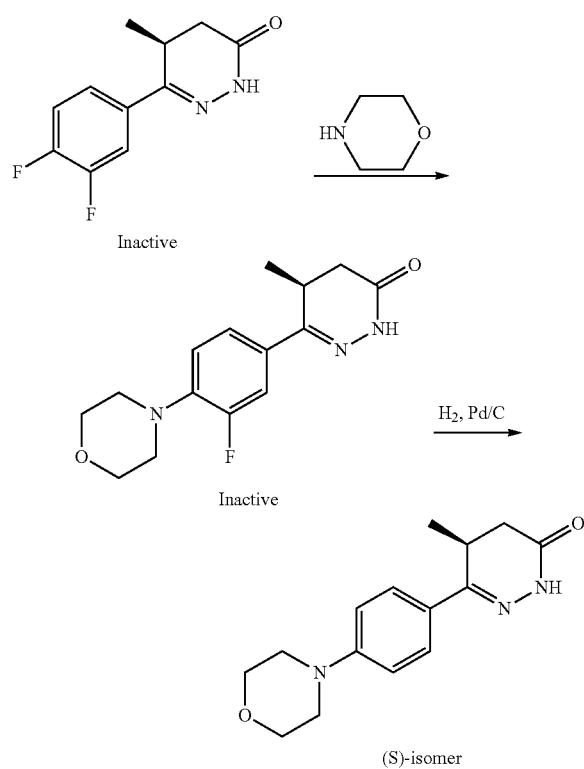

Synthesis of

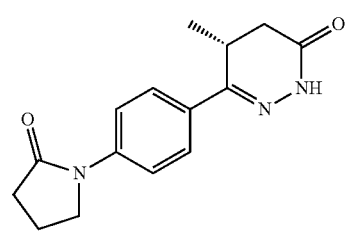

TP20.

To 100 mg of (R)-6-(4-aminophenyl)-5-methyl-4,5-dihydropyridazin-3(2H)-one (0.49 mmol) dissolved in 2 mL of CHCl$_3$ and cooled to 0° C. was added DIPEA (0.43 mL, 2.5 mmol) followed by 4-chlorobutanoyl chloride (60 L, 0.54 mmol). The reaction was stirred at 0° C. for 1.5 h before heating to 60° C. and stirring overnight. After cooling, NaHCO$_{3(aq)}$ was added and was extracted with CH$_2$Cl$_2$. LC analysis indicated a 1:1 ratio of starting material to intermediate chloride. The crude material was then dissolved in 7 mL of CH$_2$Cl$_2$ and to this was added 0.2 mL DIPEA (1.2 mmol) and 4-chlorobutanoyl chloride (60 μL, 0.54 mmol). After 30 min, the reaction was worked up as before, the crude product chromatographed with 0-25% EtOAc in hexane to produce 92 mg of impure compound. This material was dissolved in 6 mL of DMF and 124 mg of K$_2$CO$_3$ (0.90 mmol) was added and the mixture was heated at 60° C. for 5 h. After cooling, water was added and was rinsed several times with EtOAc, the combined EtOAc layers were rinsed with brine, dried, concentrated, and chromatographed with 0-25% EtOAc in hexane to produce 38 mg of product as an off-white solid (47%). $^1$H NMR (300 MHz, CDCl$_3$) δ 8.47 (s, 1H), 7.77 (d, J=9.0, 2H), 7.71 (d, J=9.1, 2H), 3.90 (t, J=7.0, 2H), 3.45-3.29 (m, 1H), 2.73 (dd, J=6.8, 16.9, 1H), 2.65 (t, J=8.1, 2H), 2.48 (d, J=16.8, 1H), 2.27-2.13 (m, 2H), 1.25 (d, J=7.4, 3H). $^{13}$C NMR (75 MHz, CDCl$_3$) δ 174.35, 166.75, 153.25, 140.58, 130.04, 126.36, 119.31, 48.39, 33.70, 32.65, 27.76, 17.74, 16.13. MS: 272 (M+1).

Synthesis of

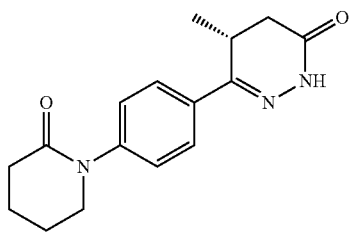

TP21.

To 50 mg of (R)-6-(4-aminophenyl)-5-methyl-4,5-dihydropyridazin-3(2H)-one (0.25 mmol) dissolved in 2.0 mL THF and cooled to 0° C. was added 51 μL of triethylamine (0.37 mmol) and 5-chlorovaleryl chloride (35 μL, 0.27 mmol). The reaction was stirred while slowly warming to room temperature. After 30 min, the reaction mixture was filtered over Celite and concentrated. The crude material was dissolved in 6 mL of DMF, 102 mg of K$_2$CO$_3$ (0.74 mmol) was added before heating at 60° C. for 3 h. After cooling, water was added and rinsed several times first with EtOAc and then with 1:9 MeOH:CH$_2$Cl$_2$. The combined organic washes were dried, concentrated, and chromatographed with 0-35% EtOAc in hexane to yield 68 mg of product (97%). ¹H NMR (300 MHz, CDCl₃) δ 9.42 (s, 1H), 7.79 (d, J=8.7, 2H), 7.33 (d, J=8.7, 2H), 3.66 (d, J=5.4, 2H), 3.34 (p, J=7.3, 1H), 2.69 (dd, J=6.8, 16.9, 1H), 2.59 (t, J=6.0, 2H), 2.46 (d, J=16.9, 1H), 2.02-1.89 (m, 4H), 1.24 (d, J=7.4, 3H). ¹³C NMR (75 MHz, CDCl₃) δ 169.97, 166.70, 153.08, 144.46, 132.44, 126.50, 125.97, 51.12, 33.70, 32.78, 27.81, 23.32, 21.21, 16.04. MS: 286 (M+1).

Synthesis of

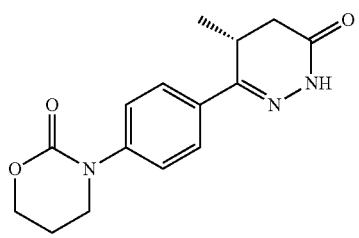

TP22.

To 50 mg of (R)-6-(4-aminophenyl)-5-methyl-4,5-dihydropyridazin-3(2H)-one (0.25 mmol) dissolved in 2 mL of THF and cooled to 0° C. was added triethylamine (51 μL, 0.37 mmol) and 3-chloropropyl chloroformate (33 μL, 0.27 mmol). The reaction was stirred while slowly warming to room temperature. After 1 h another 10 μL of chloroformate was added, after 3 h the reaction mixture was filtered over Celite and concentrated. The crude material was dissolved in 4 mL of DMF, 102 mg of K₂CO₃ (0.74 mmol) was added before heating at 60° C. for 2.5 h. After cooling, water was added and rinsed several times first with EtOAc and then with 1:9 MeOH: CH₂Cl₂. The combined organic washes were dried, concentrated, and chromatographed with 0-40% EtOAc in hexane to yield 47 mg of product (66%). ¹H NMR (300 MHz, CDCl₃) δ 9.12 (s, 1H), 7.79 (d, J=8.8, 2H), 7.41 (d, J=8.8, 2H), 4.51-4.37 (m, 2H), 3.76 (t, J=6.1, 2H), 3.35 (p, J=7.3, 1H), 2.71 (dd, J=6.8, 16.9, 1H), 2.48 (dd, J=1.0, 17.0, 1H), 2.31-2.14 (m, 2H), 1.24 (d, J=7.4, 3H). ¹³C NMR (75 MHz, CDCl₃) δ 166.65, 153.11, 152.40, 144.14, 132.52, 126.65, 125.52, 66.99, 48.28, 33.75, 27.92, 22.40, 16.12, 288 (M+1).

Synthesis of

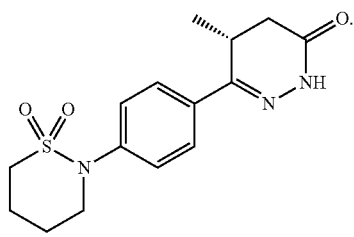

TP28.

To 50 mg of (R)-6-(4-aminophenyl)-5-methyl-4,5-dihydropyridazin-3(2H)-one (50 mg, 0.25 mmol) dissolved in 2 mL of THF was added 51 μL triethylamine (0.37 mmol) and 4-chlorobutane-1-sulfonyl chloride (39 μL, 0.27 mmol). The reaction was stirred at room temperature for 1 h before filtering over Celite and concentration. The crude material was dissolved in 4 mL of DMF, 102 mg of K₂CO₃ (0.74 mmol) was added before heating at 60° C. overnight. After cooling, the solvent was thoroughly removed by rotary evaporation followed by azeotroping with toluene. Water was added and was rinsed with EtOAc and CH₂Cl₂, the organic layers were dried, concentrated and chromatographed with 0-50% EtOAc to isolate 68 mg of product as an off-white solid (86%). ¹H NMR (300 MHz, CDCl₃) δ 8.57 (s, 1H), 7.75 (d, J=8.8, 2H), 7.39 (d, J=8.8, 2H), 3.86-3.67 (m, 2H), 3.42-3.27 (m, 1H), 3.27-3.14 (m, 2H), 2.71 (dd, J=6.8, 16.9, 1H), 2.48 (d, J=16.0, 1H), 2.42-2.27 (m, 2H), 1.93 (dt, J=5.9, 11.6, 2H), 1.25 (d, J=7.4, 3H). ¹³C NMR (75 MHz, CDCl₃) δ 166.41, 153.14, 141.83, 133.17, 126.71, 126.67, 77.42, 77.00, 76.58, 53.26, 50.75, 33.87, 28.08, 24.52, 24.21, 16.21, 322 (M+1).

Synthesis of

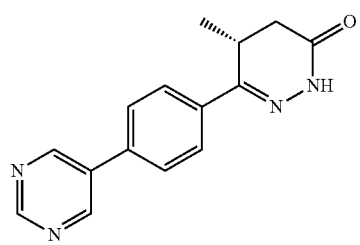

TP38.

To 27.6 mg of TP14 (0.088 mmol) and 33 mg of 5-pyrimidine boronic acid (0.26 mmol) dissolved in 0.65 mL of 1,4-dioxane was added 0.20 mL of a 2.0 M aqueous solution of Na₂CO₃ (0.40 mmol) and the mixture was sparged with nitrogen for 5 min. Tetrakis(triphenylphosphine)palladium (0) (10 mg, 8.8 μmol) was added and the reaction was sparged for another minute before the vial was sealed under nitrogen and heated at 60° C. overnight. An additional 10 mg of catalyst was added and the reaction was heated at 60° C. for 2 more days. Water was added and rinsed several times with EtOAc, the combined EtOAc layers were dried, concentrated and chromatographed with 0-40% EtOAc to produce 22 mg of yellow solid. Dissolution in CH₂Cl₂ and treatment with charcoal produced 16 mg of white solid (68%). ¹H NMR (300 MHz, CDCl₃) δ 9.24 (s, 1H), 9.00 (s, 2H), 8.64 (s, 1H), 7.93 (d, J=8.5, 2H), 7.66 (d, J=8.6, 2H), 3.42 (pd, J=1.6, 7.3, 1H), 2.77 (dd, J=6.8, 17.0, 1H), 2.53 (d, J=16.1, 1H), 1.31 (d, J=7.4, 3H). ¹³C NMR (75 MHz, CDCl₃) δ 166.37, 157.86, 154.81, 152.91, 135.52, 135.18, 133.48, 127.26, 126.92, 33.87, 28.09, 16.29. MS 267 (M+1).

Synthesis of

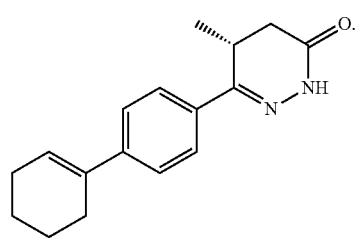

TP40.

To 40 mg of TP14 (0.13 mmol) and 48 mg of 1-cyclohexenylboronic acid (0.38 mmol) in 0.9 mL of 1,4-dioxane was added 0.29 mL of a 2.0 M aqueous solution of Na₂CO₃ (0.57 mmol) and the mixture was sparged with nitrogen for 5 min. Tetrakis(triphenylphosphine)palladium(0) (14.7 mg, 0.013 mmol) was added, and the reaction was sparged for another minute before the vial was sealed under nitrogen and heated to 60° C. for 24 h. After cooling, the reaction was diluted with water and rinsed several times with EtOAc, the combined EtOAc layers were dried, concentrated, and chromatographed with 0-30% EtOAc in hexane to give a tan solid which was dissolved in MeOH, treated with charcoal, filtered and concentrated to yield 31 mg of white solid (90%). $^1$H NMR (500 MHz, CDCl$_3$) δ 9.14 (s, 1H), 7.73 (d, J=8.5, 2H), 7.45 (d, J=8.5, 2H), 6.24 (s, 1H), 3.47-3.29 (m, 1H), 2.73 (dd, J=6.9, 16.9, 1H), 2.50 (d, J=16.7, 1H), 2.44 (dd, J=6.0, 7.8, 2H), 2.25 (dd, J=2.4, 6.1, 2H), 1.86-1.76 (m, 2H), 1.76-1.63 (m, 2H), 1.27 (d, J=7.4, 3H). $^{13}$C NMR (126 MHz, CDCl$_3$) δ 166.88, 153.90, 143.96, 135.72, 132.36, 126.01, 125.73, 125.02, 33.80, 27.88, 27.08, 25.89, 22.87, 21.97, 16.25. MS 269 (M+1).

Synthesis of

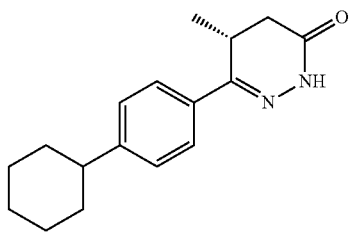

TP42.

To 24.1 mg of TP40, 0.090 mmol) was added 3.0 mg of palladium (10% wt) on activated carbon and the reaction flask was purged with nitrogen. Ethanol, 1 mL, was the added and the flask was purged with hydrogen, and the reaction was stirred under a hydrogen atmosphere (balloon). After 6 h, the mixture was filtered over Celite with MeOH, the solvents were removed and chromatography with 0-8% MeOH in CH$_2$Cl$_2$ yielded 15.3 mg of product as a white solid (63%). $^1$H NMR (500 MHz, CDCl$_3$) δ 8.81 (s, 1H), 7.71 (d, J=8.3, 2H), 7.28 (d, J=8.3, 2H), 3.42-3.32 (m, 1H), 2.72 (dd, J=6.8, 16.9, 1H), 2.61-2.52 (m, 1H), 2.49 (d, J=16.9, 1H), 1.87-1.92 (m, 4H), 1.52-1.35 (m, 6H), 1.28 (d, J=7.4, 4H). $^{13}$C NMR (126 MHz, CDCl$_3$) δ 167.03, 154.45, 150.49, 132.27, 127.48, 126.14, 44.65, 34.50, 34.49, 34.16, 28.32, 27.04, 26.33, 16.55. MS 271 (M+1).

Synthesis of

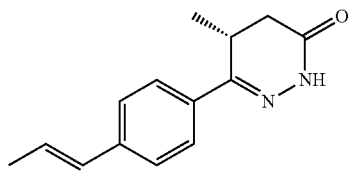

TP41.

To 0.9 mL dioxane was added 40 mg of TP14 (0.13 mmol) and 33 mg of (E)-prop-1-enylboronic acid (0.38 mmol) in a 4 mL vial. A 2.0 M aqueous solution of Na$_2$CO$_3$ (0.29 ml, 0.57 mmol) was then added and the mixture was sparged with nitrogen for 5 min. Tetrakis(triphenylphosphine)palladium(0) (14.7 mg, 0.013 mmol) was added, and the reaction was sparged 1 min before the vial was sealed under nitrogen and heated at 60° C. for 24 h. After cooling, the reaction was diluted with water and rinsed several times with EtOAc, the combined EtOAc layers were dried, concentrated, and chromatographed with 0-30% EtOAc in hexane to give a tan solid. This material was dissolved in MeOH and filtered through activated carbon. The filtrate was concentrated under reduced pressure to give 19 mg of product as an off-white solid (65%). $^1$H NMR (500 MHz, CDCl$_3$) δ 9.01 (s, 1H), 7.71 (d, J=8.4, 2H), 7.39 (d, J=8.4, 2H), 6.44 (d, J=15.9, 1H), 6.40-6.29 (m, 1H), 3.42-3.32 (m, 1H), 2.73 (dd, J=6.9, 16.9, 1H), 2.50 (d, J=16.8, 1H), 1.93 (d, J=6.4, 3H), 1.27 (d, J=7.4, 3H). $^{13}$C NMR (126 MHz, CDCl$_3$) δ 166.83, 153.86, 139.45, 132.60, 130.28, 127.36, 126.04, 126.03, 33.81, 27.90, 18.59, 16.27. MS 229 (M+1).

Synthesis of

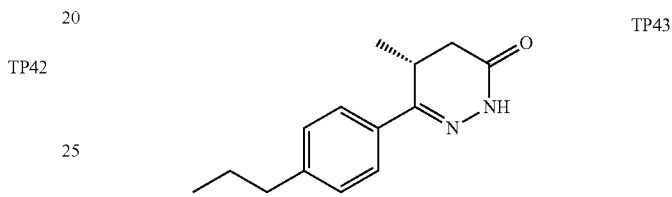

TP43.

To 14 mg of TP41 (0.061 mmol) was added 3 mg palladium on activated carbon (10% wt) and the reaction flask was purged with nitrogen. Ethanol, 1 mL, was the added. The flask was purged with hydrogen, and the reaction was stirred under a hydrogen atmosphere for 6 h before filtering over Celite with MeOH. Concentration and chromatography with 0-10% MeOH in DCM yield 8.4 mg of product as a white solid (60%). $^1$H NMR (500 MHz, CDCl$_3$) δ 8.73 (s, 1H), 7.70 (d, J=8.3, 2H), 7.25 (d, J=8.2, 2H), 3.45-3.29 (m, 1H), 2.73 (dd, J=6.8, 16.9, 1H), 2.70-2.58 (m, 2H), 2.49 (d, J=16.8, 1H), 1.78-1.56 (m, 2H), 1.28 (d, J=7.4, 3H), 0.97 (t, J=7.3, 3H). $^{13}$C NMR (126 MHz, CDCl$_3$) δ 166.71, 154.20, 144.89, 131.88, 128.85, 125.79, 37.76, 33.88, 28.06, 24.33, 16.28, 13.76. MS 231 (M+1).

Synthesis of

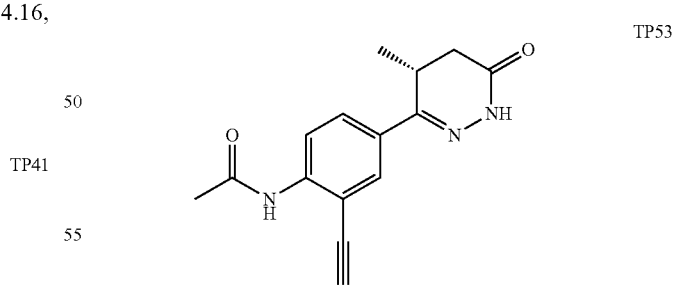

TP53.

To a 5 mL microwave tube was added 100 mg of TP10A, (0.31 mmol) and 7.1 mg of tris(dibenzylideneacetone)dipalladium(0) (7.7 μmol), 1.9 mg CuI (10 μmol), and 9.3 mg of PPh$_3$ 0.035 mmol). The tube was vacuum purged with nitrogen three times before adding 4 mL of triethylamine. The resulting suspension was sparged with nitrogen before adding 0.26 mL of ethynyltrimethylsilane (1.9 mmol). The tube was sealed under nitrogen, heated to 70° C. and stirred overnight. The reaction was cooled to room temperature then filtered through a cotton plug. The filtrate was concentrated under reduced pressure to give a yellow foam which was chromatographed with 0-25% EtOAc in CH$_2$Cl$_2$ to isolate 84 mg of product (80%). $^1$H NMR (300 MHz, CDCl$_3$) δ 9.17 (s, 1H), 8.21 (d, J=8.8, 1H), 7.85 (s, 1H), 7.60 (d, J=1.8, 1H), 7.48 (d, J=8.8, 1H), 3.18-2.95 (m, 1H), 2.46 (dd, J=6.8, 16.9, 1H), 2.22 (d, J=16.8, 1H), 1.99 (s, 3H), 0.98 (d, J=7.3, 3H), 0.26 (s, 9H). MS 342 (M+1).

The silyl alkyne, 30 mg (0.088 mmol) was dissolved in 0.8 mL THF and to this was added 0.13 mL of 1.0 N TBAF in THF (0.13 mmol). After 3 h another 0.1 mL of TBAF solution was added. After a total of 6 h, the reaction was cooled to 0° C. and carefully quenched with saturated NaHCO$_3$ solution (aqueous, 2 mL). The reaction was diluted with ethyl acetate and the layers were separated. The aqueous phase was extracted with EtOAc (3×2 mL) and the combined organic layers were dried, concentrated and chromatographed with 0-40% EtOAc in CH$_2$Cl$_2$ to give 12 mg of TP53 as a pale yellow solid (52%). $^1$H NMR (300 MHz, CDCl$_3$) δ 8.78 (s, 1H), 8.49 (d, J=8.8, 1H), 7.99 (s, 1H), 7.89 (d, J=2.0, 1H), 7.74 (d, J=8.9, 1H), 3.56 (s, 1H), 3.32 (p, J=7.2, 1H), 2.72 (dd, J=6.8, 17.0, 1H), 2.48 (d, J=16.3, 1H), 2.26 (s, 3H), 1.24 (d, J=7.4, 3H). $^{13}$C NMR (75 MHz, CDCl$_3$) δ 168.34, 166.49, 152.54, 140.68, 129.78, 129.49, 127.82, 119.22, 110.86, 84.84, 78.75, 33.81, 27.88, 24.91, 16.23. MS 270 (M+1).

Synthesis of

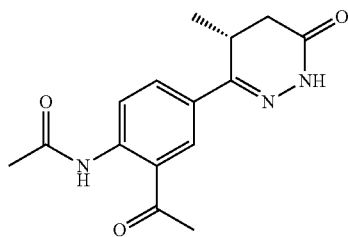

TP52

TP52.

The silyl alkyne above, 20 mg (0.059 mmol) was heated at 80° C. in 0.11 mL of formic acid for 5 h. Solvent removal and chromatography with 0-40% EtOAc in CH$_2$Cl$_2$ yielded 14 mg of product as a white solid (83%). $^1$H NMR (300 MHz, CDCl$_3$) δ 11.75 (s, 1H), 8.82 (d, J=7.0, 1H), 8.80 (s, 1H), 8.44 (d, J=2.1, 1H), 7.82 (dd, J=2.1, 8.9, 1H), 3.43-3.30 (m, 1H), 2.78 (dd, J=6.8, 16.9, 1H), 2.73 (s, 3H), 2.52 (d, J=16.9, 1H), 2.26 (s, 3H), 1.27 (d, J=7.4, 3H). $^{13}$C NMR (75 MHz, CDCl$_3$) δ 202.76, 169.55, 166.47, 152.36, 141.85, 131.98, 129.32, 128.29, 121.95, 120.64, 33.79, 28.61, 27.87, 25.55, 16.21. MS 288 (M+1).

TP44 was made according to the following scheme:

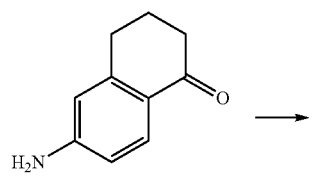

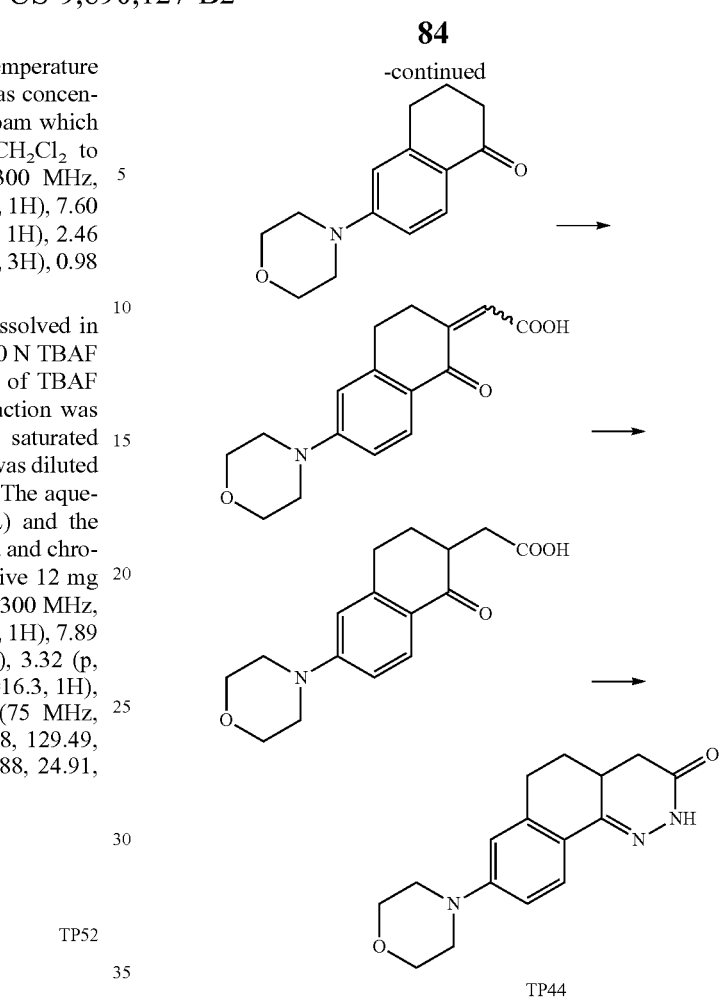

TP44

TP44.

To 1.00 g of 6-amino-3,4-dihydronaphthalen-1(2H)-one (6.20 mmol) dissolved in 6.2 mL of DMF was added 2.57 g of K$_2$CO$_3$ and 0.78 mL of (2-bromoethyl)ether (6.20 mmol). The reaction was placed under argon and stirred at 60° C. overnight. The reaction was cooled, diluted with water, and rinsed with EtOAc. The combined organic layers were washed with water, brine, dried, and concentrated to give an orange oil which was chromatographed with 0-45% EtOAc in hexane to yield 0.44 g of product (31%). $^1$H NMR (300 MHz, CDCl$_3$) δ 7.96 (d, J=8.9, 1H), 6.79 (dd, J=2.6, 8.9, 1H), 6.61 (d, J=2.4, 1H), 3.89-3.81 (m, 4H), 3.36-3.27 (m, 4H), 2.89 (t, J=6.1, 2H), 2.64-2.53 (m, 2H), 2.17-2.06 (m, 2H), MS 232 (M+1).

The next steps were performed according to a literature procedure: *J. Med. Chem.* 1974, 17, 273-281. A suspension of 0.42 g of NaIO$_4$ (2.0 mmol) in 2.3 mL of water was cooled to 0° C. in an ice-bath. Concentrated H$_2$SO$_4$ (38 μL, 0.71 mmol) was added dropwise to give a homogeneous solution. A solution of 290 mg of DL-tartaric acid (1.9 mmol) in 0.6 mL of water was added dropwise to the reaction. The mixture was warmed to room temperature and stirred for 30 min. The morpholino-tetralone, 440 mg (1.9 mmol), was added to the reaction, followed by 5 mL of a 1.45 M aqueous solution of NaOH (7.40 mmol), and 1.1 mL of EtOH. The reaction was stirred overnight at room temperature and then heated to 70° C. and stirred 24 h. After cooling the reaction was washed with diethyl ether (10 mL) and then acidified with HOAc to pH ~3 before rinsing with 10% (v/v) MeOH in CH$_2$Cl$_2$ (3×30 mL). The combined organic layers were washed with brine, dried, and concentrated to give a dark solid. The solid was dissolved in 10% (v/v) MeOH in CH$_2$Cl$_2$ (40 mL) and treated with Amberlyst-21 ion exchange resin (12 g, 1.3 meq/mL). The mixture was stirred at room temperature overnight. The resin was collected by filtration and washed thoroughly with MeOH. The resin was then washed with a mixture of 60/10/30 (v/v) ethyl acetate-methanol-acetic acid until no product was detected in the washings. The combined acidic layers were washed with a saturated solution of sodium bisulfite (200 mL), brine (50 mL), then dried, and concentrated. Chromatography with 0-3% MeOH in CH$_2$Cl$_2$ yielded 0.18 g of product (32%). $^1$H NMR (500 MHz, CDCl$_3$) δ 8.06 (d, J=8.9, 1H), 6.93 (t, J=1.6, 1H), 6.86 (dd, J=2.5, 9.0, 1H), 6.64 (d, J=2.3, 1H), 3.97-3.82 (m, 4H), 3.44 (t, J=5.6, 2H), 3.42-3.32 (m, 4H), 3.06-2.90 (m, 2H), MS 288 (M+1). To 176 mg of this product (0.613 mmol) in 0.8 mL HOAc and 0.4 mL of water was added 100 mg of zinc dust (1.53 mmol) and the mixture was stirred and heated to 100° C. for 1 h. The reaction mixture was filtered while still hot through small amount of Celite, rinsing with hot water (4 mL). The filtrate was cooled to room temperature then extracted with EtOAc (4×5 mL). The combined extracts were dried, concentrated, and chromatographed with 0-1.5% MeOH in CH$_2$Cl$_2$ to yield 50.5 mg of product (29%). $^1$H NMR (500 MHz, CDCl$_3$) δ 11.74 (s br, 1H), 7.97 (d, J=8.9, 1H), 6.80 (dd, J=2.2, 8.9, 1H), 6.61 (s, 1H), 3.98-3.76 (m, 4H), 3.33 (dd, J=3.0, 5.5, 4H), 3.12-3.02 (m, 2H), 2.97 (ddd, J=6.2, 10.9, 12.8, 1H), 2.90 (dt, J=3.3, 16.4, 1H), 2.45 (dd, J=6.6, 16.3, 1H), 2.30-2.19 (m, 1H), 1.95 (qd, J=4.1, 12.9, 1H). $^{13}$C NMR (126 MHz, CDCl$_3$) δ 197.12, 177.76, 154.34, 146.14, 129.59, 123.21, 112.56, 111.93, 66.44, 47.24, 44.07, 35.47, 29.82, 29.48. MS 290 (M+1).

To 50.5 mg of 2-(6-morpholino-1-oxo-1,2,3,4-tetrahydronaphthalen-2-yl)acetic acid (0.175 mmol) suspended in 5 mL of EtOH was added 0.085 mL of a hydrazine hydrate (1.7 mmol) and the reaction was heated at 90° C. overnight. The reaction was cooled, concentrated, and chromatography with 0-4% MeOH in CH$_2$Cl$_2$ to yield 42 mg of white solid (84%). $^1$H NMR (500 MHz, CDCl$_3$) δ 8.85 (s, 1H), 7.99 (d, J=8.9, 1H), 6.84 (dd, J=2.1, 8.8, 1H), 6.63 (s, 1H), 3.94-3.78 (m, 4H), 3.33-3.13 (m, 4H), 2.91-2.72 (m, 3H), 2.66 (dd, J=6.4, 16.6, 1H), 2.26 (t, J=16.2, 1H), 2.21-2.10 (m, 1H), 1.69-1.53 (m, 1H). $^{13}$C NMR (126 MHz, CDCl$_3$) δ 168.19, 151.99, 150.63, 140.65, 125.73, 121.24, 113.93, 113.41, 66.58, 48.12, 33.49, 33.28, 29.56, 29.10. MS 286 (M+1).

TP59 was made according to the following scheme:

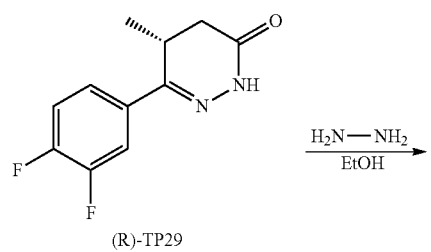

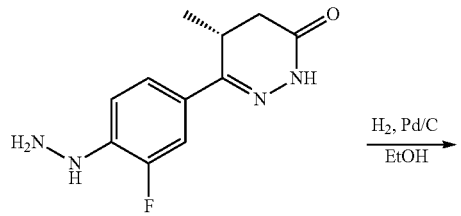

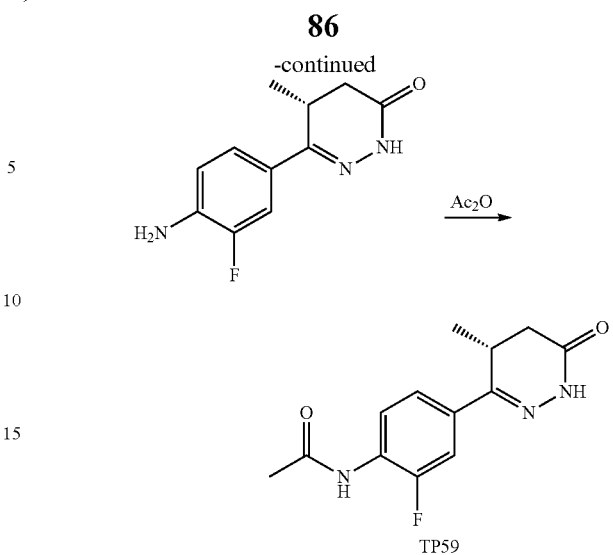

TP59.

A solution of 150 mg of (R)-TP29 (0.67 mmol) in 3 mL of EtOH and 300 uL of hydrazine hydrate (6.2 mmol) was heated at 100° C. overnight. After cooling, the product was filtered off and rinsed with cold EtOH, 119 mg of white solid was obtained (75%). $^1$H NMR (300 MHz, CDCl$_3$) δ 8.50 (s, 1H), 7.53-7.35 (m, 2H), 7.13 (t, J=8.7, 1H), 5.63 (s, 1H), 3.63 (s, 2H), 3.36-3.23 (m, 1H), 2.70 (dd, J=6.8, 16.9, 1H), 2.46 (d, J=16.5, 1H), 1.24 (d, J=7.4, 3H). $^{19}$F NMR (282 MHz, CDCl$_3$) δ −135.45 to −135.58 (m, 1F). MS 237 (M+1). This material was dissolved in 50 mL of MeOH and 200 mg of 10% Pd on carbon was added before stirring under a H$_2$ atmosphere (balloon) for 1 h. The solvent was degassed, the reaction was filtered over Celite and concentrated to give clean product. $^1$H NMR (300 MHz, CDCl$_3$) δ 8.80 (s, 1H), 7.47 (dd, J=1.8, 12.7, 1H), 7.33 (dd, J=1.6, 8.4, 1H), 6.78 (t, J=8.7, 1H), 4.00 (s, 2H), 3.33-3.18 (m, 1H), 2.69 (dd, J=6.7, 16.9, 1H), 2.45 (d, J=16.8, 1H), 1.23 (d, J=7.4, 3H). $^{19}$F NMR (282 MHz, CDCl$_3$) δ −134.85 (dd, J=9.1, 12.7, 1F). MS 222 (M+1). The crude product was stirred overnight in 20 mL acetic anhydride. Concentration and chromatography with 50-100% EtOAc in hexane gave 45 mg of product as an off-white solid (34%). $^1$H NMR (300 MHz, CDCl$_3$) δ 8.27 (t, J=8.3, 1H), 7.60 (dd, J=1.9, 12.5, 1H), 7.48 (d, J=8.6, 1H), 3.32 (d, J=7.1, 1H), 2.72 (dd, J=6.9, 17.0, 1H), 2.45 (dd, J=1.4, 17.0, 1H), 2.23 (s, 3H), 1.23 (d, J=7.4, 3H). $^{19}$F NMR (282 MHz, CDCl$_3$) δ −124.85 (dd, J=8.1, 12.4, 1F). MS 264 (M+1). Racemic material (TP57) was made via the same procedure.

TP58 was made according to the following scheme

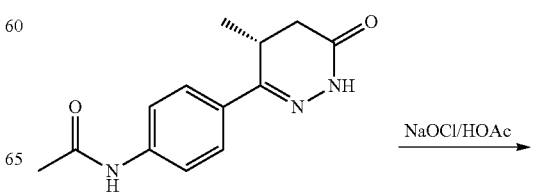

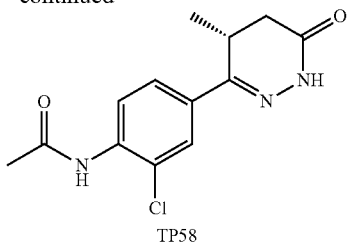

TP58.

To 80 mg of TP6 Int. (0.33 mmol) dissolved in 1 mL HOAc was added 1 mL 10-15% NaOCl(aq) and the reaction was stirred 3 d. Water and $CH_2Cl_2$ were added, the $CH_2Cl_2$ was treated with $NaHCO_3$ (solid and aqueous) until neutral, then the $CH_2Cl_2$ was rinsed with brine, dried, concentrated and chromatographed with 50-80% EtOAc to yield 37 mg of product as an off-white solid (41%). $^1H$ NMR (300 MHz, $CDCl_3$) δ 9.18 (s, 1H), 8.46 (d, J=8.5, 1H), 7.87 (s, 1H), 7.78 (s, 1H), 7.61 (d, J=8.7, 1H), 3.38-3.23 (m, 1H), 2.72 (dd, J=6.8, 16.9, 1H), 2.49 (d, J=16.9, 1H), 2.28 (s, 3H), 1.24 (d, J=7.4, 3H). $^{13}C$ NMR (75 MHz, $CDCl_3$) δ 168.33, 166.58, 152.16, 135.75, 130.87, 126.49, 125.29, 122.93, 121.10, 33.77, 27.87, 24.84, 16.22. MS 280 (M+1). Anal: Calc. for $C_{13}H_{14}ClN_3O_2$: C, 55.82; H, 5.04; N, 15.02. Found. C, 56.04; H, 4.82; N, 15.01.

Synthesis of

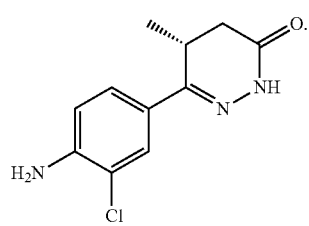

To 1.89 g of TP58 (6.76 mmol) in 100 mL of EtOH was added 1.08 g of NaOH (27.0 mmol) and the mixture was heated at reflux temperature for 90 min before cooling, neutralizing with 15 mL of 10% HCl and concentration. The mixture was partitioned between water and EtOAc, the EtOAc was dried and concentrated to 1.57 g of white solid (98%). 1H NMR (400 MHz, DMSO-d6) δ 10.76 (s, 1H), 7.60 (d, J=2.4 Hz, 1H), 7.47 (dd, J=8.7, 2.4 Hz, 1H), 6.81 (d, J=8.4 Hz, 1H), 5.75 (s, 2H), 3.33-3.21 (m, 1H), 2.62 (dd, J=16.6, 6.5 Hz, 1H), 2.18 (d, J=16.8 Hz, 1H), 1.03 (d, J=7.1 Hz, 3H); 13C NMR (101 MHz, DMSO) δ 166.63, 152.44, 146.26, 126.91, 125.98, 123.83, 117.48, 115.40, 34.01, 27.26, 16.42. Mass 238 (M+1).

Synthesis of

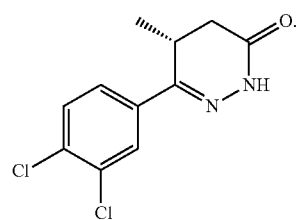

A solution of 1.40 g of TP62 (5.89 mmol) in 20 mL of concentrated HCl was cooled on an ice bath before the slow addition of 406 mg of $NaNO_2$ (5.89 mmol) in 5 mL water. After stirring 30 min, the solution was added to an ice-cold solution of 583 mg of CuCl (5.89 mmol) dissolved in a mixture of 8 mL of water and 4 mL of concentrated HCl. After warming to room temperature and stirring 90 min, the mixture was transferred to a separatory funnel and rinsed several times with $CH_2Cl_2$. The combined $CH_2Cl_2$ layers were rinsed with brine, dried, concentrated and chromatographed with 0-40% EtOAc in hexane to yield 1.10 g of product as a faintly yellow solid which was recrystallized from $CH_2Cl_2$ to give 880 mg of product (58%). 1H NMR (400 MHz, DMSO-d6) δ 11.11 (s, 1H), 7.96 (s, 1H), 7.76 (d, J=9.2 Hz, 1H), 7.69 (d, J=8.5 Hz, 1H), 3.41 (p, J=7.1 Hz, 1H), 2.72 (dd, J=16.8, 6.9 Hz, 1H), 2.26 (d, J=16.9 Hz, 1H), 1.06 (d, J=7.0 Hz, 3H). 13C NMR (101 MHz, DMSO) δ 166.80, 150.90, 135.96, 132.22, 132.06, 131.30, 127.82, 126.31, 33.80, 27.31, 16.17. Mass 257 (M+1).

Synthesis of

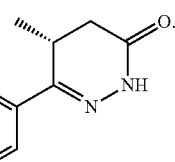

A solution of 110 mg of TP60 (428 mmol) in 2 mL of morpholine and 3 mL of NMP were heated in a sealed microwave vessel at 200 degrees C. for 8 h. After cooling, water and EtOAc were added, the water was rinsed several times with EtOAc and the combined EtOAc layers were rinsed with water and brine several times before drying and concentrating. Chromatography with 50-100% EtOAc in hexane followed by recrystallization from MeOH yielded 7.6 mg of product (6%). 1H NMR (400 MHz, Chloroform-d) δ 8.80 (s, 1H), 7.81 (s, 1H), 7.61 (d, J=8.2 Hz, 1H), 7.04 (d, J=8.3 Hz, 1H), 3.99-3.78 (m, 4H), 3.30 (p, J=7.4 Hz, 1H), 3.21-2.99 (m, 4H), 2.70 (dd, J=16.9, 6.9 Hz, 1H), 2.48 (d, J=17.0 Hz, 1H), 1.24 (d, J=7.2 Hz, 3H). Mass 308 (M+1).

Example 16

Compounds as shown were tested against various cells lines in vitro according to the methods described herein. Cells are plated in 384-well format in a total volume of 40 µl. Indicated compound concentrations were added 24 hrs after plating the cells. After 48 hrs cell viability was determined using Cell Titer Glo® Luminescent Cell Viability Assay. $IC_{50}$ were calculated as indicated in the following table. The compounds were also tested against a glioblastomas cell line (GB1) and were found to have activity against that type of cell line as well (data not shown).

| Compound | Cell Line (Values are EC$_{50}$ (nM)) | | | | |
|---|---|---|---|---|---|
| | HeLa | A549 | H2122 | COLO741 | HEL |
| 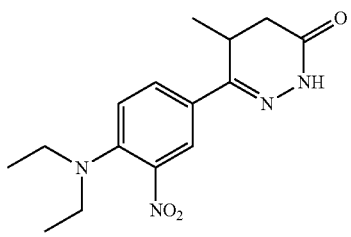 | 5.5-8.7 | >10,000 | 10.3-15.6 | | |
| 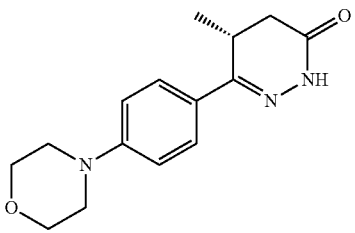 [SMILES: C[C@@H]1CC(=O)NN=C1c1ccc(N2CCOCC2)cc1] | 10.3-12.1 | >10,000 | 11.8 | 14.5-18.9 | 25.7-58.4 |
| 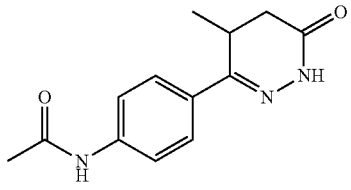 [SMILES: CC(=O)Nc1ccc(C2=NNC(=O)CC2C)cc1] | >10,000 | >10,000 | | | |
| 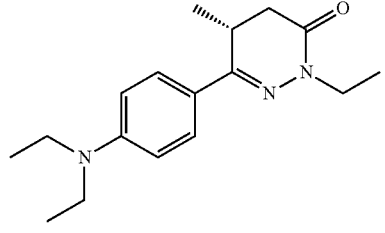 [SMILES: CCN1N=C(c2ccc(N(CC)CC)cc2)[C@H](C)CC1=O] | >10,000 | >10,000 | >1000 | >1000 | |
| 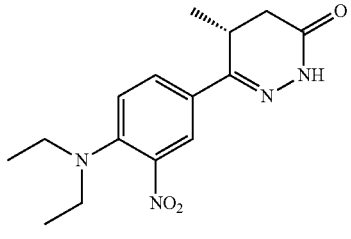 [SMILES: CCN(CC)c1ccc(C2=NNC(=O)C[C@H]2C)cc1[N+](=O)[O-]] | 2.63 | >10,000 | 3.62 | 3.97 | 13.5 |
| 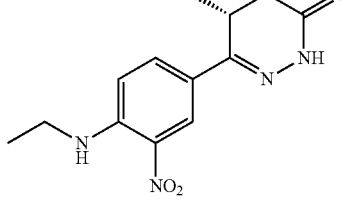 | 0.461 | >10,000 | 0.8 | 0.76 | 3.98 |

| Structure | | | | | |
|---|---|---|---|---|---|
| (acetamido-nitrophenyl dihydropyridazinone, (S)-Me) | 0.00608 | >10,000 | | | |
| (acetamido-phenyl dihydropyridazinone, (S)-Me) | >10,000 | >10,000 | | | |
| (diethylamino-nitrophenyl dihydropyridazinone, (S)-Me) | 4.05 | >10,000 | 7.4 | 3.6-4.4 | 11.3-16.2 |
| (acetamido-bromophenyl dihydropyridazinone, (S)-Me) | 42.1 | >10,000 | | | |
| (amino-bromophenyl dihydropyridazinone, (S)-Me) | >10,000 | >10,000 | | | |
| (acetamido-phenyl methylpyridazinone) | >1000 | >10,000 | | | |
| (aminophenyl methylpyridazinone) | >1000 | >10,000 | | | |

| Structure | >1000 | >10,000 | |
|---|---|---|---|
| (4-diethylamino-phenyl methylpyridazinone) | >10,000 | 16.5 | 38.7 |
| (4-morpholinophenyl methyl-dihydropyridazinone) | | | |
| (2-methylbenzimidazole methyl-dihydropyridazinone) | | | |
| (acetamido-aminophenyl methyl-dihydropyridazinone) | | | |

| | Potency (EC$_{50}$ nM) Mean ± SD (n = 3) | |
|---|---|---|
| Structure | HeLa | A549 |
| (diethylamino-nitrophenyl methyl-dihydropyridazinone) | 6.9 ± 0.9 | >10,000 |
| (diethylamino-nitrophenyl methyl-dihydropyridazinone) | 3.8 ± 1.1 | >10,000 |
| (ethylamino-nitrophenyl methyl-dihydropyridazinone) | 1.1 ± 0.5 | >10,000 |

| Structure | | |
|---|---|---|
| (diethylamino-phenyl, 4-Me pyridazinone) | 8.8 ± 2.3 | >10,000 |
| (diethylamino-phenyl, 4-Me (wedge) pyridazinone) | 3.8 ± 0.8 | >10,000 |
| (ethylamino-phenyl, 4-Me (wedge) pyridazinone) | 71 ± 7 | >10,000 |
| (diethylamino-phenyl, 4-Me (wedge) N-ethyl pyridazinone) | >1000 | >10,000 |
| (diethylamino, H2N-substituted phenyl, 4-Me pyridazinone) | 240 ± 60 | >10,000 |
| (diethylamino, NHAc-substituted phenyl, 4-Me pyridazinone) | >1000 | >10,000 |
| (morpholino-phenyl, 4-Me pyridazinone) | 36 ± 9 | >10,000 |
| (morpholino-phenyl, 4-Me (wedge) pyridazinone) | 13 ± 2 | >10,000 |
| (morpholino, F-substituted phenyl, 4-Me pyridazinone) | 2.8 ± 0.7 | >10,000 |

-continued
| Structure | | |
|---|---|---|
| 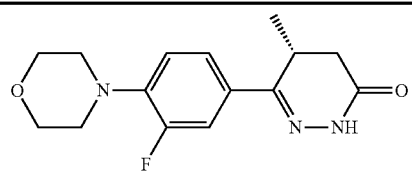 | 1.6 ± 0.2 | >10,000 |
| 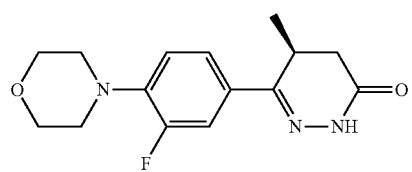 [SMILES: C[C@H]1CC(=O)NN=C1c1ccc(N2CCOCC2)c(F)c1] | >1000 | >10,000 |
| 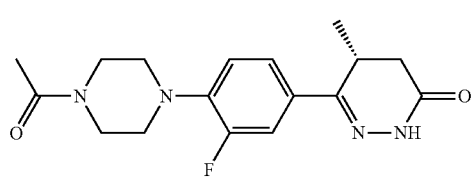 [SMILES: CC(=O)N1CCN(c2ccc(C3=NNC(=O)C[C@H]3C)cc2F)CC1] | >1000 | >10,000 |
| 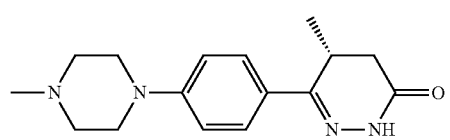 [SMILES: C[C@@H]1CC(=O)NN=C1c1ccc(N2CCN(C)CC2)cc1] | 310 ± 120 | >10,000 |
| 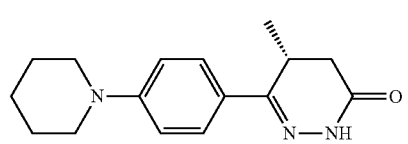 [SMILES: C[C@@H]1CC(=O)NN=C1c1ccc(N2CCCCC2)cc1] | 3.9 ± 0.6 | >10,000 |
| 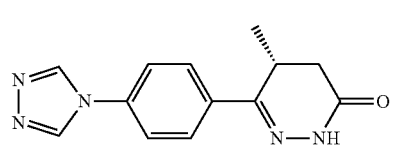 [SMILES: C[C@@H]1CC(=O)NN=C1c1ccc(-n2cnnc2)cc1] | >1000 | >10,000 |
| 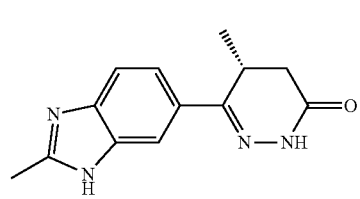 [SMILES: Cc1nc2ccc(C3=NNC(=O)C[C@H]3C)cc2[nH]1] | >1000 | >10,000 |
| 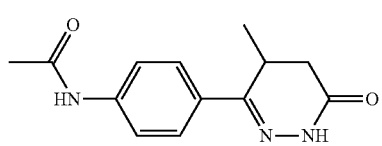 | >1000 | >10,000 |
| 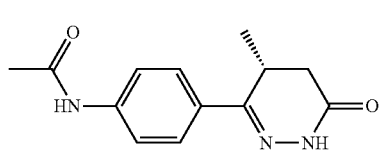 [SMILES: CC(=O)Nc1ccc(C2=NNC(=O)C[C@H]2C)cc1] | >1000 | >10,000 |
| 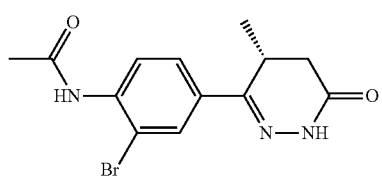 | 21 ± 1 | >10,000 |

| | | |
|---|---|---|
| 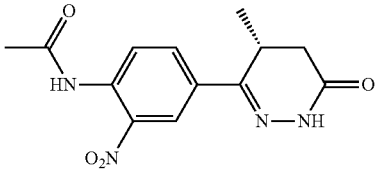 | 4.9 ± 1.1 | >10,000 |
| 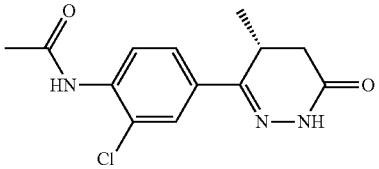 [SMILES: CC(=O)Nc1ccc(C2=NNC(=O)C[C@H]2C)cc1Cl] | 30 | >10,000 |
| 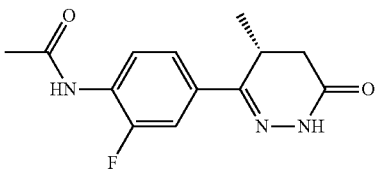 [SMILES: CC(=O)Nc1ccc(C2=NNC(=O)C[C@H]2C)cc1F] | >1,000 | >10,000 |
| 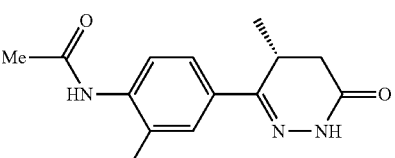 | 65 ± 10 | >10,000 |
| 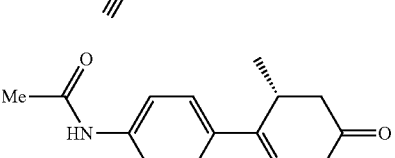 | 130 ± 10 | >10,000 |
| 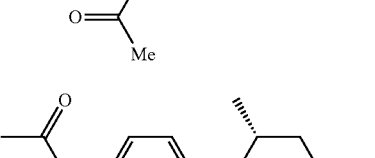 | >1000 | >10,000 |
| 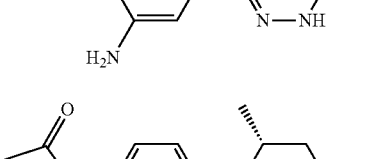 | 140 ± 50 | >10,000 |
| 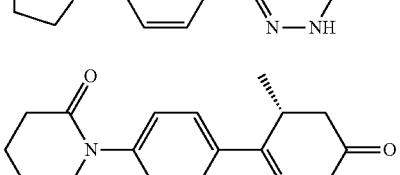 | >1000 | >10,000 |
| 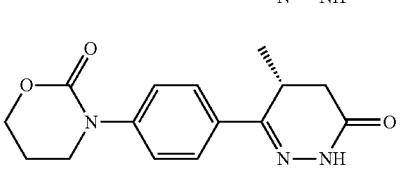 | >1000 | >10,000 |

-continued

| Structure | | |
|---|---|---|
| (sulfonyl-morpholine phenyl methylpyridazinone) | 330 ± 6 | >10,000 |
| (phenyl methylpyridazinone) | 430 ± 50 | >10,000 |
| (4-F-phenyl methylpyridazinone) | 410 ± 270 | >10,000 |
| (4-Cl-phenyl methylpyridazinone) | 33 ± 5 | >10,000 |
| (3,4-diF-phenyl methylpyridazinone) | 64 ± 3 | >10,000 |
| (3,4-diF-phenyl methylpyridazinone) | 22 ± 5 | >10,000 |
| (3,4-diF-phenyl methylpyridazinone) | >1000 | >10,000 |
| (4-I-phenyl methylpyridazinone) | 7.1 ± 0.8 | >10,000 |
| (4-propenyl-phenyl methylpyridazinone) | 8.8 ± 1.1 | >10,000 |
| (4-propyl-phenyl methylpyridazinone) | 16 ± 1 | >10,000 |

-continued

| Structure | | |
|---|---|---|
| cyclohexenyl-phenyl-(methyl)dihydropyridazinone | 2.2 ± 0.4 | >10,000 |
| cyclohexyl-phenyl-(methyl)dihydropyridazinone | 7.7 ± 1.3 | >10,000 |
| pyrimidinyl-phenyl-(methyl)dihydropyridazinone | 13 ± 2 | >10,000 |
| acetamido-phenyl-methylpyridazinone | >1000 | >10,000 |
| aminophenyl-methylpyridazinone | >1000 | >10,000 |
| (diethylamino)phenyl-methylpyridazinone | >1000 | >10,000 |
| aminophenyl-dimethylpyrazolone | >1000 | >10,000 |
| (diethylamino)phenyl-dimethylpyrazolone | >1000 | >10,000 |
| morpholinophenyl-dimethylpyrazolone | >1000 | >10,000 |
| chlorophenyl-dimethylpyrazolone | >1000 | >10,000 |
| morpholino-tetrahydronaphthyl-pyridazinone | >1000 | >10,000 |

Example 17

Known PDE3 inhibitors as shown below were tested against various cells lines in vitro according to the methods described herein. Cells are plated in 384-well format in a total volume of 40 µl. Indicated compound concentrations were added 24 hrs after plating the cells. After 48 hrs cell viability was determined using Cell Titer Glo® Luminescent Cell Viability Assay. $IC_{50}$ were calculated as indicated in the following table. Various PDE3 inhibitors were shown to be able to inhibit the growth of cancer cells in vitro.

| Name | Structure | Potency ($EC_{50}$ nM) Mean (n = 3) HeLa | A549 | PDE3 activity (ref) |
|---|---|---|---|---|
| Trequinsin | Trequinsin | >10,000 | >10,000 | 0.25 nM |
| Cilostamide | Cilostamide | >10,000 | >10,000 | 27 nM |
| Milrinone | Milrinone | >10,000 | >10,000 | 56 nM |
| Zardaverine | Zardaverine | 56 | >10,000 | 2500 nM |
| Anagrelide | Anagrelide | 8.2 | >10,000 | 36 nM |

-continued

| Name | Structure | Potency (EC$_{50}$ nM) Mean (n = 3) | | PDE3 activity (ref) |
|---|---|---|---|---|
| | | HeLa | A549 | |
| Imazodan | Imazodan | 720 | >10,000 | 1300 nM |
| Siguazodan | Siguazodan | >10,000 | >10,000 | 117 nM |
| Levosimendan | Levosimendan | >10,000 | >10,000 | 2.4 nM |
| OR-1896 | OR-1896 | >10,000 | >10,000 | 94 nM |

Example 18

Compounds as shown were tested against various cells lines in vitro according to the methods described herein. Cells are plated in 384-well format in a total volume of 40 µl. Indicated compound concentrations were added 24 hrs after plating the cells. After 48 hrs cell viability was determined using Cell Titer Glo® Luminescent Cell Viability Assay. IC$_{50}$ were calculated as indicated in the following table.

| Structure | Potency (EC$_{50}$ nM) Mean ± SD (n = 3) | | | | | |
|---|---|---|---|---|---|---|
| | HeLa | H2122 | COLO741 | A549 | HCT116 | IMR90 |
| 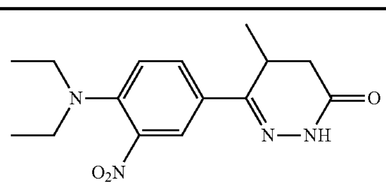 | 6.9 ± 0.9 | 13.7 ± 2.8 | 12.0 ± 1.3 | NA | NA | NA |

-continued

| Structure | | | | | | |
|---|---|---|---|---|---|---|
| 4-cyclohexylphenyl pyridazinone | 7.7 ± 1.3 | 29.6 ± 8.7 | 11.4 ± 0.3 | NA | NA | NA |
| 4-morpholino-3-fluorophenyl pyridazinone | 1.6 ± 0.2 | 3.2 ± 1.1 | 3.1 ± 0.6 | NA | NA | NA |
| 4-chlorophenyl pyridazinone | 32.9 ± 5.4 | 80.8 ± 6.1 | 43.3 ± 9.2 | NA | NA | NA |
| 4-morpholinophenyl pyridazinone | 13.1 ± 1.9 | 31.4 ± 10.8 | 20.2 ± 4.8 | NA | NA | NA |
| 4-(pyrimidin-5-yl)phenyl pyridazinone | 12.7 ± 2.2 | 37.8 ± 12.3 | 19.8 ± 1.8 | NA | NA | NA |
| 3,4-difluorophenyl pyridazinone | 22.3 ± 4.5 | 47.7 ± 14.1 | 33.2 ± 1.4 | NA | NA | NA |
| 4-acetamido-3-nitrophenyl pyridazinone | 4.9 ± 1.1 | 12.3 ± 3.4 | 7.8 ± 0.3 | NA | NA | NA |
| 4-(diethylamino)phenyl N-ethyl pyridazinone | NA | NA | NA | NA | NA | NA |
| 4-morpholino-3-fluorophenyl pyridazinone (variant) | NA | NA | NA | NA | NA | NA |

-continued
| Structure | | | | | | |
|---|---|---|---|---|---|---|
| 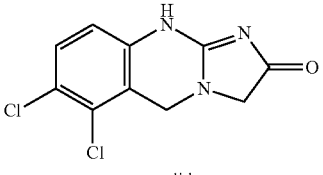 anagrelide | 6.8 ± 0.9 | 17.4 ± 3.5 | 12.2 ± 0.9 | NA | NA | NA |
| 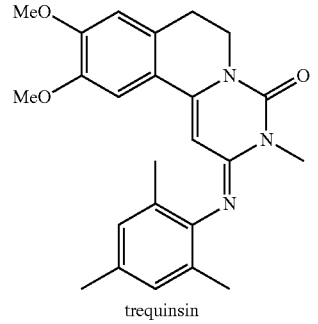 trequinsin | NA | NA | NA | NA | NA | NA |
| | Potency (EC$_{50}$) (n = 2) | | | |
|---|---|---|---|---|
| Structure | H1563 | A549 | H2122 | HeLa |
| 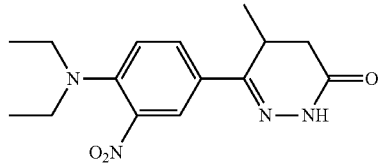 | 12 nM | >10 μM | 12 nM | 4 nM |
| 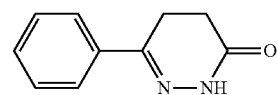 [SMILES: O=C1CCC(c2ccccc2)=NN1] | >10 μM | >10 μM | NT | NT |
| 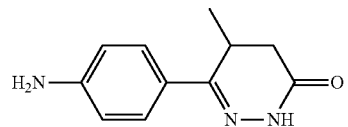 | >10 μM | >10 μM | NT | NT |
| 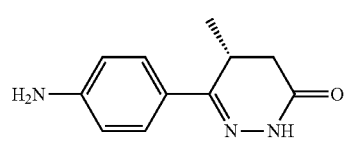 | >10 μM | >10 μM | NT | NT |
| 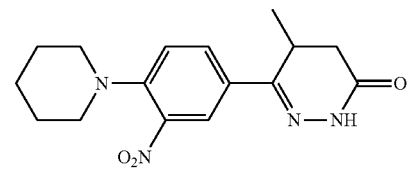 [SMILES: CC1CC(=O)NN=C1c1ccc(N2CCCCC2)c([N+](=O)[O-])c1] | 3 nM | >10 μM | 1 nM | 1 nM |
| 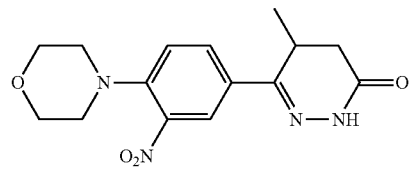 | 3 nM | >10 μM | NT | NT |

| Structure | | | | |
|---|---|---|---|---|
| MeO-phenyl-CH2-C(O)-piperazine-N-(phenyl with NO2)-4-methyl-pyridazinone | >10 μM | >10 μM | NT | NT |
| H2N-(phenyl with NO2)-4-methyl-pyridazinone | >10 μM | >10 μM | NT | NT |
| Me2N-(phenyl with NO2)-4-methyl-pyridazinone | 40 nM | >10 μM | NT | NT |
| HO-CH2CH2-NH-(phenyl with NO2)-4-methyl-pyridazinone | 40 nM | >10 μM | 11 nM | 4 nM |
| H2N,H2N-phenyl-4-methyl-pyridazinone | >10 μM | >10 μM | NT | NT |
| NC-N=C(NH-Me)(NH)-phenyl-4-methyl-pyridazinone | >10 μM | >10 μM | NT | NT |
| 2-O2N-phenyl-CH=N-phenyl-4-methyl-pyridazinone | >10 μM | >10 μM | NT | NT |
| phthalazinone-CH2-COOH | >10 μM | >10 μM | NT | NT |

| Structure | | | | |
|---|---|---|---|---|
| 4-(diethylamino)-N-(3-methoxyphenyl)-3-nitrobenzamide | >10 μM | >10 μM | NT | NT |
| 4-(diethylamino)-3-nitrobenzonitrile | >10 μM | >10 μM | NT | NT |
| 4-(diethylamino)-3-nitrobenzoic acid | >10 μM | >10 μM | NT | NT |
| 4-(diethylamino)-5-(3-isopropyl-1,2,4-oxadiazol-5-yl)-2-nitrobenzene | NT | >10 μM | NT | >10 μM |
| 6-(4-chlorophenyl)-5-methyl-2-phenyl-4,5-dihydropyridazin-3(2H)-one | NT | >10 μM | NT | >10 μM |
| 5-methyl-6-(thiophen-2-yl)-4,5-dihydropyridazin-3(2H)-one | NT | >10 μM | NT | >10 μM |
| 3-phenyl-1H-pyrazol-5(4H)-one | NT | >10 μM | NT | >10 μM |
| 4-(diethylamino)-3-nitro-N-phenylbenzamide | NT | >10 μM | NT | >10 μM |

| | NT | >10 μM | NT | >10 μM |

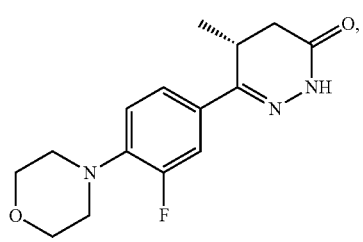 [SMILES: C[C@@H]1CC(=O)NN=C1c1ccc(N2CCOCC2)c(F)c1]

| | NT | >10 μM | NT | >10 μM |

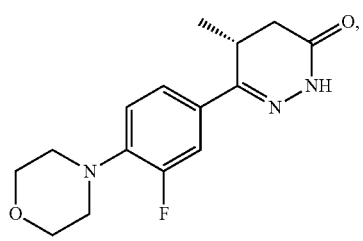 [SMILES: C[C@@H]1CC(=O)NN=C1c1ccc(N2CCOCC2)c(F)c1]

What is claimed is:

1. A compound having a formula of:

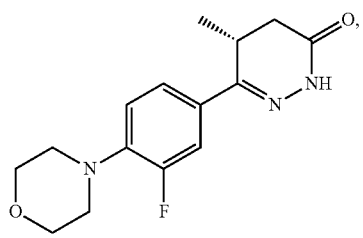 [SMILES: C[C@@H]1CC(=O)NN=C1c1ccc(N2CCOCC2)c(F)c1]

or a pharmaceutically acceptable salt or ester thereof.

2. A pharmaceutical composition comprising a compound having a formula of:

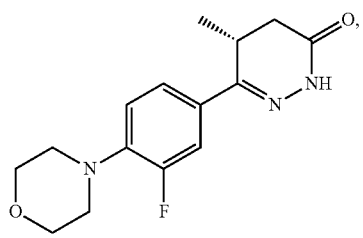 [SMILES: C[C@@H]1CC(=O)NN=C1c1ccc(N2CCOCC2)c(F)c1]

or a pharmaceutically acceptable salt or ester thereof.

3. The compound of claim 1 having a formula of:

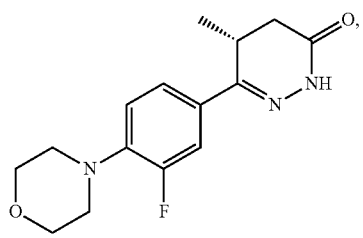 [SMILES: C[C@@H]1CC(=O)NN=C1c1ccc(N2CCOCC2)c(F)c1]

or a pharmaceutically acceptable salt thereof.

4. The compound of claim 1 having a formula of:

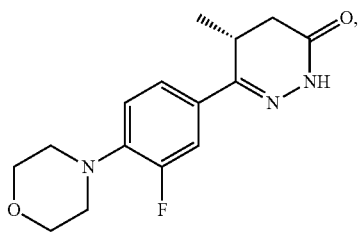 [SMILES: C[C@@H]1CC(=O)NN=C1c1ccc(N2CCOCC2)c(F)c1]

or an ester thereof.

5. The pharmaceutical composition of claim 2, wherein the compound has a formula of:

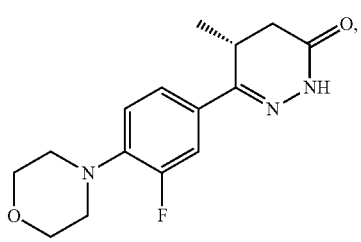

or a pharmaceutically acceptable salt thereof.

6. The pharmaceutical composition of claim 2, wherein the compound has a formula of:

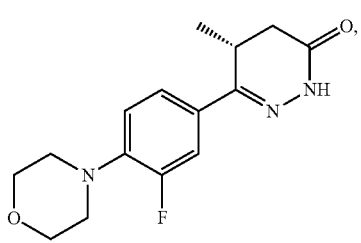

or an ester thereof.

7. The pharmaceutical composition of claim 2, wherein the compound, or a pharmaceutically acceptable salt thereof, is present in amount of at least 90% optical purity.

8. The pharmaceutical composition of claim 2, wherein the compound, or a pharmaceutically acceptable salt or ester thereof, is present in amount of at least 95% optical purity.

9. The pharmaceutical composition of claim 2, wherein the compound, or a pharmaceutically acceptable salt or ester thereof, is present in amount of at least 96% optical purity.

10. The pharmaceutical composition of claim 2, wherein the compound, or a pharmaceutically acceptable salt or ester thereof, is present in amount of at least 98% optical purity.

11. The pharmaceutical composition of claim 2, wherein the compound, or a pharmaceutically acceptable salt or ester thereof, is present in amount of at least 99% optical purity.

12. The pharmaceutical composition of claim 2, wherein the pharmaceutical composition is suitable for oral or parenteral administration.

* * * * *